US009271999B2

(12) United States Patent
Marcus

(10) Patent No.: US 9,271,999 B2
(45) Date of Patent: *Mar. 1, 2016

(54) TREATMENT OF MYELOSUPPRESSION

(71) Applicant: Cantex Pharmaceuticals, Inc., Weston, FL (US)

(72) Inventor: Stephen Marcus, Weston, FL (US)

(73) Assignee: Cantex Pharmaceuticals, Inc., Weston, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/801,990

(22) Filed: Mar. 13, 2013

(65) Prior Publication Data

US 2013/0303481 A1    Nov. 14, 2013

Related U.S. Application Data

(60) Provisional application No. 61/724,836, filed on Nov. 9, 2012, provisional application No. 61/702,207, filed on Sep. 17, 2012, provisional application No. 61/678,053, filed on Jul. 31, 2012, provisional application No. 61/668,709, filed on Jul. 6, 2012, provisional application No. 61/664,611, filed on Jun. 26, 2012, provisional application No. 61/653,362, filed on May 30, 2012, provisional application No. 61/648,043, filed on May 16, 2012, provisional application No. 61/644,623, filed on May 9, 2012, provisional application No. 61/644,556, filed on May 9, 2012.

(51) Int. Cl.
  *A61K 31/727* (2006.01)
  *A61K 35/28* (2015.01)
  *A61K 39/395* (2006.01)
  *A61N 5/00* (2006.01)
  *A61K 45/06* (2006.01)

(52) U.S. Cl.
  CPC ............... *A61K 31/727* (2013.01); *A61K 35/28* (2013.01); *A61K 39/395* (2013.01); *A61K 45/06* (2013.01); *A61N 5/00* (2013.01)

(58) Field of Classification Search
  None
  See application file for complete search history.

(56) References Cited

U.S. PATENT DOCUMENTS

| 5,296,471 A | 3/1994 | Holme |
| 5,668,118 A | 9/1997 | Kennedy |
| 5,696,100 A | 12/1997 | Holme |
| 5,707,974 A | 1/1998 | Kennedy |
| 5,808,021 A | 9/1998 | Holme |
| 5,912,237 A | 6/1999 | Kennedy |
| 5,990,097 A | 11/1999 | Kennedy |
| 6,077,683 A | 6/2000 | Kennedy |
| 6,489,311 B1 | 12/2002 | Kennedy |
| 6,743,426 B2 | 6/2004 | Fisher |
| 7,468,358 B2 | 12/2008 | Kennedy |
| 7,538,096 B2 | 5/2009 | Hales et al. |
| 8,734,804 B2 | 5/2014 | Marcus |
| 2003/0083231 A1 | 5/2003 | Ahlem |
| 2004/0180812 A1 | 9/2004 | Dicker et al. |
| 2006/0040896 A1 | 2/2006 | Kennedy |
| 2009/0036405 A1 | 2/2009 | Kennedy |
| 2009/0054374 A1 | 2/2009 | Kennedy |
| 2009/0238852 A1 | 9/2009 | Kennedy |
| 2010/0215751 A1 | 8/2010 | Desai |
| 2012/0052055 A1* | 3/2012 | Erickson-Miller .... A61K 45/06 424/94.64 |
| 2012/0196828 A1 | 8/2012 | Marcus |

FOREIGN PATENT DOCUMENTS

| EP | 1807095 B1 | 5/2011 |
| WO | WO 98/04133 A | 2/1998 |
| WO | WO 01/19376 A | 3/2001 |
| WO | WO 01/82918 A2 | 11/2001 |
| WO | WO 2004/050673 A2 | 6/2004 |
| WO | WO 2006/007392 A1 | 1/2006 |
| WO | WO 2009/015183 A1 | 1/2009 |
| WO | WO 2011/116954 A2 | 9/2011 |
| WO | WO 2012/106379 A1 | 8/2012 |

OTHER PUBLICATIONS

Khorana, A. et al "Thromboembolism in hospitalized neutropenic cancer patients" J. Clin. Oncol. (2006) vol. 24, pp. 484-490.*
Niers, T. et al "Mechanisms of heparin induced anti-cancer activity..." Crit. Rev. Oncol. Hematol. (2007) vol. 61, pp. 195-207.*
Mousa, S. et al "Anti-metastatic effect of a non-anticoagulant..." Thromb. Haemost. (2006) vol. 96, pp. 816-821.*
Fabris, F. et al "Heparin-induced thrombocytopenia..." Clin. Appl. Thrombosis/Hemostasis (1997) vol. 3, No. 3, pp. 203-209.*
PCT International Search Report and Written Opinion of the International Searching Authority from PCT/US13/31053 dated Jul. 1, 2013.
"Efficacy & Safety of ODSH (2-0, 3-0 Desulfated Heparin) in Patients With Metastatic Pancreatic Cancer Treated With Gemcitabine & Abraxane (PGPC1)," *ClinicalTrials.gov* 2012.
Prescribing Information for "GEMZAR (gemcitabine hydrochloride) Injection, Powder, Lyophilized, for Solution for Intervenous Use," *Eli Lilly and Company* 2010.
Ahmad et al., 1999 "Functional Heterogeneity of Antiheparin-Platelet Factor 4 Antibodies: Implications in the Pathogenesis of the HIT Syndrome," *Clinical and Applied Thrombosis/Hemostatis: Official Journal of the International Academy of Clinical and Applied Thrombosis/Hemostatis*, 5(1):S32-S37.
Ahmad et al., 1999 "Synthetic Pentasaccharides Do Not Cause Platelet Activation by Antiheparin-Platelet Factor 4 Antibodies," *Clin Appl Thrombosis/Hemostasis* 5(4)259-266.
Bates et al., 2005 "Coagulation Assays," *Circulation* 112:e53-e60.
Burris et al., 1997 "Improvements in survival and clinical benefit with gemcitabine as first-line therapy for patients with advanced pancreas cancer: a randomized trial," *J Clin Oncol*, 15(6):2403-2413.

(Continued)

Primary Examiner — Leigh C Maier
(74) *Attorney, Agent, or Firm* — Fenwick & West LLP

(57) ABSTRACT

Methods are presented for attenuating myelosuppressive side effects of treatment regimens, promoting thrombopoiesis and neutrophil production, and increasing efficacy of treatment regimens, by administering PF4-interacting heparinoids.

22 Claims, 25 Drawing Sheets

(56) References Cited

OTHER PUBLICATIONS

Figure 1:
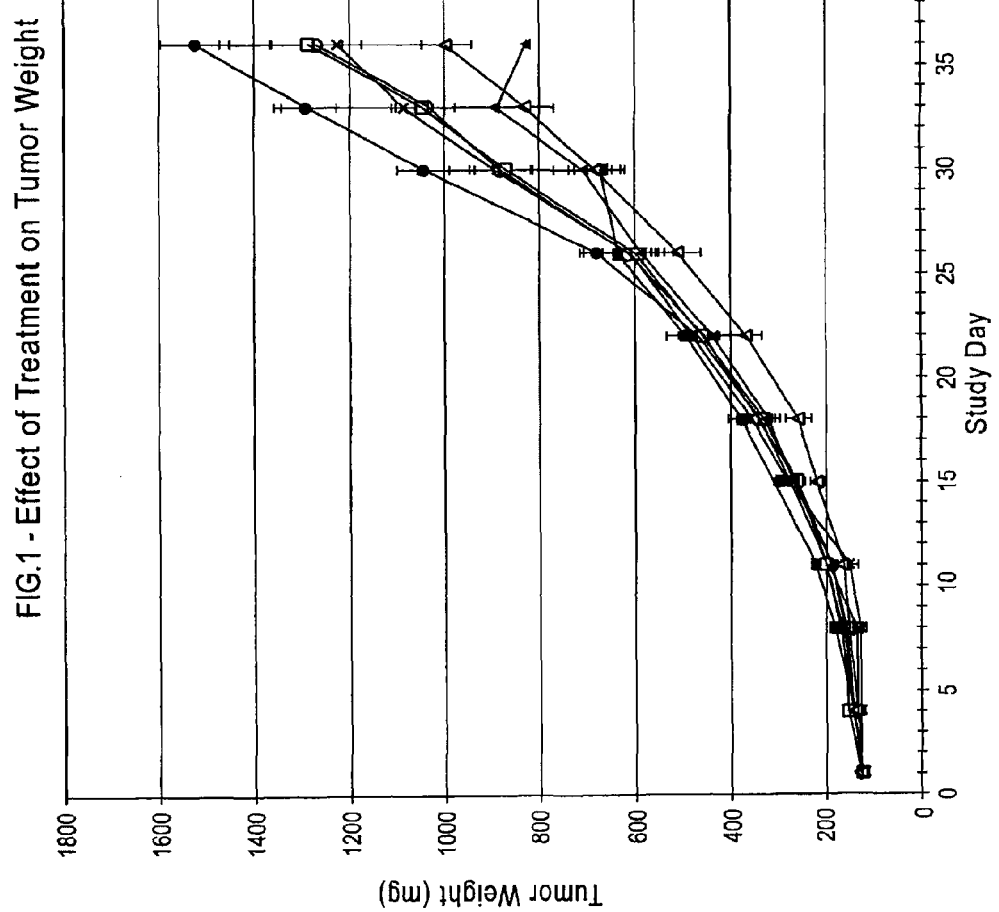

Chen et al., 2011 "Autophagy as a therapeutic target in cancer," *Cancer Biol Ther*. 11(2):157-168.
Crawford et al., 2003 "Chemotherapy-Induced Neutropenia," *Cancer* 100(2):228-237.
Ellerman et al., 2007 "Masquerader: High Mobility Group Box-1 and Cancer," *Clin Cancer Res*. 15;13(10):2836-48.
Fabris et al., 2000 "Pathophysiology of Heparin-Induced Thrombocytopenia," *Arch Pathol Lab Med* 124:1657-1666.
Friese, 2006 "Chemotherapy-Induced Neutropenia: Important New Data to Guide Nursing Assessment and Management," *Advanced Studies in Nursing* 4(2):21-25.
Fryer et al., 1997 "Selective O-Desulfation Produces Nonanticoagulant Heparin that Retains Pharmacological Activity in the Lung," *JPET* 282(1):208-219.
Ghosn et al., 2007 "FOLFOX-6 combination as the first-line treatment of locally advanced and/or metastatic pancreatic cancer," *Am J Clin Oncol*., 30(1):15-20.
Greinacher et al., 1995 "Characterization of the Structural Requirements for a Carbohydrate Based Anticoagulant With a Reduced Risk of Inducing the Immunological Type of Heparin-Associated Thrombocytopenia," *Thrombosis and Haemostasis* 74( 3):886-892.
Guidance for Industry, 2009 "Animal Models—Essential Elements to Address Efficacy Under the Animal Rule".
Haas et al., 1999 "Heparin-induced Thrombocytopenia: Clinical Considerations of Alternative Anticoagulation with Various Glycosaminoglycans and Thrombin Inhibitors," *Clin Appl Thrombosis/Hemostasis* 5:52-59.
Jeske et al., 1999 "Heparin-Induced Thrombocytopenic Potential of GAG and Non-GAG-Based Antithrombotic Agents," *Clin Appl Thrombosis/Hemostasis* 5:S56-S62.
Kang et al., 2011 "The Receptor for Advanced Glycation End-Products (RAGE) Protects Pancreatic Tumor Cells Against Oxidative Injury," *Antioxid & Redox Signal*., 15(8):2175-2184.
Kang et al., 2011 "Apoptosis to autophagy switch triggered by the MHC class III-encoded receptor for advanced glycation endproducts (RAGE)," *Autophagy*, 7(1):91-93.
Kang et al., 2010 "The receptor for advanced glycation end products (RAGE) sustains autophagy and limits apoptosis, promoting pancreatic tumor cell survival," *Cell Death and Differentiation*, 17:666-676.
Kang et al., 2010 "HMGB1 A novel Beclin 1-binding protein active in autophagy," *Autophagy*, 6(8):1209-1211.
Lambert et al., 2007 "Platelet factor 4 is a negative autocrine in vivo regulator of megakaryopoiesis: clinical and therapeutic implications," *Blood*, 110(4):1153-1160.
Lambert et al., 2011 "The Role of Platelet Factor 4 in Radiation-Induced Thrombocytopenia," *Int. J. Radiation Oncology Biol. Phys*. 80(5):1533-1540.
Lambert et al., 2012 "2-O, 3-O-Desulfated Heparin (ODSH) Mitigates Chemotherapy-Induced Thrombocytopenia (CIT) by Blocking the Negative Paracrine Effect of Platelet Factor 4 (PF4) on Megakaryopoiesis," *Blood* 120:Abstract 386.
Lambert et al., 2012 "Platelet factor 4 platelet levels are inversely correlated with steady-state platelet counts and with platelet transfusion needs in pediatric leukemia patents," *International Society on Thrombosis and Haemostasis* 10(7):1442-1446.
Lapierre et al., 1996 "Chemical modifications of heparin that diminish its anticoagulant but preserve its heparanase-inhibitory, angiostatic, anti-tumor and anti-metastatic properties," *Glycobiology* 6(3):355-366.
Liu et al., 2010 "Autophagy: A Potential Mechanism for Resistance of Esophageal Squamous Cell Carcinoma to Therapy," *J Formos Med Assoc*., 109(11):775-776.
Liu et al., 2011 "Inhibition of autophagy by 3-MA potentiates cisplatin-induced apoptosis in esophageal squamous cell carcinoma cells," *Med Oncol*., 28:105-111.
Liu et al., 2011 "DAMP-mediated autophagy contributes to drug resistance," *Autophagy*, 7(1):112-114.
Lorenz et al., 1988 "Platelet Factor 4 (PF 4) in Septicaemia," *Infection* 16(5):273-6.
Ludwig, 2009 "Therapeutic Use of Heparin beyond Anticoagulation," *Current Drug Discovery Technologies* 6:281-289.
Marcus et al., 2012 ODSH, a heparin derivative, enhances the efficacy of gemcitabine in a refractory human pancreatic tumor xenograph model, AACR Annual Meeting, Abstract 3698.
Merchant et al., 1985 "Structure of heparin-derived tetrasaccharides," *Biochem. J*. 229:369-377.
Messmore et al., 2003 "Benefit-Risk Assessment of Treatments for Heparin-Induced Thrombocytopenia," *Drug Safety 2003* 26(9):625-641.
Mulloy et al., 2000 Conformation and dynamics of heparin and heparan sulfate, *Glycobiology* 10(11):1147-1156.
Peterson et al., 2012 "VEGF, PF4 and PDGF are elevated in platelets of colorectal cancer patients," *Angiogenesis* 15:265-273.
Poruk et al., 2010 "Serum Platelet Factor 4 is an Independent Predictor of Survival of Venous Thromboembolism in Patients with Pancreatic Adenocarcinoma," *Cancer Epidemiol Biomarkers Prev* 19(10):2605-2610.
Rao et al., 2010 "Low anticoagulant heparin targets multiple sites of inflammation, suppresses heparin-induced thrombocytopenia, and inhibits interaction of RAGE with its ligands," *Am J Physiol Cell Physiol* 299:C97-C110.
Shah et al., 2010 "Random assignment multicenter phase II study of modified docetaxel, cisplatin, fluorouracil (mDCF) versus DCF with growth factor support (GCSF) in metastatic gastroesophageal adenocarcinoma (GE)," *J Clin Oncol*, 28(15) Supp:4014.
Sheridan et al., 1986 "A Diagnostic Test for Heparin-Induced Thrombocytopenia," *Blood* 67:27-30.
Sims et al., 2010 "HMGB1 and RAGE in Inflammation and Cancer," *Annu. Rev. Immunol*., 28:367-388.
Sparvero et al., 2009 "RAGE (Receptor for Advanced Glycation Endproducts), RAGE Ligands, and their role in Cancer and Inflammation," *J Transl Med*, 7:17.
Stringer et al., 1997 "Specific Binding of the Chemokine Platelet Factor 4 to Heparan Sulfate," *The Journal of Biological Chemistry* 272(33):20508-20514.
Tang et al., 2011 "High-Mobility Group Box 1, Oxidative Stress, and Disease," *Antioxid & Redox Signal*., 14(7):1315-1335.
Tang et al., 2010 "Endogenous HMGB1 regulates autophagy," *J Cell Biol*., 190(5):881-892.
Tang et al., 2010 "High-mobility Group Box 1 [HMGB1] and Cancer," *Biochim Biophys Acta*., 1799(1-2): 131.
Tang et al., 2010 "The redox protein HMGB1 regulates cell death and survival in cancer treatment," *Autophagy*, 6(8):1181-1183.
Tani et al., 2010 "Abstract 4175: Anticancer effects of heparin in the experimental metastasis of the pancreatic cancer model with enhanced potency of gemcitabine," *Cancer Research*, 70(8), Supp. 1.
Thourani et al., 2000 "Nonanticoagulant heparin inhibits NF-κB activation and attenuates myocardial reperfusion injury," *Am J Physiol Heart Circ Physiol* 48:H2084-H2093.
Van Doormaal et al., 2011 "Randomized Trial of the Effect of the Low Molecular Weight Heparin Nadroparin on Survival in Patients With Cancer," *J Clin Oncol*, vol. 29, No. 15:2071-2076.
Von Hoff et al., 2011 "Gemcitabine Plus *nab*-paclitaxel is an Active Regimen in Patients With Advanced Pancreatic Cancer: A Phase I/II Trial," *J Clin Oncol*, 29(34):4548-4554.
Walenga et al., 1996 "Relative Heparin-Induced Thrombocytopenic Potential of Low Molecular Weight Heparins and New Antithrombotic Agents," *Clin Appl Thrombosis/Hemostasis* 2(Suppl. 1):S21-S27.
Walenga et al., 1997 "Biochemical and Pharmacologic Rationale for the Development of a Synthetic Heparin Pentasaccharide," *Thrombosis Research* 86(1):1-36.
Walenga et al., 1999 "Vascular Damage Correlates Between Heparin-Induced Thrombocytopenia and the Antiphospholipid Syndrome," *Clin Appl Thrombosis/Hemostasis* 5(Suppl. 1): S76-S84.
Walenga et al., 2000 "Mechanisms of Venous and Arterial Thrombosis in Heparin-Induced Thrombocytopenia," *Journal of Thrombosis and Thrombolysis* 10:S13-S20.

(56) References Cited

OTHER PUBLICATIONS

Walenga et al., 2002 "Fondaparinux: a synthetic heparin pentasaccharide as a new antithrombotic agent," *Expert Opin. Investig. Drugs* 11(3):397-407.

Walenga et al., 2003 "Heparin-induced thrombocytopenia, paradoxical thromboembolism, and other adverse effects of heparin-type therapy," *Hematology/Oncology Clinics of North America* 17:259-282.

Walenga et al., 2004 "Decreased Prevalance of Heparin-Induced Thrombocytopenia with Low-Molecular-Weight Heparin and Related Drugs," *Seminars in Thrombosis and Hemostasis* 30(Suppl. 1):69-80.

Walenga et al., 2004 "Newer Insights on the Mechanism of Heparin-Induced Thrombocytopenia," *Seminars in Thrombosis and Hemostasis* 30(Suppl. 1):57-67.

Yang et al., 2011 "Pancreatic cancers require autophagy for tumor growth," *Genes & Dev.*, 25:717-729.

Ye et al., 2010 "Platelet-derived growth factor enhances platelet recovery in a murine model of radiation-induced thrombocytopenia and reduces apoptosis in megakaryocytes via its receptors and the PI3-k/Akt pathway," *haematologica* 95(1):1745-1753.

PCT Invitation to Pay Additional Fees and, Where Applicable, Protest Fee from PCT/US2013/31053 dated May 10, 2013.

Krauel et al., 2008 "Heparin-induced thrombocytopenia—therapeutic concentrations of danaparoid, unlike fondaparinux and direct thrombin inhibitors, inhibit formation of platelet factor 4-heparin complexes," *Journal of Thrombosis and Haemostasis* 6:2160-2167.

PCT International Preliminary Report on Patentability from PCT/US13/31053 dated Nov. 11, 2014.

Cardenes, H. R., et al., "Locally Advanced Pancreatic Cancer: Current Therapeutic Approach," *The Oncologist*, 2006, pp. 612-623, vol. 11.

Cooper, B. W., et al., "A Phase I and Pharmacodynamic Study of Fludarabine, Carboplatin, and Topotecan in Patients With Relapsed, Refractory, or High-Risk Acute Leukemia," *Clin Cancer Res*, 2004, pp. 6830-6839, vol. 10.

Croghan, G. A., et al., "A Study of Paclitaxel, Carboplatin, and Bortezomib in the Treatment of Metastatic Malignant Melanoma," *Cancer*, 2010, pp. 3463-3468, vol. 116.

Deutsch, M. A., et al., "Carboplatin, etoposide, and radiotherapy, followed by surgery, for the treatment of marginally resectable non-small cell lung cancer," *Cancer Treat Rev.*, 1993, vol. 19, Suppl C (Abstract).

Gulec, S. A., et al., "Treatment of Advanced Pancreatic Carcinoma with 90 Y-Clivatuzumab Tetraxetan: A Phase I Single-Dose Escalation Trial," *Clin Cancer Res*, 2011, pp. 4091-4100, vol. 17.

Ishii, H., et al., "Phase II Study of Gemcitabine Chemotherapy Alone for Locally Advanced Pancreatic Carcinoma: JCOG0506," *Jpn J Clin Oncol*, 2010, pp. 573-579, vol. 40(6).

Kantarjian, H. M., et al., "High doses of cyclophosphamide, etoposide and total body irradiation followed by autologous stem cell transplantation in the management of patients with chronic myelogenous leukemia," *Bone Marrow Transplant*, 1994, vol. 14(1) (Abstract).

Van Deventer, H. W., et al., "Clinical Course of Thrombocytopenia in Patients Treated With Imatinib Mesylate for Accelerated Phase Chronic Myelogenous Leukemia," *Am. J. Hem.*, 2002, pp. 184-190, vol. 71.

European Patent Office, Extended European Search Report for European Patent Application No. 13787651.2, Nov. 27, 2015, 12 Pages.

Intellectual Property Office of Singapore, Search Report and Written Opinion for Singapore Patent Application No. 11201407340Y, Nov. 18, 2015, 13 Pages.

Casu, B. et al., "Non-Anticoagulant Heparins and Inhibition of Cancer," Pathophysiology of Haemostasis and Thrombosis, 2007, pp. 195-203, vol. 36.

Gao, C., et al., "Chemically modified heparin inhibits the in vitro adhesion of nonsmall cell lung cancer cells to P-selectin," Journal of Cancer Research and Clinical Oncology, 2006, pp. 257-264, vol. 132, No. 4.

Rivera, G. K., et al., "Effectiveness of Intensified Rotational Combination Chemotherapy for Late Hematologic Relapse of Childhood Acute Lymphoblastic Leukemia," Blood, 1996, pp. 831-837, vol. 88, No. 3.

Sigal, D., et al., "2-O, 3-O Desulfated Heparin (ODSH) May Mitigate Chemotherapy-Induced Thrombocytopenia and Neutropenia in Patients Treated with Combination Gemcitabine (G)/Nab-Paclitaxel (A), a Myelosuppressive Chemotherapy Regimen," BLOOD, 2012, p. 4723 (Abstract), vol. 120, No. 21.

Wang, Y., et al., "Heparin-Paclitaxel Conjugates as Drug Delivery System: Synthesis, Self-Assembly Property, Drug Release, and Antitumor Activity," Bioconjug. Chem., 2009, pp. 2214-2221, vol. 20, No. 12.

\* cited by examiner

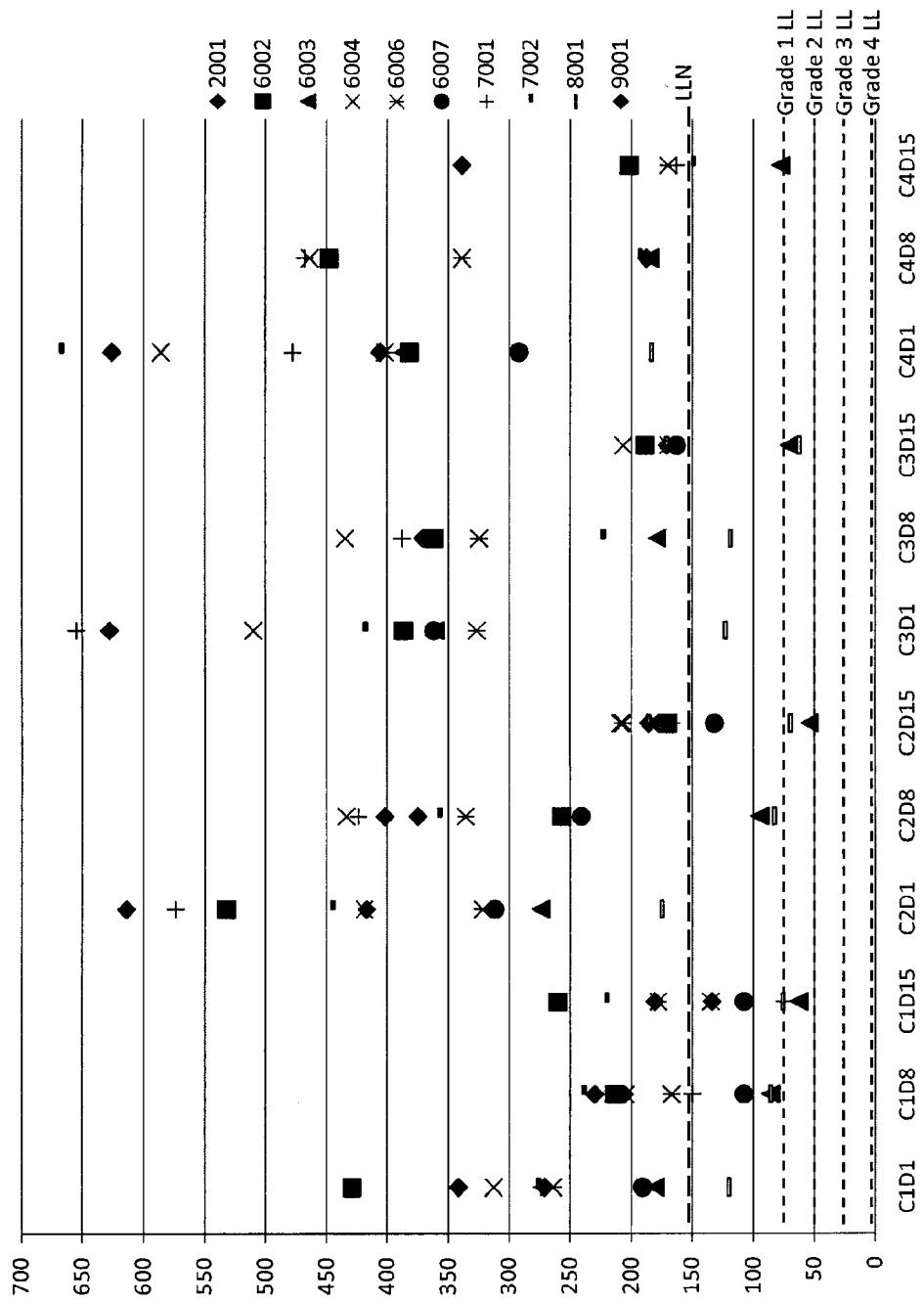

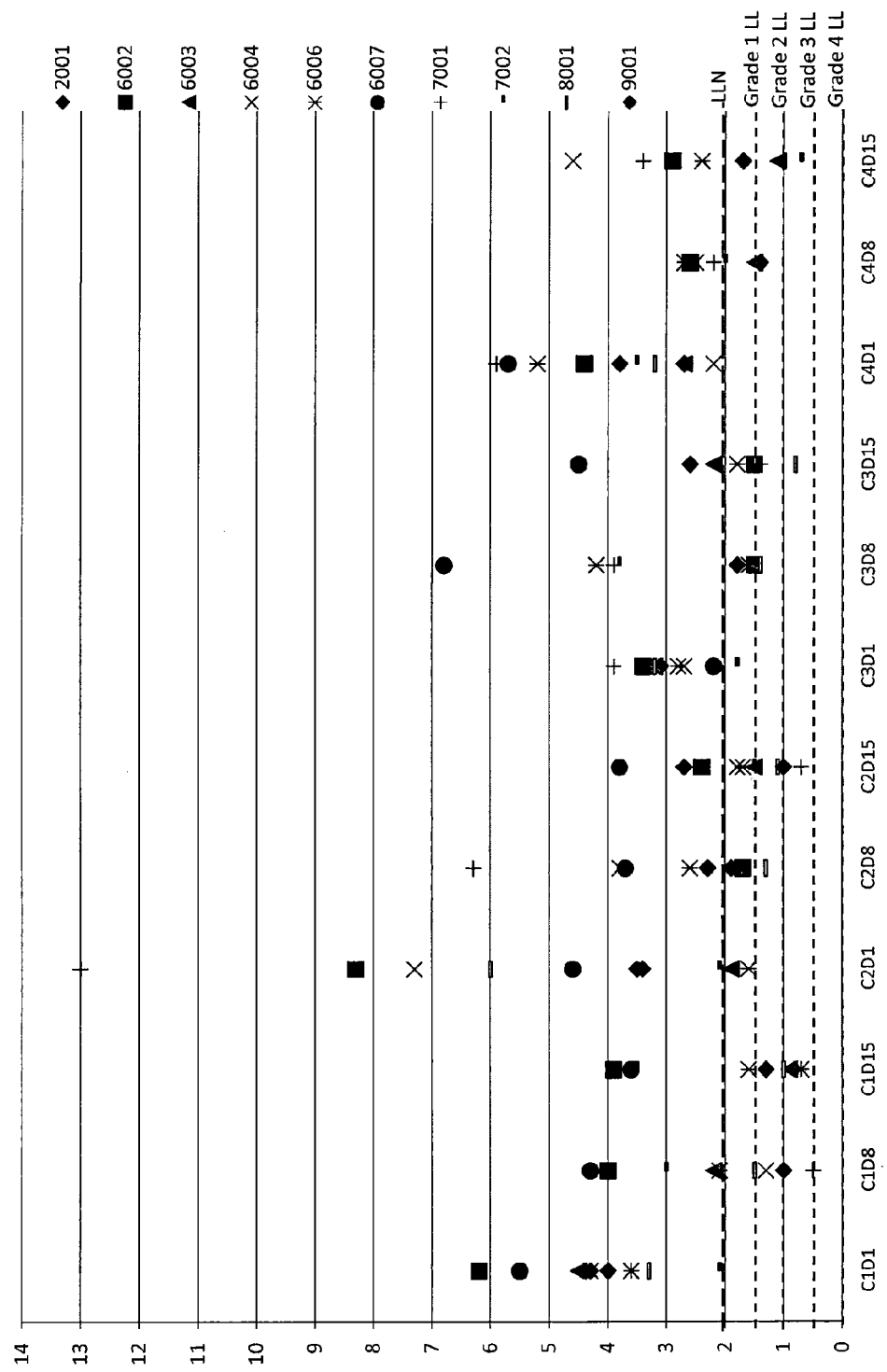

FIG. 10A – Mean and Median Platelet Count

|  | Screen | Cycle 1 ||| Cycle 2 ||| Cycle 3 |||
| --- | --- | --- | --- | --- | --- | --- | --- | --- | --- | --- |
|  |  | Day 1 | Day 8 | Day 15 | Day 1 | Day 8 | Day 15 | Day 1 | Day 8 | Day 15 |
| Mean | 274,000 | 266,000 | 169,000 | 143,000 | 408,000 | 300,000 | 156,000 | 419,000 | 307,000 | 155,000 |
| Median | 268,000 | 273,000 | 186,000 | 135,000 | 418,000 | 347,000 | 174,000 | 387,000 | 362,000 | 171,000 |

FIG. 10B – Mean and Median Neutrophil Count

|  | Screen | Cycle 1 ||| Cycle 2 ||| Cycle 3 |||
|---|---|---|---|---|---|---|---|---|---|---|
|  |  | Day 1 | Day 8 | Day 15 | Day 1 | Day 8 | Day 15 | Day 1 | Day 8 | Day 15 |
| Mean | 5800 | 4100 | 2200 | 1900 | 5200 | 2900 | 1800 | 2900 | 2900 | 2000 |
| Median | 5500 | 4200 | 2100 | 1300 | 4100 | 2500 | 1600 | 3100 | 1800 | 1500 |

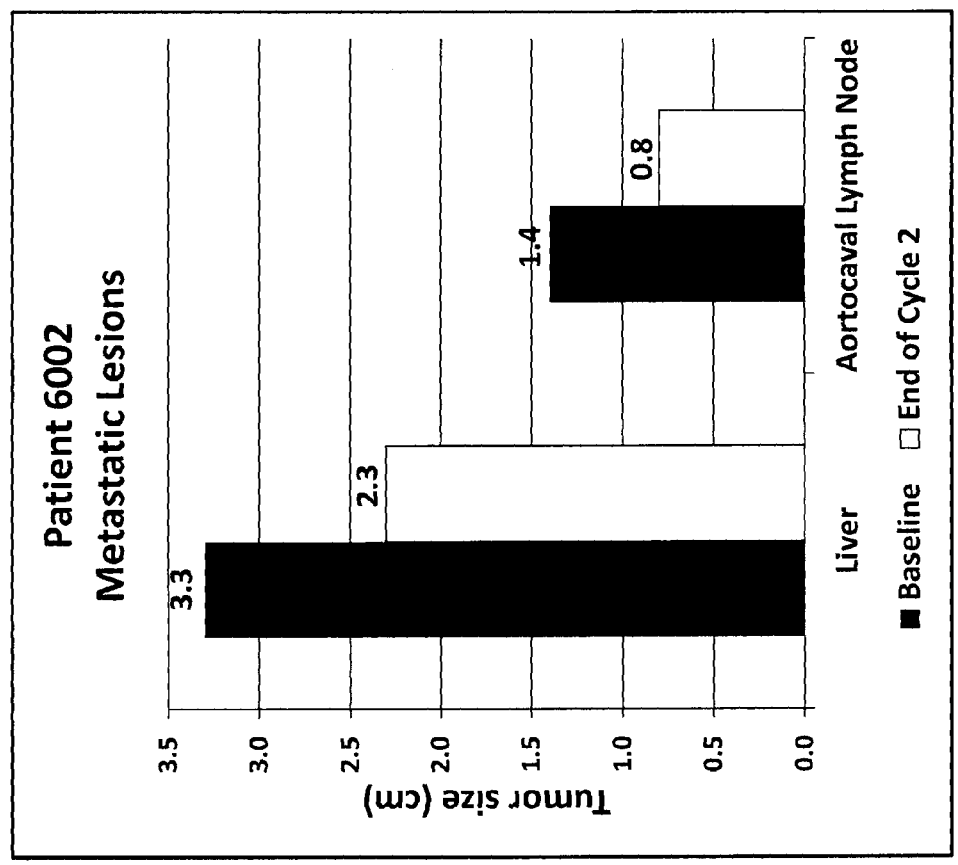

FIG. 12A

| Patient number | Sites of metastatic disease | CA 19-9 (Baseline) | CA 19-9 (Cycle 4, Day 1) | RECIST Criteria Tumor Response and Patient Status |
|---|---|---|---|---|
| 2001 | Liver, both lungs | 4,775 | 9,926 | Stable disease; liver and lung metastases reduced in size; on study |
| 6002 | Liver, aortocaval and hilar nodes | 125 | 15 | Stable disease; liver and nodal metastases reduced in size; on study |
| 6003 | Both lungs | 6,186 | 2,405 | Stable disease; on study |
| 6004 | Periaortic and gastric nodes; unresectable pancreatic mass | 6,275 | 348 | Partial response; on study |
| 6006 | Multiple liver metastases | 395 | 108 | Stable disease; on study |
| 6007 | Liver, left and right adrenals, unresectable pancreatic mass | 70,086 | 10,286* | Partial response; on study |
| 7001 | Porta hepatis, supraclavicular nodes with unresectable pancreatic mass | 2,138 | 288 | Partial response; on study |
| 7002 | "Dozens" of liver metastases | 483 | 80 | Partial response; on study |
| 8001 | Periaortic and mesenteric nodes and unresectable pancreatic mass | 11 | 20 | Stable disease; on study |
| 9001 | Liver, lung, unresectable pancreatic mass | 326 | 69 | Partial response; on study |

*CA19-9 at Cycle 3, Day 1

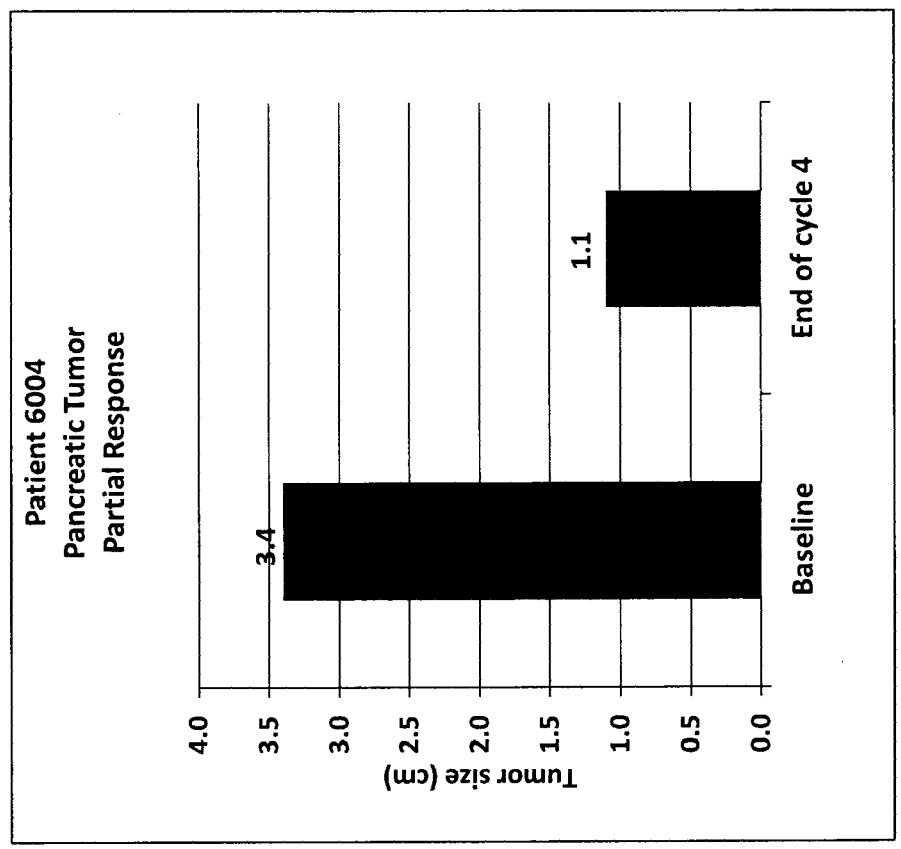

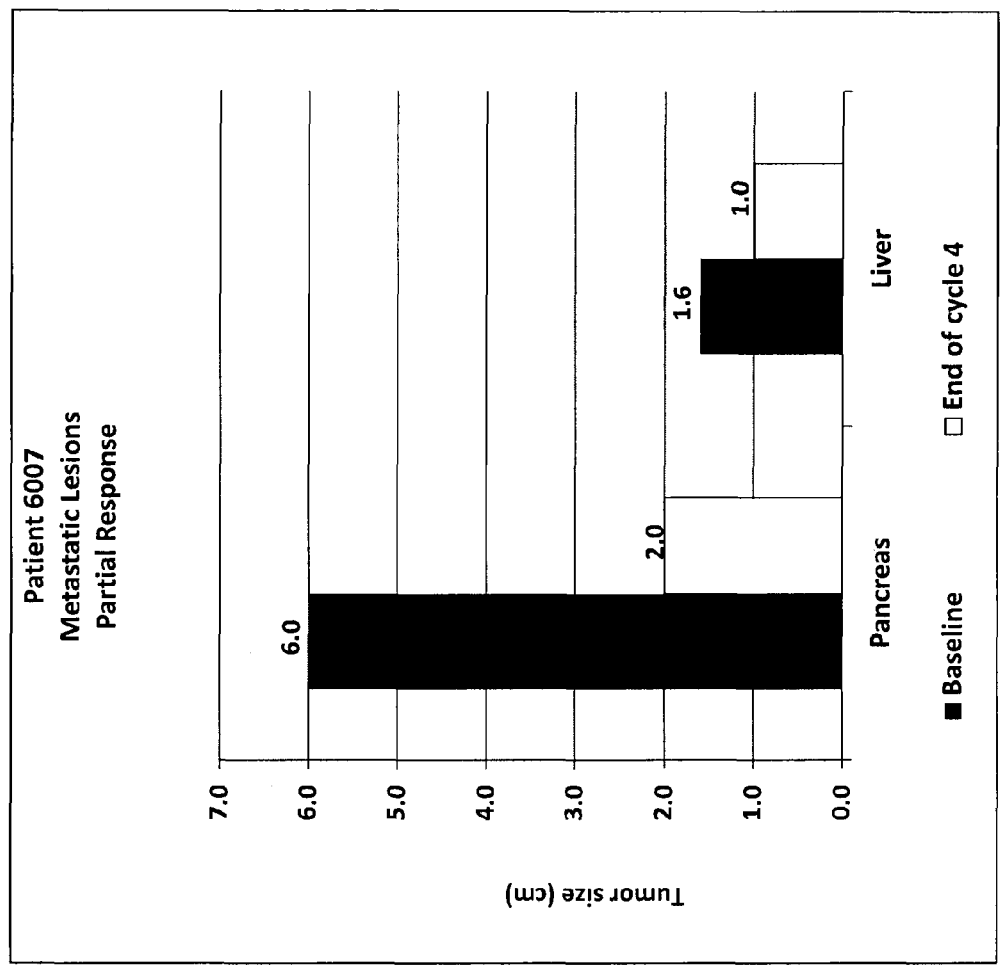

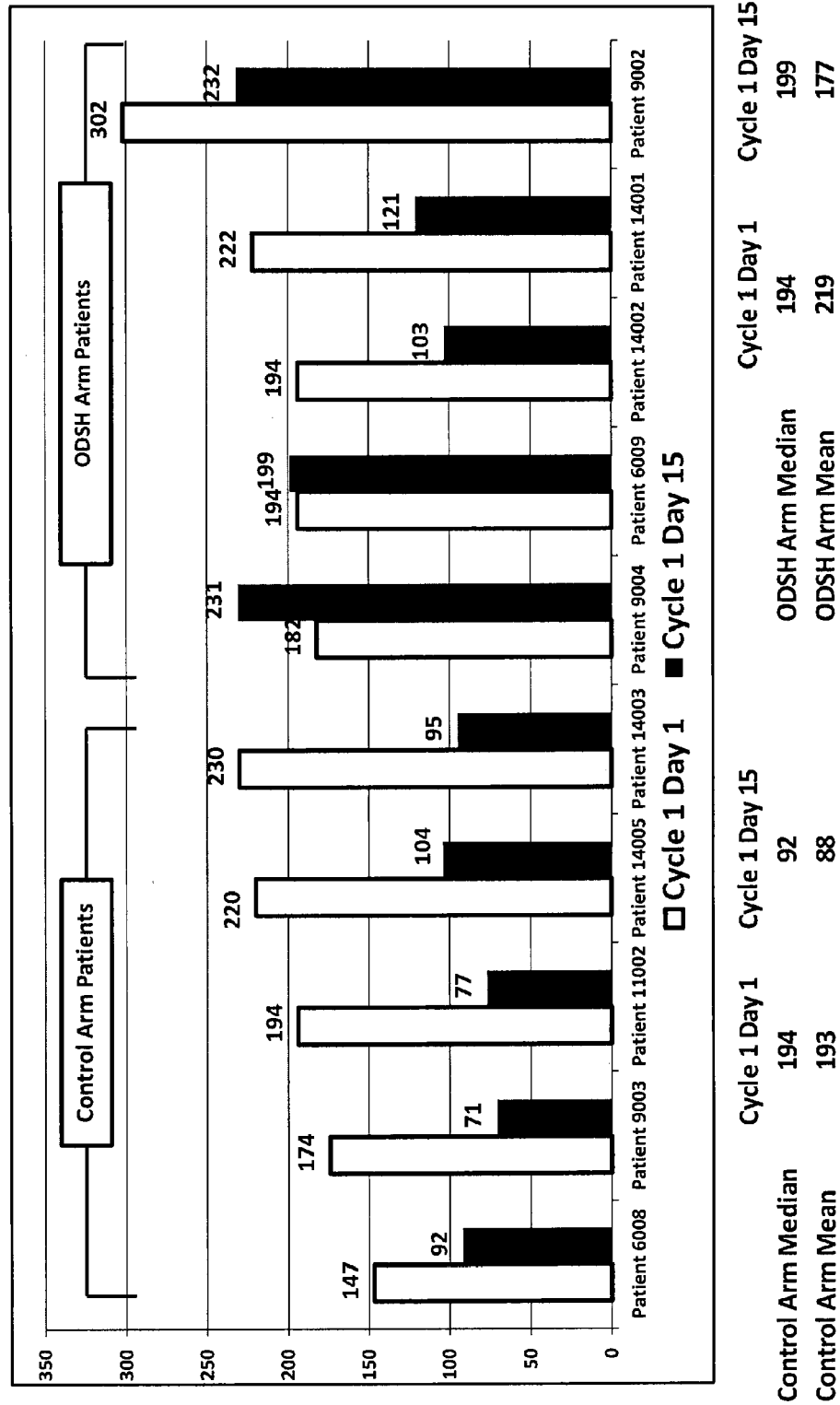

Platelet count (X 10³/μl blood)

TREATMENT OF MYELOSUPPRESSION

1. CROSS-REFERENCE TO RELATED APPLICATIONS

This application claims the benefit under 35 U.S.C. §119(e) of U.S. Provisional Application Nos. 61/724,836, filed Nov. 9, 2012; 61/702,207, filed Sep. 17, 2012; 61/678,053, filed Jul. 31, 2012; 61/668,709, filed Jul. 6, 2012; 61/664,611, filed Jun. 26, 2012; 61/653,362, filed May 30, 2012; 61/648,043, filed May 16, 2012; 61/644,623, filed May 9, 2012; and 61/644,556, filed May 9, 2012, the contents of all of which are incorporated herein in their entireties by reference thereto.

2. BACKGROUND

Platelets play a critical role in the blood clotting mechanism. Depletion of platelets below a certain level results in thrombocytopenia, which can be triggered by a number of clinical conditions and disorders and can range from mild to life-threatening.

Thombocytopenia can be triggered by diseases and conditions affecting the bone marrow, where platelet precursors arise before entering the bloodstream; by diseases and conditions affecting the liver, which produces thrombopoietin, the hormone that stimulates the production of platelets; by sequestration of platelets; by increased destruction of platelets; and by a variety of other causes. In particular, thrombocytopenia is a common side effect of certain treatment regimens, such as cancer treatment regimens involving antineoplastic agents. Chemotherapy-induced or radiation-induced thrombocytopenia can result in delays in treatment and/or compel reductions in treatment dose, which in turn can result in reduced efficacy of the treatment.

Because severe thrombocytopenia puts a patient at risk of uncontrolled hemorrhage, development of safe and effective treatments for thrombocytopenia is highly desirable. In spite of the clear need for such treatments, however, very few such treatments exist. Attempts to develop a recombinant form of human thrombopoietin have proved unsuccessful. While a recombinant human thrombopoietin showed early promise, it showed a tendency to induce the development of auto-antibodies when tested in patients. Currently, standard therapy of thrombocytopenia, such as immune-mediated thrombocytopenia, can include treatment with corticosteroids, rituximab, and/or thrombopoietin receptor agonists, splenectomy, and platelet transfusions. However, each has drawbacks, including incomplete response, development of side effects to treatment, and risks attendant to any form of surgery. For chemotherapy-induced thrombocytopenia, only one therapeutic agent, interleukin-11, has proven sufficiently effective to merit regulatory approval, but is rarely prescribed by physicians because of the severity of its side effects. For radiation-induced thrombocytopenia, there is no approved therapeutic agent that attenuates the thrombocytopenia. Thus, there remains a significant need for agents that attenuate thrombocytopenias of varying etiology, including immune-mediated thrombocytopenias, drug-induced thrombocytopenias, especially chemotherapy-induced thrombocytopenia, and radiation-induced thrombocytopenia.

Neutrophils, also called polymorphonuclear leukocytes, are the most numerous of the blood cells known as granulocytes. Neutrophils, like other blood cells, are produced by the bone marrow. Neutrophils are an important component of natural immunity. When neutrophil levels fall below normal, a condition called neutropenia occurs, increasing the risk of infection. Neutropenia can arise from a number of different causes, ranging from congenital defects to viral infections, but a context in which neutropenia frequently occurs is as a side effect of a treatment regimen. Neutropenia is a common side effect in patients being treated for cancer with antineoplastic agents, putting patients at risk of developing serious and even life-threatening infections, and forcing delays in treatment and/or compelling reduction in treatment dose, resulting in reduced efficacy.

A variety of agents and therapies have been tested to combat neutropenia, with varying degrees of success. Administration of glucocorticoids, androgenic steroids, and vitamins to stimulate bone marrow to produce more neutrophils has not proved successful. At present, only two agents—granulocyte colony-stimulating factor (G-CSF) and granulocyte-macrophage colony-stimulating factor (GM-CSF)—are widely used to treat patients with severe neutropenia, most often after intensive cancer chemotherapy and/or bone marrow transplantation. These agents exhibit adverse effects such as bone pain, abnormalities of liver dysfunctions and pleural and pericardial effusions. Thus, there is a need for compounds that are safe and effective for treating neutropenia and promoting neutrophil production.

3. SUMMARY

In a first aspect, methods are provided for attenuating a myelosuppressive side effect of a patient treatment regimen. The methods comprise adjunctively administering to the patient a therapeutically effective amount of a platelet factor 4-interacting heparinoid (hereinafter "PF4-interacting heparinoid"). As provided herein, a myelosuppressive side effect is the occurrence of thrombocytopenia and/or neutropenia, and a patient treatment regimen having a myelosuppressive side effect is a treatment regimen that induces, as a side effect, one or both of thrombocytopenia and neutropenia. In various embodiments, this aspect provides uses of a PF4-interacting heparinoid, e.g., ODSH, in the attenuation of a myelosuppressive side effect of a patient treatment regimen.

Numerous patient treatment regimens have myelosuppressive side effects, including antineoplastic treatment regimens, such as chemotherapy and radiation therapy, antibody therapy, including treatment regimens used to treat cancer and/or auto-immune diseases, and transplant procedures, such as bone marrow or stem cell transplant. In certain embodiments, the patient treatment regimen comprises chemotherapy and/or radiation therapy and/or antibody therapy. In an exemplary embodiment, the patient treatment regimen is a chemotherapeutic regimen comprising gemcitabine and nab-paclitaxel. In an exemplary embodiment, the patient treatment regimen is a chemotherapeutic regimen comprising ifosfamide, carboplatin, and etoposide, optionally including rituximab. In certain embodiments, the patient treatment regimen comprises one or more regimens suitable for the treatment of subjects diagnosed with acute myelogenous or myeloid leukemia ("AML"). In an exemplary embodiment, a regimen suitable for the treatment of subjects diagnosed with AML comprises a chemotherapy regimen suitable for inducing remission of AML (known in the art as induction chemotherapy), a chemotherapy regimen for preventing remission of AML (known in the art as consolidation chemotherapy), or both induction and consolidation chemotherapy. Optionally, a regimen suitable for the treatment of subjects diagnosed with AML can also comprise one or more non-chemotherapy-based regimens for preventing remission of AML, which can be used instead of or in combination with consolidation chemotherapy. These non-chemotherapy-based regimens include stem cell transplant, such as allogeneic stem cell transplant, and immunotherapy. Further patient treatment regimens are described in Section 5.1.1.

In various embodiments, the methods are useful for treating subjects diagnosed with cancer, for example pancreatic cancer, solid tumors including osteosarcoma, neuroblastoma, or AML. The subject being treated can be an adult or a pediatric patient. In some embodiments, the subject is diagnosed with a cancer in which PF4 levels are elevated either in platelets or in blood (referred to hereinafter as "PF4-positive cancer"). Examples of PF4-positive cancers include pancreatic cancer and colorectal cancer. Further suitable subjects are described in Section 5.1.2.

In some embodiments, the methods may further comprise adjunctive administration of one or more additional agent or therapy that is pro-thrombopoietic, anti-thrombocytopenic, anti-neutropenic, pro-granulopoietic, and/or anticoagulant. Suitable agents and therapies for further adjunctive administration are described herein at Section 5.1.3. In some embodiments, two or more agents and/or therapies are administered. The two or more agents can have the same activity (e.g., anti-thrombocytopenic), different activity (e.g., a first agent is pro-thrombopoietic and a second agent is anti-neutropenic), or overlapping activity (e.g., a first agent is pro-granulopoietic and anticoagulant and a second agent is anti-coagulant).

The PF4-interacting heparinoid, and any adjunctively administered additional agent(s) or therapy, can be administered concurrently, sequentially, or separately from administration of the patient treatment regimen. Suitable routes and modes of administration are provided below in Section 5.8.

In a second aspect, methods are provided for promoting thrombopoiesis in a subject. The methods comprise administering an effective amount of a PF4-interacting heparinoid to the subject. The subject can be thrombocytopenic or non-thrombocytopenic, as described below in Section 5.2. In various embodiments, the methods comprise treating myelosuppression caused by a disease or condition that reduces platelet count in a subject. In an exemplary embodiment, the subject is diagnosed with systemic inflammatory response syndrome (SIRS), sepsis, or septicemia. Optionally, the subject has elevated serum or plasma level of PF4. In some embodiments, the methods further comprise adjunctive administration of one or more additional agent or therapy that is pro-thrombopoietic, anti-thrombocytopenic, anti-neutropenic, pro-granulopoietic, and/or anticoagulant. Suitable agents and therapies for further adjunctive administration are described herein at Section 5.2.1.

In a third aspect, methods are provided for promoting neutrophil production in a subject. The methods comprise administering an effective amount of a PF4-interacting heparinoid to the subject. The subject can be neutropenic or non-neutropenic, as described below in Section 5.3. In various embodiments, the methods comprise treating myelosuppression caused by a disease or condition that reduces neutrophil count in a subject. Optionally, the subject has elevated serum or plasma level of PF4. In some embodiments, the methods further comprise adjunctive administration of one or more additional agent or therapy that is pro-thrombopoietic, anti-thrombocytopenic, anti-neutropenic, pro-granulopoietic, and/or anticoagulant. Suitable agents and therapies for further adjunctive administration are described herein at Section 5.3.1.

In a fourth aspect, methods are provided for increasing the efficacy of a patient treatment regimen having a myelosuppressive side effect. The methods comprise administering a therapeutically effective amount of a PF4-interacting heparinoid to the subject patient as an adjunct to the patient treatment regimen having a myelosuppressive side effect, without reducing the dose and/or dosage frequency of the patient treatment regimen following a reference treatment administration or treatment cycle.

In some embodiments, the method further comprises administering a dose higher than is typically used for such administration or cycle in the absence of adjunctive administration of a PF4-interacting heparinoid.

In certain embodiments, the methods further comprise determining an initial platelet count in a blood sample from a patient and administering an amount of a PF4-interacting heparinoid effective to raise the patient's platelet count above a threshold level below which therapy with patient treatment regimen having a myelosuppressive side effect is contraindicated. In various embodiments, an amount of a PF4-interacting heparinoid is administered sufficient to maintain platelet levels above levels that indicate grade 3 (severe) or grade 4 (life-threatening) thrombocytopenia. Optionally, the methods can further comprise administering adjunctively to the PF4-interacting heparinoid one or more agents or therapies that is anti-thrombocytopenic, anti-neutropenic, anticoagulant, or has some other therapeutic activity. In some embodiments, the methods comprise a further step of administering a patient treatment regimen having a myelosuppressive side effect to the patient whose platelet count is above a threshold level that contraindicates such therapy. Optionally, the dose amount and/or frequency of the patient treatment regimen can be increased.

In certain embodiments, the methods comprise determining an initial neutrophil count in a blood sample from a patient and administering an amount of a PF4-interacting heparinoid effective to raise the patient's neutrophil count above a threshold level below which therapy with patient treatment regimen having a myelosuppressive side effect is contraindicated. In various embodiments, an amount of a PF4-interacting heparinoid is administered sufficient to maintain neutrophil levels above levels that indicate grade 3 or grade 4 neutropenia, i.e., above about 1000 neutrophils/µl of blood and above about 500 neutrophils/µl of blood, respectively. Optionally, the methods can further comprise administering adjunctively to the PF4-interacting heparinoid one or more agents or therapies that is anti-neutropenic, anti-thrombocytopenic, anticoagulant, or has some other therapeutic activity. In some embodiments, the methods comprise a further step of administering a patient treatment regimen having a myelosuppressive side effect to the patient whose neutrophil count is above a level that contraindicates such therapy. Optionally, the dose amount and/or frequency of the patient treatment regimen can be increased.

The PF4-interacting heparinoids of the present disclosure are heparinoids that are capable of interacting with PF4 and counteracting PF4's ability to suppress production of platelets and neutrophils. PF4-interacting heparinoids bind to PF4 and/or compete with PF4 for binding to progenitor cells in the myeloid cell lineage, e.g., megakaryocytes. Preferably, PF4-interacting heparinoids have an average molecular weight above about 8 kDa, such as an average molecular weight between about 8 kDa and about 15 kDa, more preferably between about 11 kDa and 13 kDa. The PF4-interacting heparinoid is preferably partially desulfated. In some embodiments, the PF4-interacting heparinoid is substantially sulfated at the 6-O and/or the N position. An exemplary PF4-interacting heparinoid, which is suitable for use in the methods described herein, is substantially 2-O, 3-O desulfated, referred to herein as ODSH. See also Section 5.6.

The present disclosure further provides pharmaceutical compositions and unit dosage forms comprising PF4-interacting heparinoids, suitable for use in the methods described herein, either alone or adjunctive to a patient treatment regimen and/or one or more additional agent or therapy. The pharmaceutical compositions may be prepared for parenteral administration, such as intravenous or subcutaneous administration. For intravenous administration, pharmaceutical compositions can be formulated for administration as a bolus or as a continuous infusion.

Pharmaceutical compositions for use in the methods disclosed herein comprise an amount of a PF4-interacting heparinoid, as described below in Section 5.9, sufficient to allow effective doses to be administered.

In some embodiments, pharmaceutical compositions of PF4-interacting heparinoid are suitable for intravenous administration at doses ranging from about 0.1 mg/kg/hr to about 2.5 mg/kg/hr for infusions and from about 1 mg/kg to about 25 mg/kg for bolus doses. In some embodiments, pharmaceutical compositions of PF4-interacting heparinoid are suitable for subcutaneous administration and are formulated for administration at doses ranging from about 25 mg to about 400 mg, in volumes of 2.0 ml or less per injection site.

4. BRIEF DESCRIPTION OF THE FIGURES

FIG. 1 provides a graph illustrating the effect of 8 different treatment regimens on tumor weight in an in vivo murine xenograft model of human pancreatic cancer, as described further in Example 1 and at Table 1: vehicle control (Group 1, ●); ODSH alone (Group 2, ○); oxaliplatin/gemcitabine/nab-paclitaxel (Group 3, ■); gemcitabine alone (Group 4, □); oxaliplatin/gemcitabine/nab-paclitaxel with ODSH (Group 5, ▲); gemcitabine with ODSH (Group 6, ∆); oxaliplatin/gemcitabine (Group 7, x); and oxaliplatin/gemcitabine with ODSH (Group 8, ☆).

Figure 2:
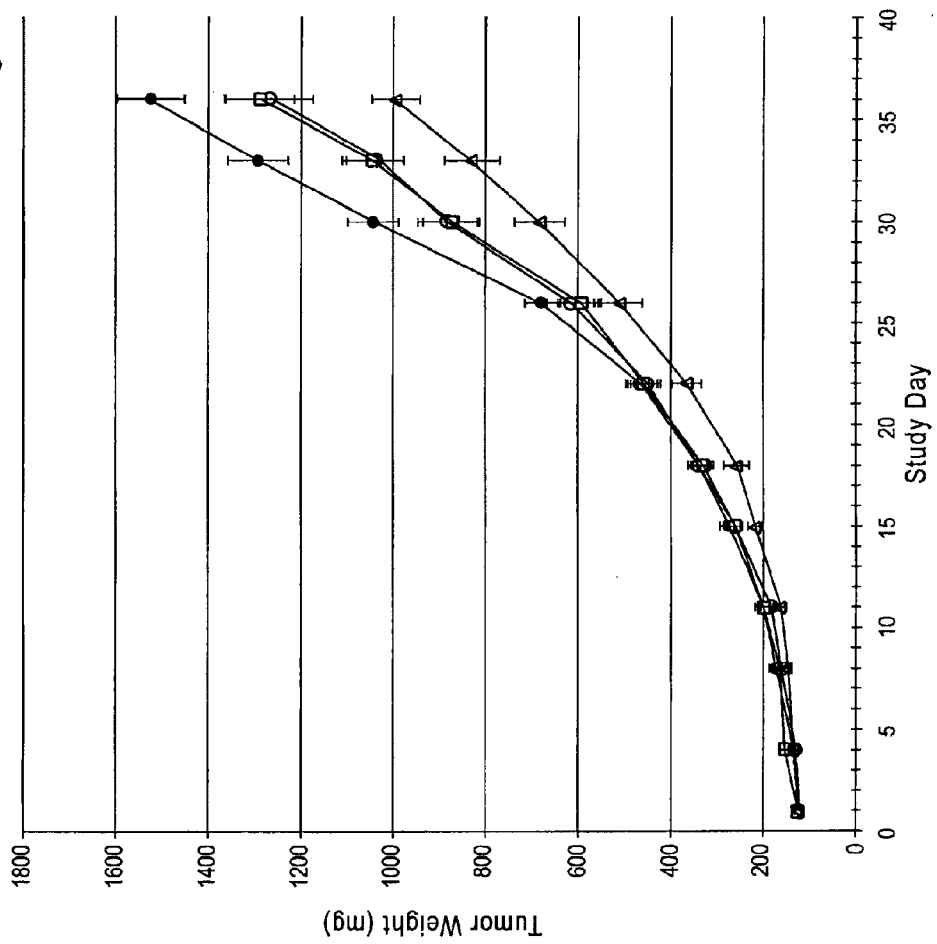

FIG. 2 provides a graph illustrating the effect on tumor weight of a subset of the treatment regimens used in Example 1 and shown in FIG. 1: vehicle control (Group 1, ●); ODSH alone (Group 2, ○); gemcitabine alone (Group 4, □); and gemcitabine with ODSH (Group 6, ∆).

Figure 3:
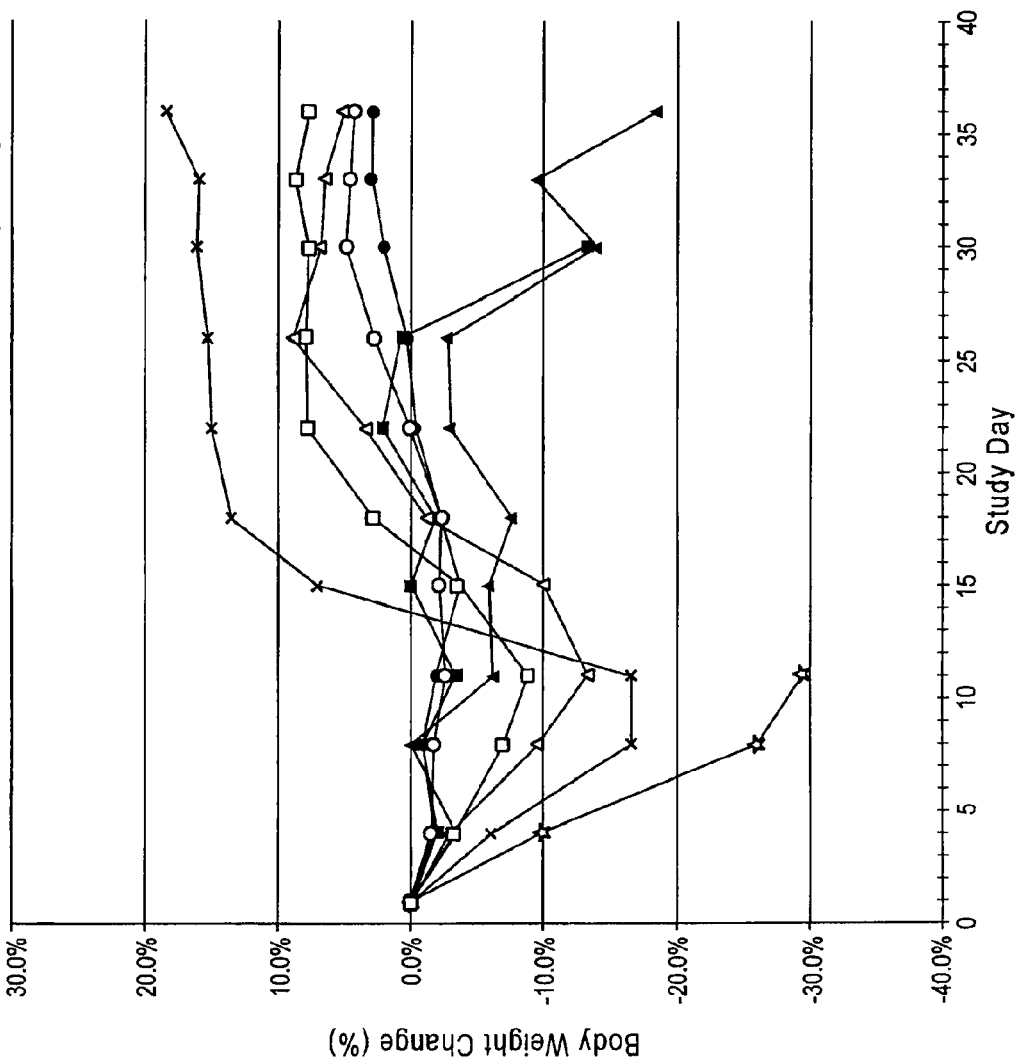

FIG. 3 provides a graph illustrating the effect on body weight of the 8 different regimens used in Example 1: vehicle control (Group 1, ●); ODSH alone (Group 2, ○); oxaliplatin/gemcitabine/nab-paclitaxel (Group 3, ■); gemcitabine alone (Group 4, □); oxaliplatin/gemcitabine/nab-paclitaxel with ODSH (Group 5, ▲); gemcitabine with ODSH (Group 6, ∆); oxaliplatin/gemcitabine (Group 7, x); and oxaliplatin/gemcitabine with ODSH (Group 8, ☆).

Figure 4:
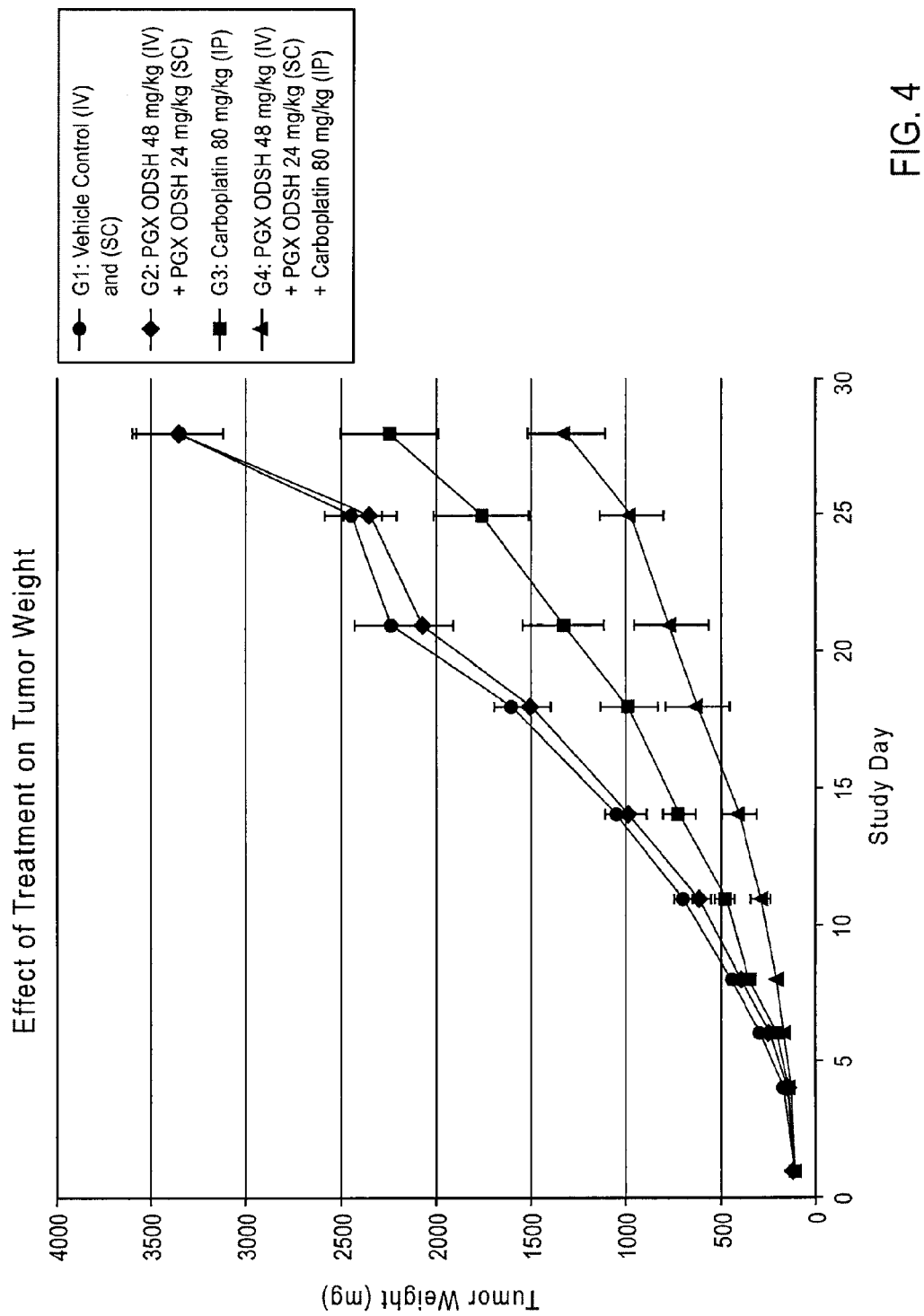

FIG. 4 provides a graph illustrating the effect on tumor weight of 4 different treatment regimens in an in vivo murine xenograft model of human ovarian cancer, as described further in Example 2: vehicle control (Group 1, ●); ODSH alone (Group 2, ♦); carboplatin (Group 3, ■); and carboplatin with ODSH (Group 4, ▲).

Figure 5:
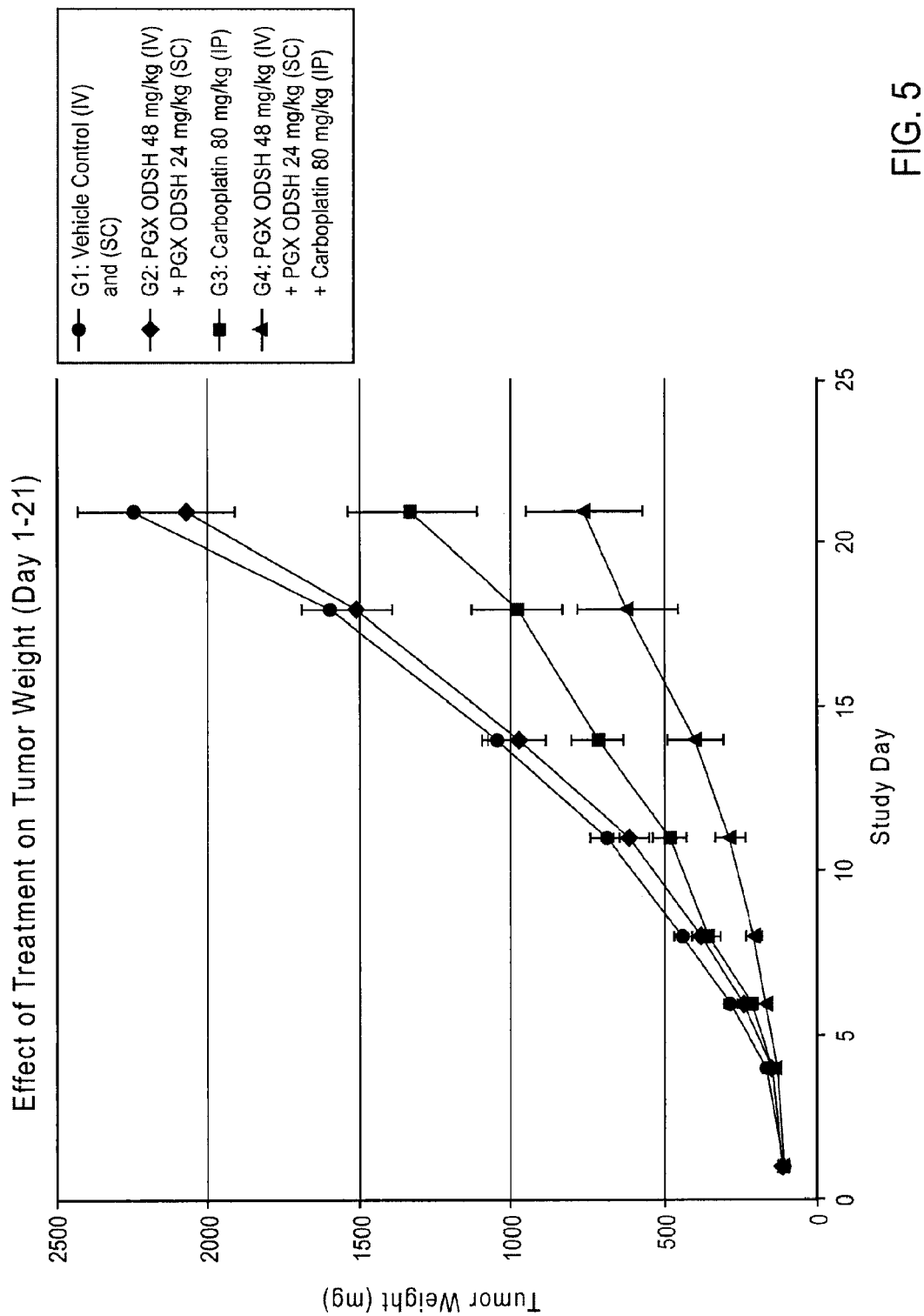

FIG. 5 provides a graph illustrating the effect on tumor weight of the treatment regimens shown in FIG. 4, for days 1-21 of the study.

Figure 6:
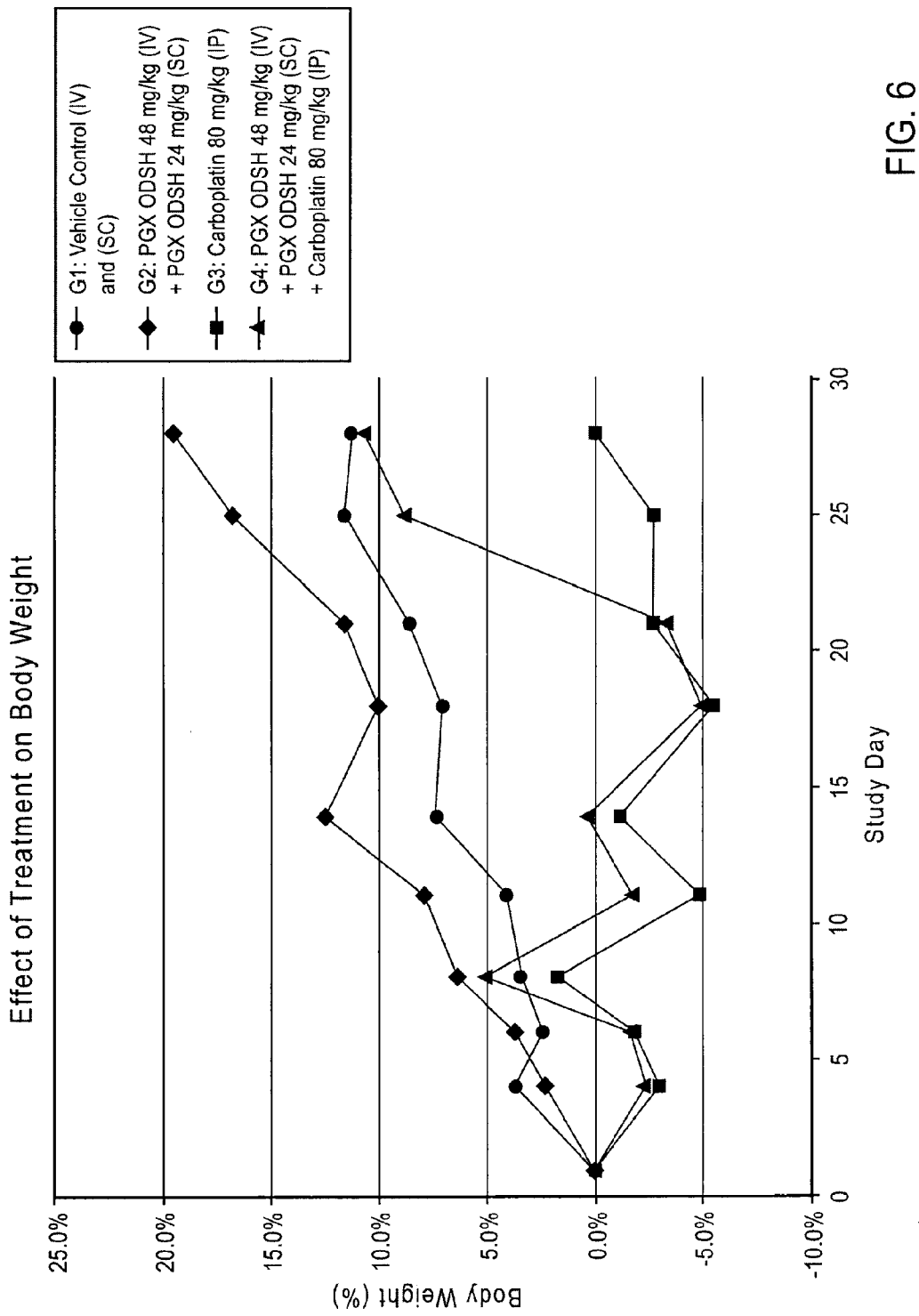

FIG. 6 provides a graph illustrating the effect on mouse body weight of the 4 different regimens used in Example 2: vehicle control (Group 1, ●); ODSH alone (Group 2, ♦); carboplatin (Group 3, ■); and carboplatin with ODSH (Group 4, ▲), as described further in Example 2.

Figure 7:
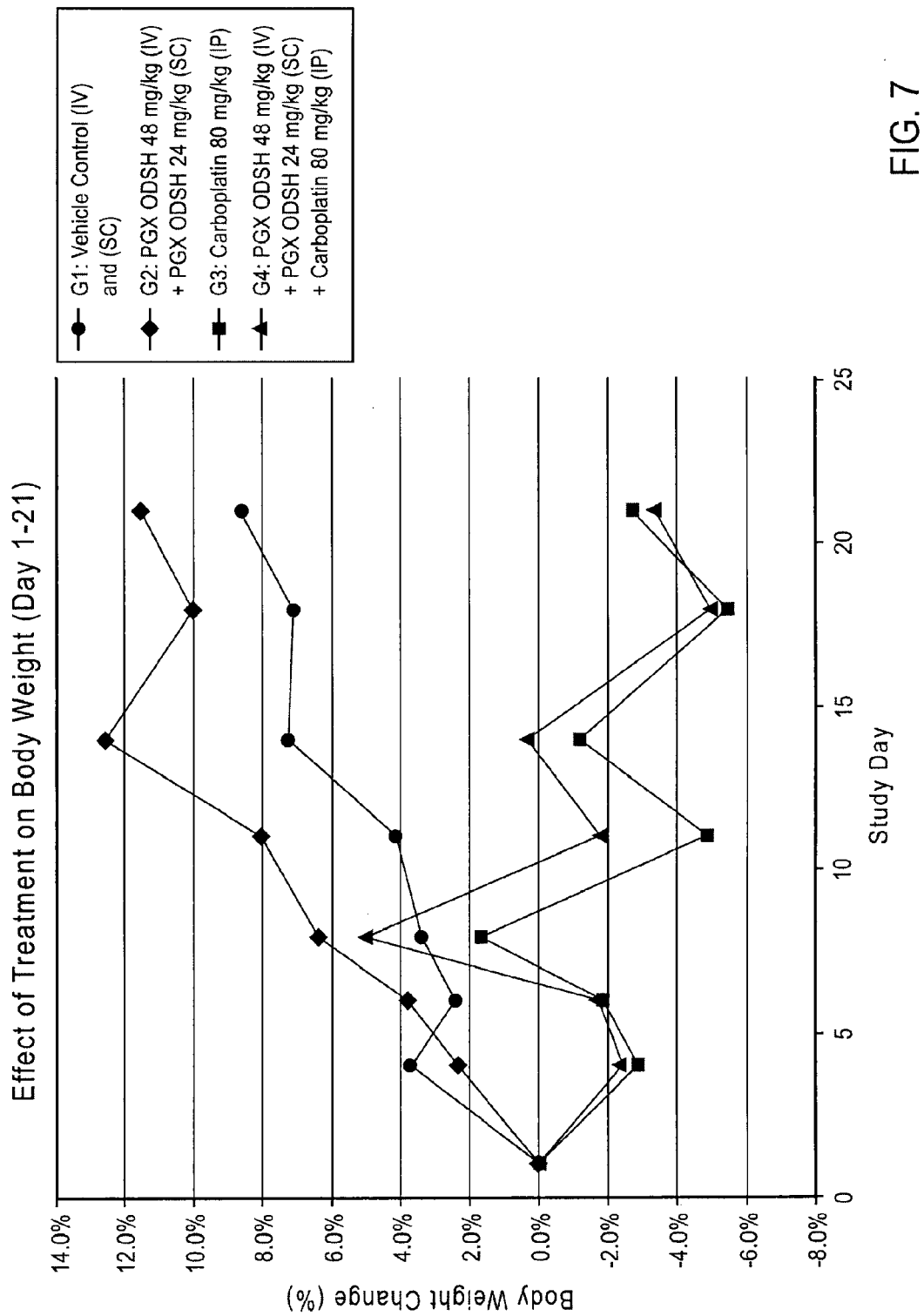

FIG. 7 provides a graph illustrating the effect on mouse body weight of the treatment regimens shown in FIG. 6 for days 1-21.

FIG. 8 provides a chart of the platelet count (in ×10³ platelets/µL) of patients with metastatic pancreatic cancer entered in the clinical trial described in Example 3, as measured in samples taken on day 1, day 8, and day 15 of each chemotherapy cycle as indicated (C1D1=cycle 1, day 1; C2D8=cycle 2, day 8, etc.). Horizontal lines mark the lower limit of normal platelet count (LLN) and the lower limit (LL) of the indicated grades of thrombocytopenia.

FIG. 9 provides a chart of the neutrophil count (in ×10³ neutrophils/µL) measured in samples taken from the same individuals described in FIG. 8, on day 1, day 8, and day 15 of each chemotherapy cycle as indicated (C1D1=cycle 1, day 1; C2D8=cycle 2, day 8, etc.). Horizontal lines mark the lower limit of normal neutrophil count (LLN) and the lower limit (LL) of the indicated grades of neutropenia.

FIG. 10A-10B provide mean and median platelet counts (FIG. 10A) and mean and median absolute neutrophil counts (FIG. 10B) for all samples at the indicated days in each of the indicated cycles.

Figure 11A:
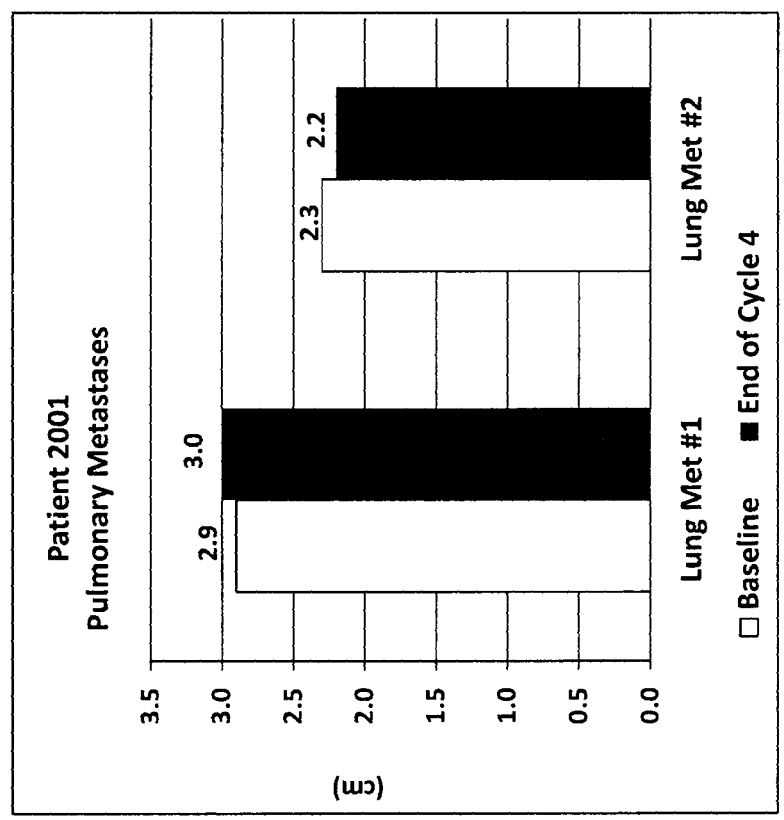
Figure 11C:
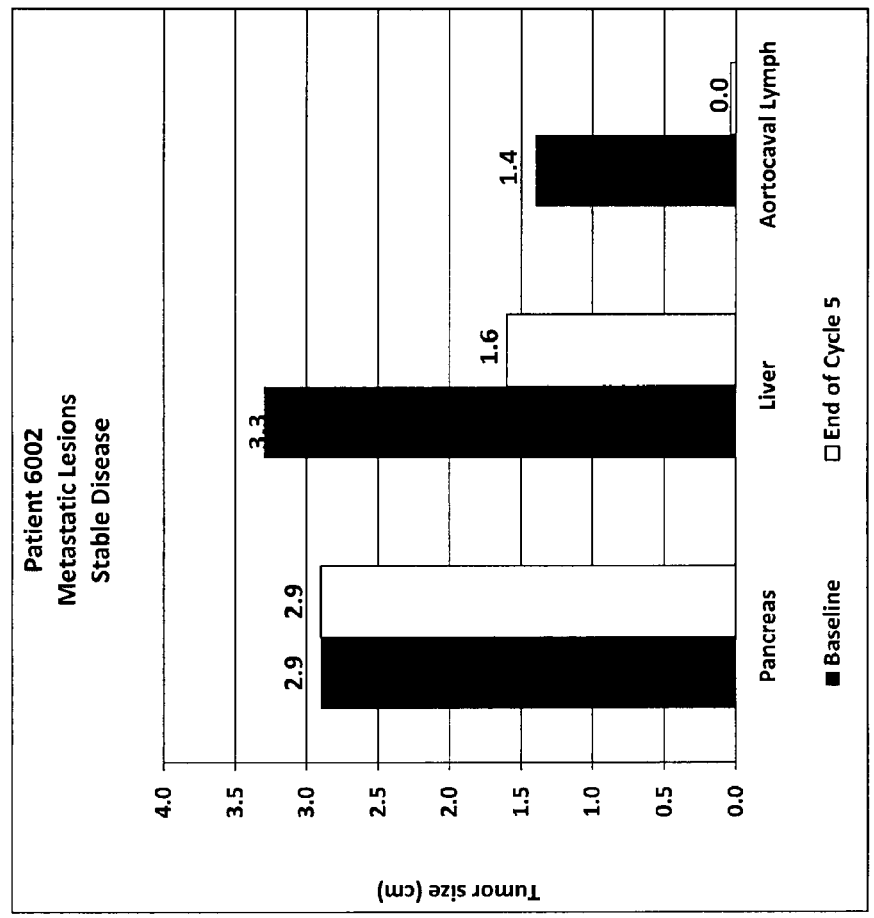
Figure 11D:
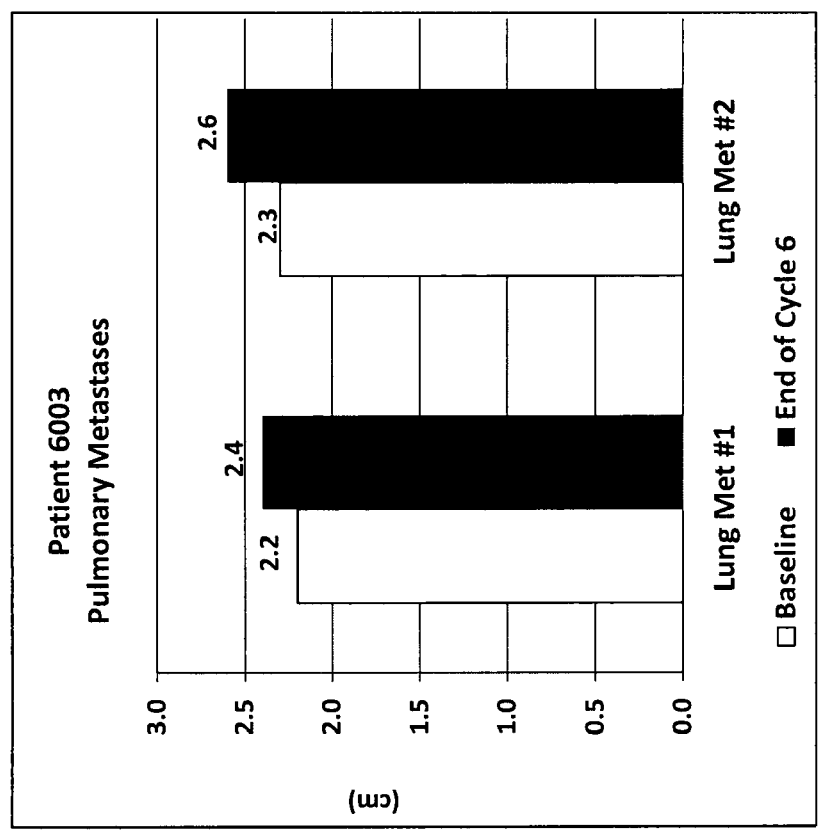
Figure 11E:
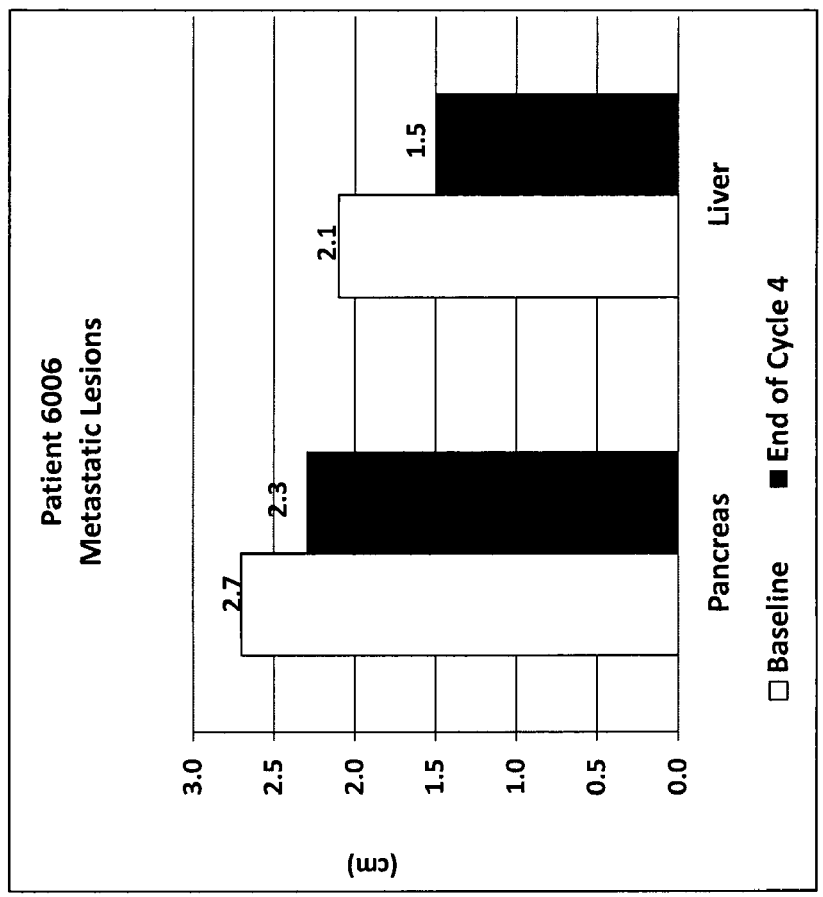
Figure 11F:
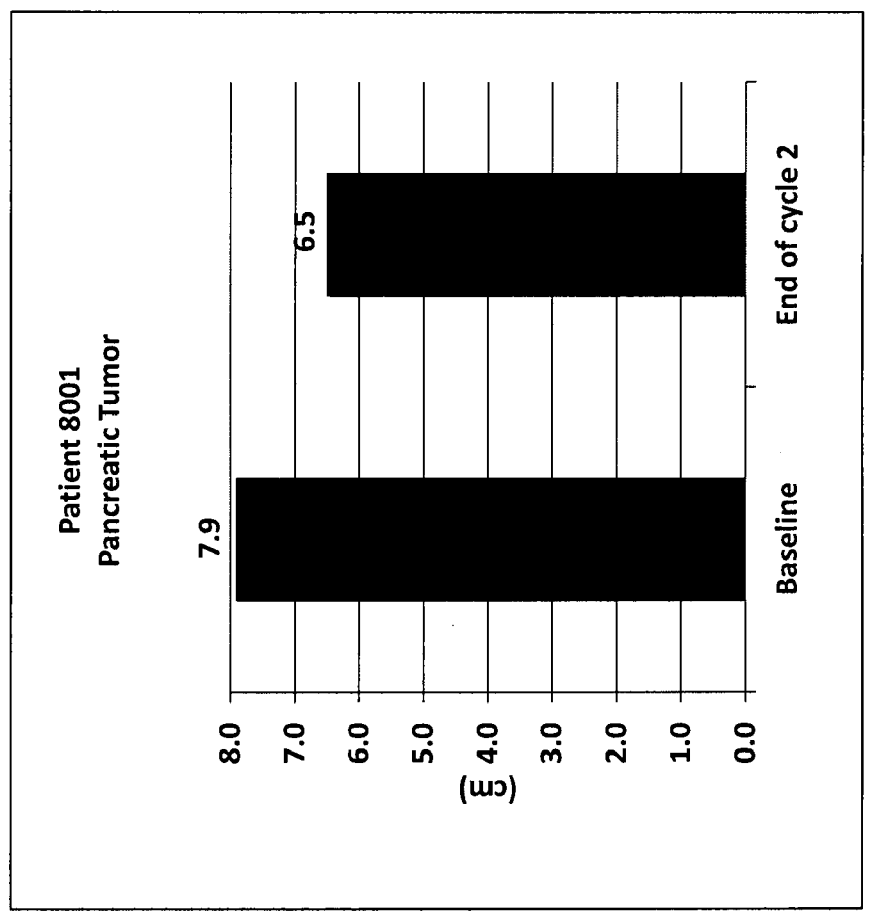

FIGS. 11A-F provides charts of the size of pancreatic and metastatic lesions in specific patients enrolled in the clinical trial described in Example 3 who have stable disease and who are receiving adjunctive administration of ODSH and chemotherapeutic agents. FIG. 11A shows the size of two pulmonary metastases in patient 2001 at baseline and at the end of cycle 4. FIGS. 11B-C show tumor size of metastatic lesions in the liver and lymph nodes at the end of treatment cycle 2 (FIG. 11B) and lesions in the pancreas, liver and lymph nodes at the end of cycle 5 (FIG. 11C) relative to the start of treatment (baseline) for patient 6002. FIG. 11D shows the size of two pulmonary metastases in patient 6003 at baseline and at the end of cycle 6. FIG. 11E shows the size of pancreatic tumors and a metastatic liver tumor in patient 6006 at baseline and at the end of cycle 4. FIG. 11F shows the size of a pancreatic tumor in patient 8001 at baseline and at the end of cycle 2.

Figure 12D:
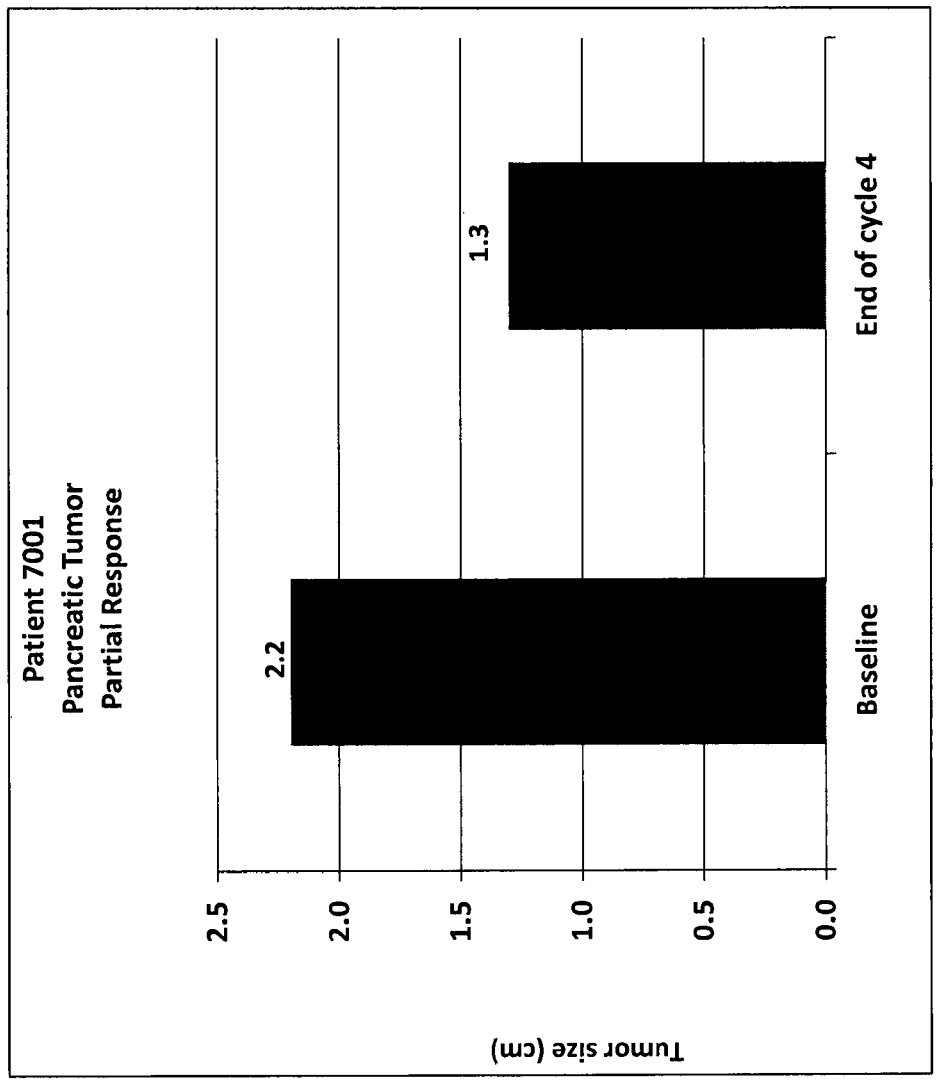
Figure 12E:
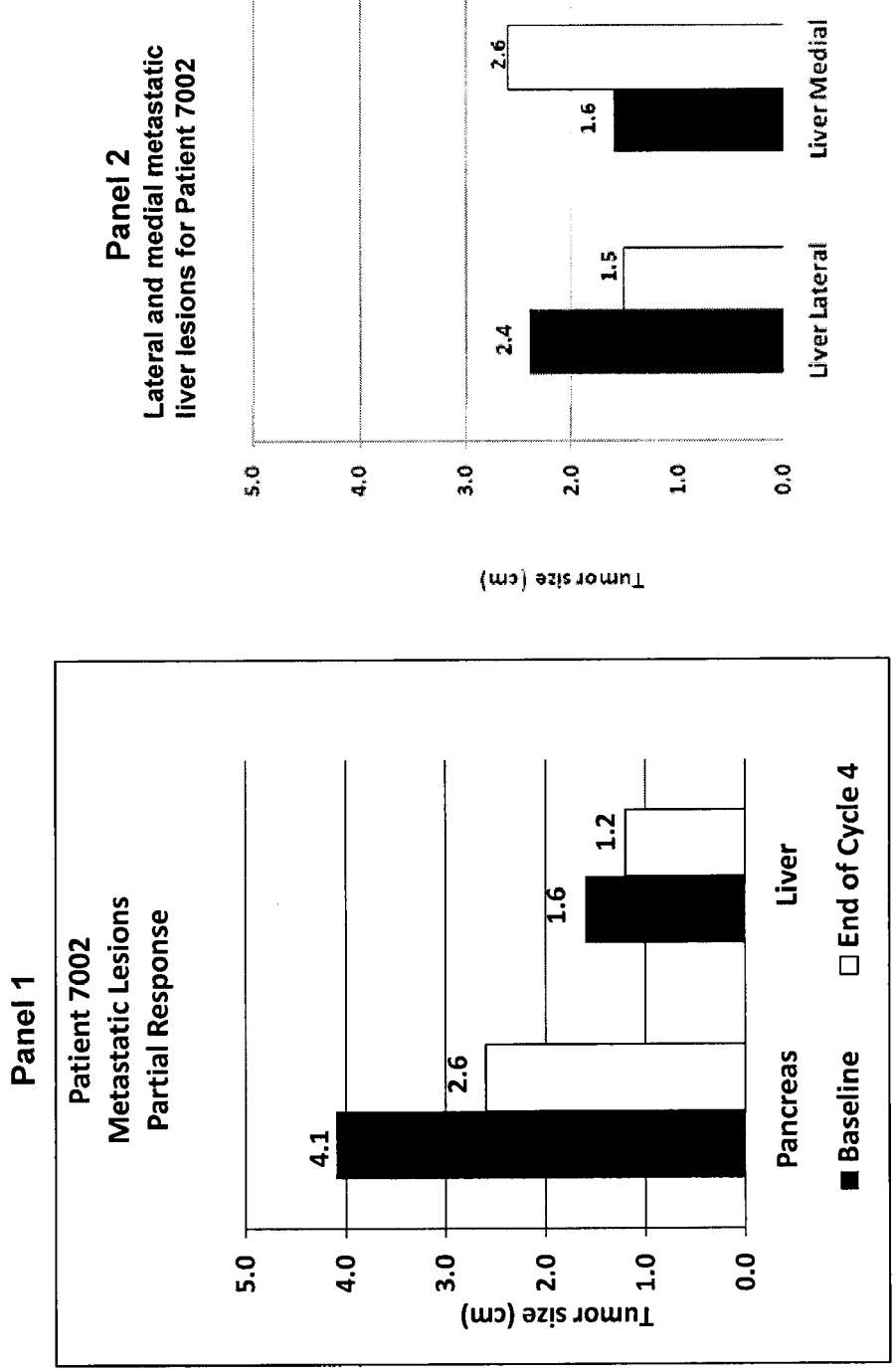
Figure 12F:
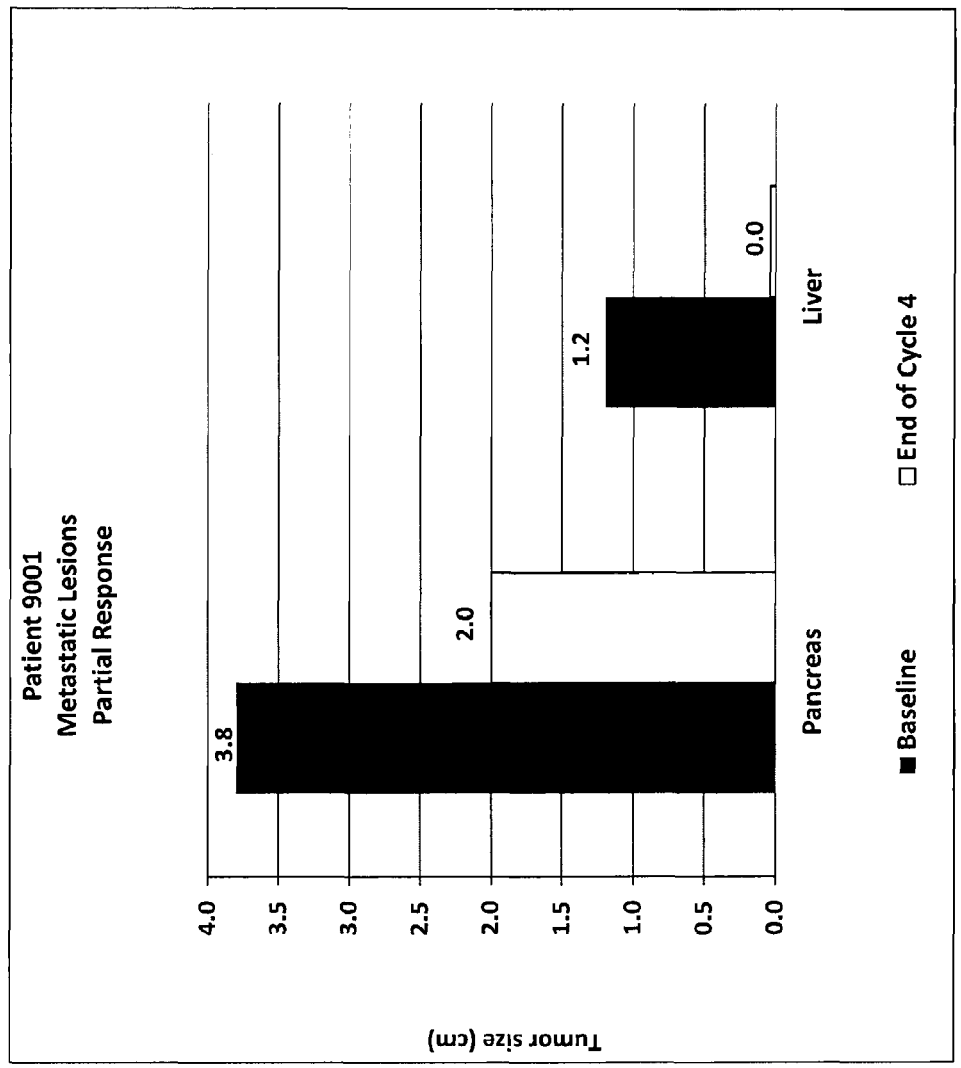

FIGS. 12A-F provide charts showing the tumor response of patients receiving adjunctive administration of ODSH and chemotherapy. FIG. 12A provides a chart summarizing sites of metastatic disease before the start of chemotherapy, levels of CA19-9 at baseline and after several chemotherapy cycles, and tumor response for each indicated patient. FIG. 12B-12F provides charts of the size of tumors for patients 6004, 6007, 7001, 7002, and 9001, showing a partial response at the end of treatment cycle 4 or 5, relative to baseline.

Figure 13B:
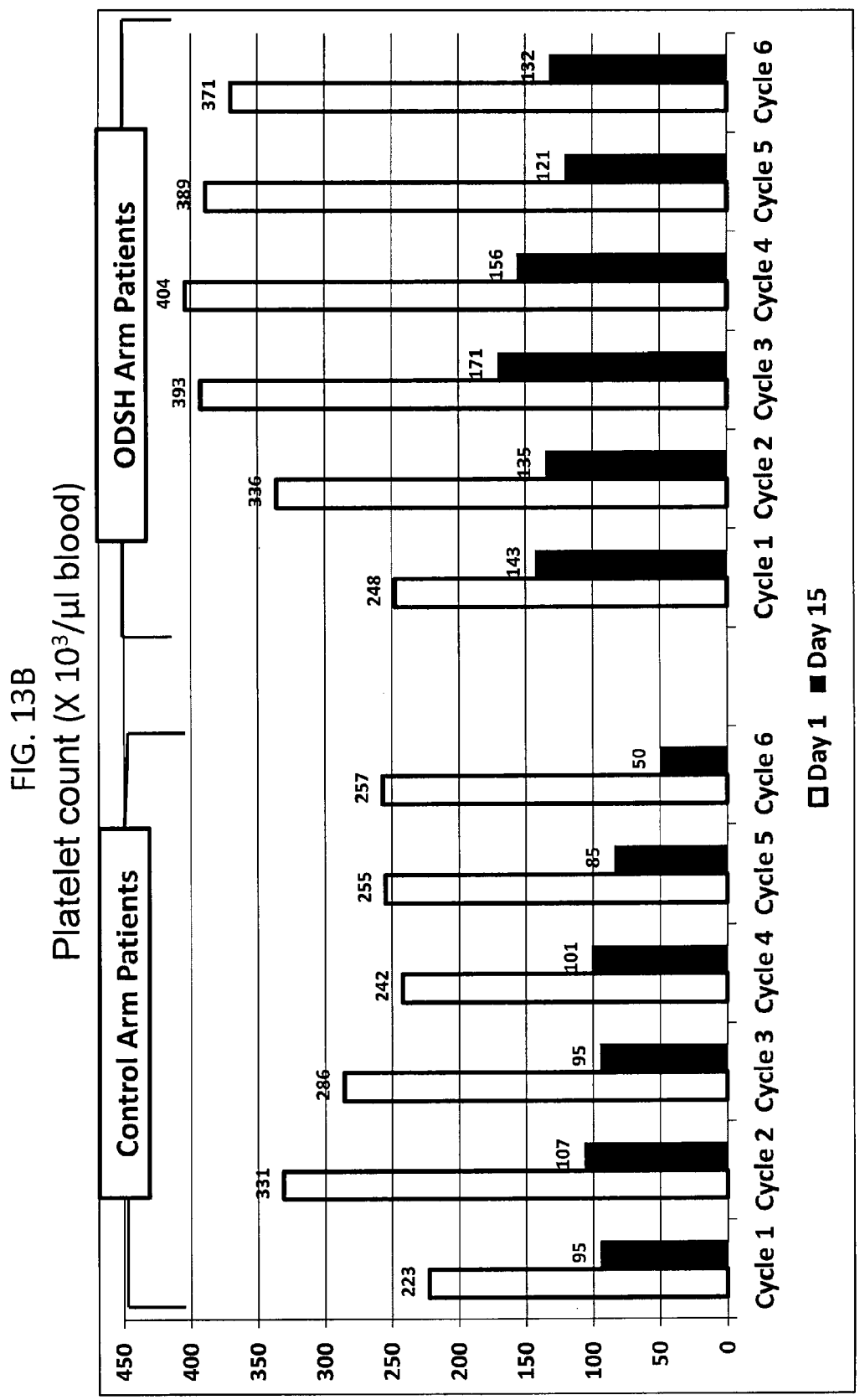

FIGS. 13A-B provide charts showing platelet counts at days 1 and 15 of indicated cycles for patients treated with gemcitabine, nab-paclitaxel, and ODSH ("ODSH arm patients") and patients treated with gemcitabine and nab-paclitaxel ("Control arm patients"). FIG. 13A provides a chart showing platelet counts, at day 1 of cycle 1 (before any chemotherapy) and at day 15 of cycle 1 (after two doses of chemotherapy) in 5 ODSH arm patients and 5 Control arm patients. Median and mean platelet counts for the control arm and the ODSH arm at days 1 and 15 are also shown. FIG. 13B provides a chart showing median platelet counts at days 1 and 15 of cycles 1 through 6 for Control arm patients and ODSH arm patients.

5. DETAILED DESCRIPTION

It has been discovered that heparinoids that are capable of interacting with platelet factor 4 (hereinafter, "PF4-interacting heparinoids") can attenuate thrombocytopenia and neutropenia of various etiologies. It has further been found that PF4-interacting heparinoids induce or disinhibit thrombopoiesis and granulopoiesis. Without intending to be bound by theory, it is thought that these effects are mediated by the ability of such heparinoids to reduce PF4 levels and/or counteract a suppressive effect of PF4 on megakaryopoiesis and granulopoiesis.

5.1. Methods of Attenuating Myelosuppressive Side Effects of Treatment Regimens As described in Example 3 below, patients diagnosed with metastatic pancreatic cancer who were treated adjunctively with an exemplary PF4-interacting heparinoid, referred to herein as ODSH (a heparinoid that is substantially desulfated at 2-O and 3-O positions, further described in Section 5.6), had increased platelet counts at the end of a first 4 week cycle of a chemotherapy regimen that is known to have a substantial myelosuppressive side effect. These effects continued in successive cycles of treatment and the results demonstrated that adjunctively administered ODSH attenuates thrombocytopenia and neutropenia in patients receiving a chemotherapy treatment regimen having myelosuppressive side effects.

Thus, in a first aspect, methods are provided for attenuating a myelosuppressive side effect of a patient treatment regimen. The methods comprise administering a therapeutically effective amount of a PF4-interacting heparinoid to the subject patient as an adjunct to the patient treatment regimen having myelosuppressive side effect. Thus, provided herein are uses of a PF4-interacting heparinoid, optionally ODSH, in the attenuation of a myelosuppressive side effect of a patient treatment regimen, as discussed further herein. The phrases "adjunctive administration", "adjunctively administering" or "administering adjunctive to" are used interchangeably herein to mean administering a PF4-interacting heparinoid in therapeutically effective temporal proximity to the treatment regimen that has a myelosuppressive side effect. By adjunctively administering a PF4-interacting heparinoid to patients receiving treatment regimens having a myelosuppressive side effect, either alone or in combination with other adjunctive agent(s) or therapy, Applicant has discovered that it is possible to attenuate the myelosuppressive side effect(s) of such treatment regimens.

PF4-interacting heparinoids suitable for use in the methods are described below in Section 5.6. In an exemplary embodiment, the PF4-interacting heparinoid is ODSH. Suitable modes of administration and dosing regimens are described further below, in Section 5.8. Effective dosages, and therapeutically effective amounts, of PF4-interacting heparinoid are described further below, in Section 5.9.

5.1.1. Treatment Regimens with Myelosuppressive Side Effects

As used herein, a myelosuppressive side effect is the occurrence of thrombocytopenia and/or neutropenia. Thus, in various embodiments, the treatment regimen, as a side effect, causes patients to develop thrombocytopenia (low platelet count), neutropenia (low neutrophil count), or a combination of thrombocytopenia and neutropenia. Such patient treatment regimens are also referred to herein as myelosuppressive treatment regimens.

In certain embodiments, the treatment regimen causes thrombocytopenia. In various embodiments, the treatment regimen causes platelet counts in blood to be less than about 150,000 platelets per µl of blood. In particular embodiments, the treatment regimen causes the patient to have platelet counts ranging from about 150,000 to about 75,000 platelets per µl of blood, corresponding to mild or grade 1 thrombocytopenia; platelet counts ranging from less than about 75,000 to about 50,000 platelets per µl of blood, corresponding to moderate or grade 2 thrombocytopenia; platelet counts ranging from less than about 50,000 to about 25,000 platelets per µl of blood, corresponding to severe or grade 3 thrombocytopenia; and platelet counts of less than about 25,000 platelets per µl of blood, corresponding to life-threatening or grade 4 thrombocytopenia. Thus, in a variety of embodiments, the patient treatment regimen induces, as a side effect, mild, moderate, severe, or life-threatening thrombocytopenia.

In certain embodiments, the treatment regimen causes neutropenia. In various embodiments, the treatment regimen causes patients to have absolute neutrophil counts in blood of less than about 2000 neutrophils per µl of blood. In particular embodiments, the treatment regimen causes the patient to have neutrophil counts ranging from about 2000 to about 1500 neutrophils per µl of blood, corresponding to mild or grade 1 neutropenia; absolute neutrophil counts ranging from less than about 1500 to about 1000 neutrophils per µl of blood, corresponding to moderate or grade 2 neutropenia; absolute neutrophil counts ranging from less than about 1000 to about 500 neutrophils per µl of blood, corresponding to severe or grade 3 neutropenia; and absolute neutrophil counts of less than about 500 neutrophils per µl of blood, corresponding to life-threatening or grade 4 neutropenia. Thus, in a variety of embodiments, the patient treatment regimen induces, as a side effect, mild, moderate, severe, or life-threatening neutropenia.

In a variety of embodiments, the patient treatment regimen is an antineoplastic treatment regimen. In certain embodiments, the antineoplastic treatment regimen is chemotherapy. In certain embodiments, the antineoplastic treatment regimen is radiation therapy.

In chemotherapy embodiments, the patient treatment regimen includes administration of one or more chemotherapeutic agent(s).

In exemplary embodiments, at least one of the one or more chemotherapeutic agents is selected from the group consisting of: folate antagonists, including methotrexate and pemetrexed; purine antagonists, including cladribine, clofarabine, fludarabine, 6-mercaptopurine, nelarabine, pentostatin; pyrimidine antagonists, including capecitabine, cytarabine, 5-fluorouracil, gemcitabine, hydroxyurea; biologic response modifiers, including interferon-alfa; bleomycin; DNA alkylating agents, including nitrosureas, carmustine, lomustine; DNA cross-linking drugs and alkylating agents, including bendamustine, chlorambucil, cyclophosphamide, ifosfamide, mechlorethamine (nitrogen mustard), melphalan, dacarbazine, temozolomide, procarbazine; asparaginase; antibiotics, including mitomycin; platinum complexes, including carboplatin, cisplatin, oxaliplatin; proteosome inhibitors, including bortezomib; spindle poisons, such as the taxanes (including docetaxel, paclitaxel, nab-paclitaxel (Abraxane®)) and the vincas (including vinblastine, vincristine, vinorelbine); topoisomerase inhibitors, such as the anthracyclines (including daunorubicin, daunomycin, doxorubicin, epirubicin), the camptothecines, (including irinotecan, topotecan), the podophyllotoxins (including etoposide, teniposide and mitoxantrone); tyrosine kinase inhibitors, (including erlotinib (Tarceva), gefitinib, imatinib, lapatinib, pazopanib, sorafenib, sunitinib); and ifosfamide.

In various embodiments, one or more other chemotherapeutic agents are used.

In certain exemplary embodiments, the myelosuppresive chemotherapeutic treatment regimen includes administration of a taxane, such as docetaxel, or a taxol, such as paclitaxel (e.g., nab-paclitaxel, Abraxane®) in combination with one or more additional chemotherapeutic agent(s), including but not limited to any of the agents described above. In some embodiments, the patient treatment regimen includes administration of a taxane, such as docetaxel, or a taxol, such as paclitaxel (e.g., nab-paclitaxel, Abraxane®) in combination with one or more of a folate, purine, or pyrimidine antagonist, a DNA alkylating agent, a platinum complex, a vinca, an anthracycline, a camptothecine, a podophyllotoxin, and/or a tyrosine kinse inhibitor. In specific embodiments, the patient treatment regimen includes administration of a taxane, such as docetaxel, paclitaxel (e.g., nab-paclitaxel, Abraxane®) in combination with one or more agent selected from: gemcitabine, vinorelbine, carboplatin, cisplatin, oxaliplatin, temozolomide, and mifepristone. In exemplary embodiments, two or more chemotherapeutic agents are administered, the two or more chemotherapeutic agents selected from: cisplatin and etoposide; carboplatin and etoposide; cisplatin and irinotecan; carboplatin and irinotecan; cyclophosphamide, doxorubicin (Adriamycin), and vincristine; cyclophosphamide/doxorubicin/vincristine (known as the CAV regimen); gemcitabine with vinorelbine or paclitaxel or nab-paclitaxel (Abraxane®); gemcitabine or capecitabine with oxaliplatin; cisplatin or carboplatin plus another chemotherapeutic agent; 5-fluorouracil with one or more of leuvocorin, oxaliplatin, irinotecan.

The myelosuppressive patient treatment regimen, in various embodiments, comprises administration of chemotherapeutic agents according to specific named regimens. In exemplary embodiments, the patient chemotherapy treatment regimen includes one or more of the following specific regimens: 5FU Mayo, 5FU Roswell Park, LVFU2, FOLFOX4, FOLFOX6, bFOL, FUFOX, IFL, XELOX, XELIRI, and CAPIRI, which are described in further detail in Chau et al., 2009, *Br. J. Cancer* 100:1704-19; and Field et al., 2007, *World J. Gastroenterol.* 13:3806-15, both of which are incorporated herein by reference. Another specific named regimen is CHOP, combining cyclophosphamide, hydroxydaunorubicin (or doxorubicin or adriamycin), vincristine (or oncovin), and prednisone or prednisolone, generally used to treat patients with non-Hodgkin's lymphoma. In some embodiments, e.g., where the patient being treated has a history of cardiovascular disease, doxorubicin is omitted from the regimen, which is then referred to as COP or CVP. Optionally, the CHOP regimen can be further combined with rituximab (Rituxan) and is then referred to as R-CHOP or CHOP-R. Other combinations are also possible. Another specific named regimen is ICE, combining chemotherapeutic agents ifosfamide, carboplatin, and etoposide. See Habermann, 2012, *Hematology* 17 Suppl 1:S93-7, which is incorporated herein by reference.

Antineoplastic patient treatment regimens that include radiation therapy have also been shown to have myelosuppressive side effects, sometimes referred to as radiation-induced thrombocytopenia and radiation-induced neutropenia. In various radiation embodiments, the patient treatment regimen includes radiation therapy selected from radiation therapy with x-rays, gamma rays, neutrons, protons, and other sources, external beam radiation therapy, and internal radiation therapy, such as brachytherapy.

Patient treatment regimens in which one or more antibodies having a cytotoxic effect are administered, referred to herein as antibody therapy, may also have myelosuppressive side effects that are usefully treated by adjunctive administration of a PF4-interacting heparinoid according to the methods described herein. Thus, in certain embodiments, the treatment regimen having myelosuppressive side effects comprises antibody therapy. In some embodiments, the antibody therapy includes one or more antibodies conjugated to a toxin, where the antibody binds to and/or is internalized by a target tumor cell and the toxin kills the cell. In exemplary embodiments, the patient treatment regimen includes administration of one or more antibodies having a myelosuppressive side effect, such as abciximab (ReoPro), rituximab (Rituxan), trastuzumab (Herceptin) conjugated to mertansine (T-DM1), and infliximab (Remicade). In some embodiments, the patient treatment regimen includes administration of one or more of the following: trastuzumab (Herceptin), cetuximab, bevacizumab (Avastin), tigatuzumab.

In various embodiments, patient treatment regimens that have myelosuppressive side effects, and that are usefully treated by adjunctive administration of a PF4-interacting heparinoid according to the methods described herein, include combinations of chemotherapy, radiation therapy and/or antibody therapy. In some embodiments, the patient treatment regimen comprises chemotherapy, e.g. with one or more of the agents described herein, and radiation therapy; or chemotherapy, e.g. with one or more of the agents described herein, and antibody therapy, e.g. with one or more of the antibodies described herein; radiation therapy and antibody therapy, e.g., with one or more of the antibodies described herein; or any two, three, four, five or more agents or therapies described herein. In exemplary embodiments, such as where the patient has non-Hodgkin's lymphoma, the patient treatment regimen comprises antibody therapy with rituxan and chemotherapy with CHOP (also referred to as R-CHOP), COP, CVP, or ICE (also referred to as R-ICE) regimen. See Habermann, 2012, *Hematology* 17 Suppl 1:S93-97.

Patient treatment regimens involving transplantation, such as bone marrow transplant or stem cell transplant, may also have myelosuppressive side effects. Thus, in some embodiments, the patient treatment regimen comprises an autologous or allogeneic bone marrow or stem cell transplant.

In a variety of embodiments, the patient treatment regimens include regimens in which one or more agents with thrombocytopenic side effects are administered. In exemplary embodiments, the one or more agent with a thrombocytopenic side effect is selected from: valproic acid, proton pump inhibitors, interferon (e.g. interferon-alpha), isotretinoin, panobinostat, thiazide diurectics, montelukast sodium (Singulair), quinidine, quinine, gold, sulfonamides, cephalothin, phenylbutazone, diphenylhydantoin, digitoxin and phenothiazine tranquilizers, and heparin.

In various embodiments, the patient treatment regimens include regimens in which one or more agents with neutropenic side effects are administered. In exemplary embodiments, the one or more agent with a neutropenic side effect is selected from: cyclophosphamide, psychotropic drugs and anticonvulsants such as clozapine and olanzapine, thionamides, ticlopidine, carbimazole, dapsone, dipyrone, methimazole, penicillin G, procainamide, propylthiouracil, trimethoprim, chloramphenicol, penicillins, cephalosporins, aminoglycosides, tetracyclines, nitroimidazoles, nitrofurantoin, flucytosine, rifampin, isoniazid, ethambutol, dapsone, sulfonamide antibiotics, clomiprimine, thiacetazone, dipyrone, sulfasalazine, mesalazine, ciprofloxacin, chloroquin, mebendazole, terbendafine, pyrimethamine, levamisole, ristocetin, griseofulvin, phenothiazines, benzodiazepines, amoxapine, meprobamate, barbiturates, risperidone, imipramine, desipramine, thiothixene, haloperidol, valproic acid, hydantoins, succinimides, trimethadione, carbamazepine, procainamide, quinidine, propafenone, captopril, propranolol, hydralazine, methyldopa, ibuprofen, indomethacin, sulindac, tolmetin, aspirin, aminopyine, phenylbutazone, diflunisal, benoxaprofen, allopurinol, colchicine, propylthiouracil, thiouracil, methimazole, carbimazole, thiocyanate, potassium perchlorate, cimetidine, ranatadine, tripelennamine, methaphenilene, thenalidine, mianserin, bromopheneramine, quinine, hydroxychloroquin, quinacrine, diazoxide, dihydropyridines, vesnarinone, aprindine, imipenem/cilastatin, zidovudine, fludarabine, acyclovir, turbinafine, aminoglutethimide, famotidine, bezafibrate, flutamide, tamoxafen, penicillamine, retinoic acid, metoclopramide, phenindone, dinitrophenol, ethacrynic acid, rauwolfia, ethanol, chlorpropamide, tolbutamide, thiazides, spironolactone, methazolamide, acetazolamide, levodopa and combinations thereof. See, Oyesanme et al., 1999, *Psychosomatics,* 40:5 at p. 414 421; the disclosure of which is incorporated herein by reference.

In certain embodiments, the myelosuppressive patient treatment regimen comprises one or more regimens suitable for the treatment of subjects diagnosed with acute myelogenous or myeloid leukemia ("AML"). Treatment regimens for AML typically consist of two phases, an initial phase intended to induce remission, referred to as the induction phase, and a second phase intended to prevent recurrence or relapse, referred to as the consolidation phase. Treatments administered during the induction phase are referred to as induction treatment regimens and treatments administered during the consolidation phase are referred to as consolidation treatment regimens. Standard induction treatment regimens include chemotherapy, referred to as induction chemotherapy, and are known in the art. In an exemplary embodiment of induction chemotherapy, the chemotherapy regimen consists of treatment with cytarabine (araC) administered intravenously for 7 consecutive days and an anthracycline agent (e.g., daunorubicin or idarubicin) administered on 3 consecutive days. See Tallman, 2005, *Hematology* 2005: 143-150; Robak et al., 2009, *Clin. Therap.* 31:2349-70. Consolidation treatment regimens can comprise chemotherapy, immunotherapy, bone marrow transplant, or combinations thereof. In some embodiments, consolidation chemotherapy consists of one or more cycles of the same chemotherapy regimen used during the induction phase. In other embodiments, consolidation chemotherapy consists of one or more cycles of high dose chemotherapy. Exemplary embodiments of consolidation chemotherapy include two, three, four, five, or more cycles of treatment with cytarabine and an anthracycline regimen as described above. In some embodiments, the consolidation chemotherapeutic regimen comprises a higher dose of the chemotherapeutic agent or agents administered during the induction phase. The consolidation phase can also comprise immunotherapy with one or more agents such as, but not limited to, histamine dihydrochloride and interleukin-2. In certain embodiments, the consolidation treatment regimen comprises an allogeneic stem cell transplant. In various embodiments, a PF4-interacting heparinoid is administered adjunctively to an induction and/or consolidation treatment regimen. In an exemplary embodiment, ODSH is administered adjunctively to an induction and/or consolidation treatment regimen.

5.1.2. Treatment Subjects

The subject to be treated (used interchangeably herein with "patient") may be any animal, for example a mammal, preferably a human. In certain embodiments, the subject is an adult. In certain embodiments, the subject is a child, for example a child diagnosed with a pediatric cancer.

In some embodiments, suitable subjects are patients diagnosed with cancer, and in need of an antineoplastic or cytotoxic treatment regimen. The cancer can be a solid tumor cancer in any organ or tissue, including pancreatic cancer, ovarian cancer, uterine cancer, breast cancer, including metastatic breast cancer and chemotherapy-resistant breast cancer (e.g., breast cancer that recurs as a relapse within 6 months of adjuvant chemotherapy with or without an anthracycline), head and neck cancer, bladder cancer, urothelial cancer, lung cancer (including non-small cell lung cancer), colorectal cancer, gastric cancer, esophageal cancer, neuroblastoma, liver cancer, melanoma, prostate cancer, osteosarcoma, and can be a hematologic cancer, such as lymphoma (including recurrent, Hodgkin's, and non-Hodgkin's lymphomas), and leukemia (including acute myelogenous leukemia, or AML, and pediatric acute lymphoblastic leukemia).

The methods described herein are particularly useful for cancers in which PF4 levels are elevated either in platelets or in the blood. Thus, in some embodiments, the subject has been diagnosed with a cancer in which PF4 levels are elevated either in platelets or in the blood. In certain embodiments, the cancer is pancreatic cancer, colorectal cancer, osteosarcoma or leukemia (including acute myelogenous leukemia and pediatric acute lymphoblastic leukemia).

Suitable subjects for treatment also include subjects suffering from a disease or condition for which the recommended treatment regimen has a myelosuppressive side effect, including any of the treatment regimens described above in Section 5.1.1.

In various embodiments, the suitable subject is a subject having an elevated level of PF4 in blood or in platelets, including various cancers above-described and non-cancerous conditions with elevated levels of PF4 in blood or in platelets, a subject with an autoimmune disease that can be treated with a treatment regimen including one or more agents having a myelosuppressive side effect, such as rheumatoid arthritis, systemic lupus erythematosus, multiple sclerosis, Crohn's disease, ulcerative colitis, inflammatory bowel disease, or a subject having decreased thrombopoietin levels, such as patients with liver cancer, viral hepatitis, cirrhosis, or impaired liver function.

In various embodiments, the suitable subject is a subject who does not have immune-mediated thrombocytopenia, thrombocytopenia due to an autoimmune condition, thrombocytopenia caused by increased destruction of platelets, or heparin-induced thrombocytopenia.

In embodiments in which the PF4-interacting heparin is partially desulfated, such as 2-O, 3-O desulfated heparin, there is a reduced risk of heparin-induced thrombocytopenia, even when administered in combination with heparin (unfractionated heparin or low molecular weight heparin) as an anticoagulant agent. See U.S. Pat. No. 7,468,358. Consequently, in some embodiments, the patient may be a subject who has antibodies against heparin-PF4 complex and is at risk of heparin-induced thrombocytopenia.

5.1.3. Other Adjunctive Agents and Therapy

The PF4-interacting heparinoid can be administered either as a sole agent adjunctive to a patient treatment regimen having a myelosuppressive side effect, or in combination with one or more additional agents or therapies.

Thus, in various embodiments, the methods further comprise adjunctive administration of one or more additional agents or therapies that are also capable of attenuating thrombocytopenia and/or promoting thrombopoiesis, attenuating neutropenia and/or promoting granulopoiesis. In certain embodiments, the methods further comprise adjunctive administration of an anti-coagulating heparinoid. In some embodiments, two or more such agents and/or therapies are administered. The two or more such agents can have the same activity (e.g., anti-thrombocytopenic), different activity (e.g., a first agent is pro-thrombopoietic and a second agent is anti-neutropenic), or overlapping activity (e.g., a first agent is pro-granulopoietic and anticoagulant and a second agent is anti-coagulant).

Suitable additional therapies or agents to attenuate thrombocytopenia and/or promote thrombopoiesis include agents or therapies that act to increase platelet count. Thus, in some embodiments, the one or more additional agent or therapy is selected from platelet transfusion, splenectomy, corticosteroids (e.g., prednisone and dexamethasone), platelet clearance inhibitors (e.g., danazol), thrombopoeitin, thrombopoietin mimetics (e.g., Nplate®, eltrombopag (Promacta®)), thrombopoietin receptor agonists (e.g., romiplostim and eltrombopag), interleukins, e.g. recombinant human interleukins (including interleukin-1, interleukin-3, interleukin-6, interleukin-11 (e.g., Numega®)), lithium carbonate, and folate.

Suitable additional therapies or agents to attenuate neutropenia and/or promote granulopoiesis include agents that act to increase neutrophil count. Thus, in some embodiments, the one or more additional agent or therapy is selected from recombinant human granulocyte colony stimulating factor ("G-CSF") (filgrastim (Neupogen), pegfilgrastim (Neulasta)), and recombinant human granulocyte-macrophage colony stimulating factor ("GM-CSF") (sargramostim (Leukine)).

In some clinical presentations, the patient may benefit from anti-coagulation therapy. Thus, in some embodiments, the methods comprise administering PF4-interacting heparinoid in combination with one or more anti-coagulating agents, such as one or more anti-coagulant heparinoids, preferably in such amounts, or in such ratios, as to provide anticoagulation without risk of inducing or triggering heparin-induced thrombocytopenia. In exemplary embodiments, anti-coagulation agents are selected from heparins, such as unfractionated heparin, and low molecular weight heparins, such as dalteparin, enoxaparin, fondaparinux, reviparin, and tinzaperin. Generally, the PF4-interacting heparinoid and the anti-coagulant are administered in ratios in which the molar or weight amount of PF4-interacting heparinoid exceeds the molar or weight amount of anti-coagulant. In some embodiments, molar ratios of PF4-interacting heparinoid to anticoagulant heparin range from about 1:2 to about 10:1. Equivalent weight ratios are also contemplated. In some embodiments, weight ratios of PF4-interacting heparinoid to anticoagulant heparin range about 1:1 to about 4:1.

In various embodiments, the one or more additional adjunctive agents or therapies is administered concurrently, sequentially, or separately with PF4-interacting heparinoid. In some embodiments, the one or more additional agents or therapies is administered both concurrently and sequentially with PF4-interacting heparinoid.

5.2. Method of Promoting Thrombopoiesis

It has now been discovered that PF4-interacting heparinoids can increase platelet counts in human patients. As described in Example 3 below, patients treated with ODSH had increased platelet counts at the end of a first 4 week cycle of a chemotherapy regimen for pancreatic cancer that has a substantial myelosuppressive side effect. This effect continued through successive cycles, with patients showing platelet counts above levels seen at screening (i.e., prior to treatment with ODSH), after two, three, or even four cycles of adjunctive administration of ODSH and the chemotherapy treatment regimen. Thus, in another aspect, methods for promoting thrombopoiesis in a subject are provided. The methods comprise administering an effective amount of a PF4-interacting heparinoid to the subject. PF4-interacting heparinoids for use in the methods are described below in Section 5.6. In an exemplary embodiment, the PF4-interacting heparinoid is ODSH. Suitable modes of administration and dosing regimens are described further below, in Section 5.8. Effective dosages, and therapeutically effective amounts, of PF4-interacting heparinoid are described further below, in Section 5.9.

The method can be carried out in a thrombocytopenic subject or a non-thrombocytopenic subject.

In embodiments in which the subject is thrombocytopenic, the thrombocytopenia can be of varying etiology. Thus, in various embodiments, the thrombocytopenia is (1) thrombocytopenia caused by a treatment regimen with a myelosuppressive side effect, as described above in Section 5.1.1, and the subjects may include those described above in Section 5.1.2, (2) thrombocytopenia caused by impaired production of platelets by the bone marrow, (3) thrombocytopenia caused by platelet sequestration in the spleen (splenomegaly), or (4) thrombocytopenia caused by increased destruction of platelets in the peripheral circulation, optionally due to an autoimmune condition.

In various embodiments, the subject's platelet count is reduced as a result of—and, optionally, thrombocytopenia caused by—a disease or condition. Accordingly, in certain embodiments, the subject is suffering from an infection. In some embodiments, the infection results in sepsis, with or without disseminated intravascular coagulation. In some embodiments, subjects have elevated plasma levels of PF4, for example, more than about 5 ng/ml, more than about 6 ng/ml, more than about 7 ng/ml, more than about 8 ng/ml, more than about 9 ng/ml, more than about 10 ng/ml, more than about 11 ng/ml, more than about 12 ng/ml, more than about 15 ng/ml, more than about 17 ng/ml, more than about 20 ng/ml, more than about 22 ng/ml, more than about 25 ng/ml, more than about 27 ng/ml, more than about 30 ng/ml, more than about 40 ng/ml, up to about 45 ng/ml, up to about 50 ng/ml or greater. Lorenz et al., 1988, Infection 16(5):273-6 and PF4 assay therein. In some embodiments, the subjects have thrombocytopenia that is not heparin-induced thrombocytopenia.

In exemplary embodiments, the thrombocytopenia is selected from radiation-induced thrombocytopenia; drug-induced thrombocytopenia; consumption thrombocytopenia; immune-mediated thrombocytopenia, including alloimmune thrombocytopenia and auto-immune thrombocytopenia, including immune thrombocytopenic purpura (or ITP); infectious cyclic thrombocytopenia; myelophthisic thrombocytopenia caused by neoplastic invasion of the bone marrow; surface-induced thrombocytopenia; vaccine-induced thrombocytopenia; liver, bone marrow or stem cell transplant-induced thrombocytopenia; and thrombocytopenia attendant to autoimmune disease (e.g., rheumatoid arthritis, systemic lupus erythematosus) or lymphoproliferative disorder (e.g., chronic lymphocytic leukemia). In some embodiments, the thrombocytopenia is not or is other than: immune-mediated thrombocytopenia, thrombocytopenia due to an autoimmune condition or thrombocytopenia caused by increased destruction of platelets. In some embodiments, the thrombocytopenia is other than heparin-induced thrombocytopenia.

In various embodiments, the methods of promoting thrombopoiesis are useful for treating a subject who has radiation-induced thrombocytopenia caused by radiation therapy or by non-therapeutic exposure to ionizing radiation, for example a subject who has radiation poisoning or radiation sickness as a result of a radiological or nuclear accident or attack.

In various embodiments, suitable subjects include patients who would benefit from an increased platelet count, such as in advance of surgery, transfusion, therapy with a treatment regimen having a myelosuppressive side effect, or other procedure or treatment that could lower platelet count or increase the need for clotting. In exemplary embodiments, the subject is diagnosed with cancer, and/or is in need of surgery, transfusion, or therapy with a treatment regimen having a myelosuppressive side effect. In some embodiments, the subject is at risk for radiation-induced thrombocytopenia due to radiation therapy or non-therapeutic exposure to ionizing radiation, for example as a result of a radiological or nuclear accident or attack.

5.2.1. Additional Agents and Therapy

In methods of promoting thrombopoiesis, the PF4-interacting heparinoid can be administered either as a sole agent or in adjunctive combination with one or more additional agents or therapies. In some embodiments, the one or more additional agents or therapy is capable of promoting thrombopoiesis. In various embodiments, the one or more additional agents or therapy is anti-coagulating.

Suitable additional therapies or agents to promote thrombopoiesis include agents or therapies that act to increase platelet count. In exemplary embodiments, the one or more additional agents or therapy is selected from platelet transfusion, splenectomy, corticosteroids (e.g., prednisone and dexamethasone), platelet clearance inhibitors (e.g., danazol), thrombopoeitin, thrombopoietin mimics, thrombopoietin receptor agonists (e.g., romiplostim and eltrombopag), interleukins, e.g. recombinant human interleukins (including interleukin-1, interleukin-3, interleukin-6, interleukin-11), lithium carbonate, and folate. Other additional agents and therapy are described in Section 5.1.3.

In some clinical presentations, the patient may need anticoagulation therapy, despite requiring thrombopoiesis. Thus, in some embodiments, the PF4-interacting heparinoid is administered adjunctive to one or more anti-coagulating agents, preferably without risk of inducing or triggering heparin-induced thrombocytopenia. Anti-coagulation agents include heparins, such as unfractionated heparin, and low molecular weight heparins, such as dalteparin, enoxaparin, fondaparinux, reviparin, tinzaperin. Generally, the PF4-interacting heparinoid and the anti-coagulant can be administered in ratios in which the amount of PF4-interacting heparinoid exceeds the amount of anti-coagulant. Molar ratios of PF4-interacting heparinoid to anticoagulant heparin range from about 1:2 to about 10:1. Equivalent weight ratios are also contemplated.

5.3. Method of Promoting Neutrophil Production

It has now been discovered that PF4-interacting heparinoids can increase neutrophil counts in human patients. As further described in Example 3 below, patients treated with ODSH had increased neutrophil counts at the end of a first 4 week cycle of chemotherapy, despite receiving concurrent treatment with a chemotherapeutic regimen having myelosuppressive side effects, and consistently showed increased neutrophil counts at the end of successive 4-week cycles relative to neutrophil counts mid-cycle. In some instances, patients showed neutrophil counts above levels seen at screening (i.e., prior to treatment with ODSH), after two, three, or even four cycles of adjunctive administration of ODSH and the chemotherapy treatment regimen. Thus, in another aspect, methods for promoting neutrophil production in a subject are presented. The methods comprise administering an effective amount of a PF4-interacting heparinoid, as described further in Section 5.6 below, to the subject. In an exemplary embodiment, the PF4-interacting heparinoid is ODSH. Suitable modes of administration and dosing regimens are described further below, in Section 5.8. Effective dosages, and therapeutically effective amounts, of PF4-interacting heparinoid are described further below, in Section 5.9.

The method can be carried out in a neutropenic subject or a non-neutropenic subject. The subject can be an adult or a child. In various embodiments, the subjects include those described above at Section 5.1.2.

In embodiments in which the subject to be treated is neutropenic, the neutropenia may be chronic or acute. In various embodiments, the neutropenia is congenital (e.g., caused by Kostmann's Syndrome), cyclical or idiopathic. In some embodiments, the neutropenia is secondary to another condition, such as cancer, viral infection (e.g., acquired immunodeficiency syndrome (AIDS)). In some embodiments, the neutropenia is autoimmune. In some embodiments, neutropenia is caused by infiltration and destruction of bone marrow due to leukemia, myeloma, lymphoma or a metastatic solid tumor such as, for example, breast or prostate cancer. In some embodiments, the neutropenia is radiation-induced neutropenia, resulting from intentional or non-therapeutic exposure to ionizing radiation, for example as a result of a radiological or nuclear accident or attack.

Neutropenia can be a side effect of agents or procedures. Thus, in some embodiments, neutropenia is caused by a treatment regimen having a myelosuppressive side effect, e.g., chemotherapy, radiation therapy for cancer, bone marrow transplantation associated with cancer therapy and as described above in Section 5.1.1.

In some embodiments, neutropenia is immune-mediated, including autoimmune or alloimmune (e.g., caused by a non-self antigen that stimulates antibody formation and causes a hypersensitive reaction).

In various embodiments, the methods of promoting neutrophil production are useful for treating a subject diagnosed with radiation-induced neutropenia caused by radiation therapy or by non-therapeutic exposure to ionizing radiation, for example as a result of a radiological or nuclear accident or attack.

The methods of promoting neutrophil production are also useful for treating non-neutropenic subjects. Suitable subjects include those described above in Section 5.1.2. Such methods are particularly useful where the subject would benefit from an increased neutrophil count. In exemplary embodiments, the subject has been diagnosed with cancer, and/or is in need of surgery, or therapy with a treatment regimen having a myelosuppressive side effect. In some embodiments, the subject is at risk for radiation-induced neutropenia due to radiation therapy or non-therapeutic exposure to ionizing radiation, for example as a result of a radiological or nuclear accident or attack. In some embodiments, the subject is at increased risk of contracting an infection.

5.3.1. Additional Agents and Therapy

In the methods of promoting neutrophil production, the PF4-interacting heparinoid can be administered either as a sole agent or in adjunctive combination with one or more additional agents or therapies. In some embodiments, the one or more additional agents or therapy are capable of promoting neutrophil production. In various embodiments, the one or more additional agents or therapies are anti-coagulating.

Suitable therapies or agents to promote neutrophil production include agents that act to increase absolute neutrophil count. In exemplary embodiments, the one or more additional agent is selected from recombinant human granulocyte colony stimulating factor ("G-CSF") (filgrastim (Neupogen), pegfilgrastim (Neulasta)) and recombinant human granulocyte-macrophage colony stimulating factor ("GM-CSF") (sargramostim (Leukine)).

In some clinical situations, the patient may need anti-coagulation therapy. Thus, in some embodiments, the PF4-interacting heparinoid is administered adjunctive to one or more anti-coagulating agents, preferably without inducing or triggering heparin-induced thrombocytopenia. Anti-coagulation agents for use in such embodiments include, for example, heparins, such as unfractionated heparin, and low molecular weight heparin, such as dalteparin, enoxaparin, fondaparinux, reviparin, tinzaperin. In various embodiments, the PF4-interacting heparinoid and the anti-coagulant are administered in ratios in which the amount of PF4-interacting heparinoid exceeds the amount of anti-coagulant. Molar ratios of PF4-interacting heparinoid to anticoagulant heparin range from about 1:2 to about 10:1. Equivalent weight ratios are also contemplated.

Other suitable additional agents and therapies are described in Section 5.1.3 above.

5.4. Method of Increasing Efficacy of Treatment Regimens with Myelosuppressive Side Effects Myelosuppressive side effects such as thrombocytopenia and neutropenia that are caused by patient treatment regimens can be dose-limiting, limiting either the dose amount, the frequency of administration, or both, thereby decreasing the efficacy of the patient treatment regimen. Attenuating such myelosuppressive side effects would permit the dose amount and/or frequency of treatment to be maintained or increased, which should in turn lead to greater efficacy of the patient treatment regimen. As shown in Example 3 below, ODSH, a PF4-interacting heparinoid, attenuated the myelosuppressive side effects caused by an antineoplastic treatment regimen for pancreatic cancer; in particular, administering ODSH adjunctively with the chemotherapy treatment increased both platelet and neutrophil counts above those before treatment. Thus, administration of a PF4-interacting heparinoid adjunctively with such a treatment regimen should permit the dose amount and/or frequency of treatment to be maintained or increased, thereby increasing efficacy of the patient treatment regimen.

Consequently, in another aspect, methods for increasing efficacy of a treatment regimen with a myelosuppressive effect are provided. The methods comprise administering a therapeutically effective amount of a PF4-interacting heparinoid to the subject patient as an adjunct to the patient treatment regimen having myelosuppressive side effect, such as the ICE regimen, without reducing the dose and/or dosage frequency of the myelosuppressive patient treatment following a reference treatment administration or treatment cycle. In some embodiments, the reference treatment administration or cycle is the first treatment administration or treatment cycle. In various embodiments, the reference treatment administration or treatment cycle of the patient treatment regimen is subsequent to the first treatment administration or treatment cycle.

In some embodiments, the method further comprises administering a dose higher than is typically used for such administration or cycle in the absence of adjunctive administration of a PF4-interacting heparinoid.

In some embodiments, the methods further comprise determining an initial platelet and/or neutrophil count in a sample of blood from a patient.

In various embodiments, the PF4-interacting heparinoid is administered in an amount that is effective to raise the patient's platelet and/or neutrophil count above a prior-determined threshold level. In certain embodiments, the prior-determined threshold level is the level below which administration of the patient treatment regimen having a myelosuppressive side effect is contraindicated. Suitable modes of administration and dosing regimens are described further below, in Section 5.8. Effective dosages, and therapeutically effective amounts, of PF4-interacting heparinoid are described further below, in Section 5.9.

In certain embodiments, the methods comprise determining an initial platelet count in a sample from a patient, and then administering an amount of a PF4-interacting heparinoid effective to raise the patient's platelet count above a threshold level below which therapy with a patient treatment regimen having a myelosuppressive side effect is contraindicated. In various embodiments, an amount of a PF4-interacting heparinoid is administered sufficient to maintain platelet levels above levels that indicate grade 4 or grade 3 thrombocytopenia. In various embodiments, an amount of a PF4-interacting heparinoid is administered sufficient to maintain platelet levels above levels that indicate grade 2 or grade 1 thrombocytopenia. Optionally, the methods can further comprise administering adjunctively to the PF4-interacting heparinoid one or more agents or therapies that is anti-thrombocytopenic, anti-neutropenic, anticoagulant, or has some other therapeutic activity. In some embodiments, the methods comprise a further step of administering a patient treatment regimen having a myelosuppressive side effect to the patient whose platelet count is above a level that contraindicates such therapy. Optionally, the dose amount and/or frequency of the patient treatment regimen can be increased.

In certain embodiments, the methods comprise determining an initial neutrophil count in a blood sample from a patient and administering an amount of a PF4-interacting heparinoid effective to raise the patient's neutrophil count above a threshold level below which therapy with patient treatment regimen having a myelosuppressive side effect is contraindicated. In various embodiments, an amount of a PF4-interacting heparinoid is administered sufficient to maintain neutrophil levels above levels that indicate of grade 4 or grade 3 neutropenia, i.e., above about 1000 neutrophils/µl of blood and above about 500 neutrophils/µl of blood. In various embodiments, an amount of a PF4-interacting heparinoid is administered sufficient to maintain neutrophil levels above levels that indicate of grade 2 or grade 1 neutropenia. Optionally, the methods can further comprise administering adjunctive to the PF4-interacting heparinoid one or more agents or therapies that is anti-neutropenic, anti-thrombocytopenic, anticoagulant, or has some other therapeutic activity. In some embodiments, the methods comprise a further step of administering a patient treatment regimen having a myelosuppressive side effect to the patient whose neutrophil count is above a level that contraindicates such therapy. Optionally, the dose amount and/or frequency of the patient treatment regimen can be increased.

5.5. Method of Enhancing Efficacy of Antineoplastic Patient Treatment Regimens It has been discovered that adjunctive administration of ODSH, a PF4-interacting heparinoid, enhances the ability of antineoplastic treatment regimens to inhibit tumor growth. As shown in Examples 1 and 2 below, adjunctive administration of ODSH results in greater inhibition of tumor growth in murine xenograft models of pancreatic and ovarian cancer, than administration of either ODSH or a chemotherapeutic treatment regimen alone. Thus, in another aspect, methods are provided herein for enhancing the efficacy of an antineoplastic treatment regimen. The methods comprise administering a therapeutically effective amount of a PF4-interacting heparinoid to a subject patient as an adjunct to an antineoplastic treatment regimen.

Antineoplastic treatment regimens are patient treatment regimens useful in treating cancer. Suitable antineoplastic treatment regimens include chemotherapeutic treatment regimens (including induction chemotherapy and consolidation chemotherapy), antibody treatment regimens, and combinations thereof, as described further in Section 5.1.1 above.

The subject to be treated may be any animal, for example a mammal, preferably a human. In certain embodiments, the subject is an adult. In certain embodiments, the subject is a child. Subjects to be treated are patients in need of antineoplastic treatment, in particular patients suffering from, or diagnosed with, cancer. The cancer can be in any organ or tissue, including pancreatic cancer, ovarian cancer, uterine cancer, breast cancer, including metastatic breast cancer and chemotherapy-resistant breast cancer (e.g., breast cancer that recurs as a relapse within 6 months of adjuvant chemotherapy with or without an anthracycline), head and neck cancer, bladder cancer, urothelial cancer, lung cancer (including non-small cell lung cancer), colorectal cancer, gastric cancer, esophageal cancer, lymphoma (including recurrent, Hodgkin's, and non-Hodgkin's lymphomas), liver cancer, melanoma, prostate cancer, osteosarcoma and leukemia (including acute myelogenous leukemia and pediatric acute lymphoblastic leukemia).

The methods described herein are particularly useful for cancers in which PF4 levels are elevated either in platelets or in the blood. Thus, in some embodiments, the subject has been diagnosed with a cancer in which PF4 levels are elevated either in platelets or in the blood. In certain embodiments, the cancer is pancreatic cancer, colorectal cancer, osteosarcoma or leukemia (including acute myelogenous leukemia and pediatric acute lymphoblastic leukemia).

PF4-interacting heparinoids suitable for use in the methods are described below in Section 5.6. In an exemplary embodiment, the PF4-interacting heparinoid is ODSH. Suitable modes of administration and dosing regimens are described further below, in Section 5.8. Effective dosages and therapeutically effective amounts of PF4-interacting heparinoid are described further below, in Section 5.9.

5.6. PF4-Interacting Heparinoids

The heparinoids for use in the methods described herein are heparinoids that are capable of interacting with PF4, and counteracting PF4's ability to suppress production of platelets and neutrophils. As used herein, PF4-interacting heparinoids include heparinoids which bind PF4 and heparinoids which compete with PF4 for binding to progenitor cells in the myeloid cell lineage, e.g., megakaryocytes. A specific assay for binding of a heparinoid to PF4 is provided in Joglekar et al., 2012, *Thromb Haemost* 107(4):717-725, the disclosure of which is incorporated by reference herein. In some embodiments, a PF4-interacting heparinoid is a heparinoid that competes for binding to PF4 with unfractionated heparin, as determined by a competition assay, see e.g., Stringer et al., 1997, *J. Biol. Chem.* 272(33) 20508-20514, the disclosure of which is incorporated by reference herein.

PF4-interacting heparinoids are linear glycosaminoglycan polymers made up of alternating or repeating iduronic acid and glucosamine units bearing O-sulfate, N-sulfate, and N-acetyl substitutions. Preferably, PF4-interacting heparinoids for use in the methods described herein are polymers having an average molecular weight of at least about 8 kDa, for example having an average molecular weight ranging from about 8 kDa to about 15 kDa. In certain embodiments, the PF4-interacting heparinoids have an average molecular weight of greater than about 8 kDa. More preferably, PF4-interacting heparinoids for use in the methods described herein have an average molecular weight that ranges in size from about 11 kDa to about 13 kDa. Molecular weight of heparinoids can be determined by high performance size exclusion chromatography as is known in the art. See, e.g., Lapierre et al., 1996, *Glycobiology* 6(3):355-366, at page 363; Fryer et al., 1997, *J. Pharmacol. Exp. Ther.* 282: 208-219, at page 209.

Optionally, the PF4-interacting heparinoid does not cause platelet activation and heparin-induced thrombocytopenia (HIT), and is therefore useful for treating subjects at risk of heparin-induced thrombocytopenia, including subjects with antibodies against a PF4/heparin complex. Thus, in various embodiments, the PF4-interacting heparinoid does not trigger platelet activation that leads to heparin-induced thrombocytopenia; platelet activation can be determined using a serotonin release assay, as described in U.S. Pat. No. 7,468,358 and Sheridan et al., 1986, *Blood* 67:27-30. In some embodiments, the PF4-interacting heparinoid binds PF4 but is not recognized by anti-heparin-PF4 complex antibodies, even when complexed with PF4.

In various preferred embodiments, the PF4-interacting heparinoid is substantially nonanticoagulant. Anti-coagulation activity can be determined using assays known in the art, e.g., activated partial thromboplastin time (aPTT), prothrombin time, anti-$X_a$ clotting and amidolytic assays. See, e.g., U.S. Pat. No. 5,668,118, Example IV; Fryer et al., 1997, *J. Pharmacol. Exp. Ther.* 282: 208-219, at page 209; Rao et al., 2010, *Am. J. Physiol.* 299:C97-C110, at page C98; United States Pharmacopeial Convention 1995 (for USP anticoagulant assay and amidolytic assay).

In typical embodiments, the PF4-interacting heparinoids are partially desulfated. Preferably, the PF4-interacting heparinoids are substantially desulfated at the 2-O position of α-L-iduronic acid (referred to herein as the "2-O position") and/or desulfated at the 3-O position of D-glucosamine-N-sulfate (6-sulfate) (referred to herein as the "3-O position"). In some embodiments, the PF4-interacting heparinoids are at least 85%, at least 90%, at least 95%, or at least 99% desulfated at the 2-O position. In some preferred embodiments, the PF4-interacting heparinoids are at least 99% desulfated at the 2-O position. In some embodiments, the PF4-interacting heparinoids are at least 85%, at least 90%, at least 95%, or at least 99% desulfated at the 3-O position. In some preferred embodiments, the PF4-interacting heparinoids are at least 99% desulfated at the 3-O position. In some embodiments, the PF4-interacting heparinoids are at least 85%, at least 90%, at least 95%, at least 99% desulfated at the 2-O position and the 3-O position. In some preferred embodiments, the PF4-interacting heparinoids are at least 99% desulfated at the 2-O position and the 3-O position.

In typical embodiments, the PF4-interacting heparinoid comprises substantially N-sulfated and 6-O sulfated D-glucosamine. In some embodiments, the carboxylates on α-L-iduronic acid sugars of PF4-interacting heparinoid are substantially intact.

An exemplary PF4-interacting heparinoid is substantially 2-O, 3-O desulfated heparin, referred to herein as ODSH. ODSH for use in the above-described methods can be prepared from bovine or porcine heparin. In an exemplary method of preparing ODSH from porcine heparin, ODSH is synthesized by cold alkaline hydrolysis of USP porcine intestinal heparin, which removes the 2-O and 3-O sulfates, leaving N- and 6-O sulfates on D-glucosamine sugars and carboxylates on α-L-iduronic acid sugars substantially intact. Fryer, A. et al., 1997, *J. Pharmacol. Exp. Ther.* 282: 208-219. Using this method, ODSH can be produced with an average molecular weight of about 11.7±0.3 kDa.

In contrast to unfractionated heparin, ODSH is substantially non-anticoagulating: administered to a subject at a dose that is equivalent to a fully-anticoagulating dose of unfractionated heparin, the clotting time measured in an aPTT assay is no greater than 45 seconds, and typically in the upper range of normal, where normal clotting time ranges from about 27 to 35 seconds. By comparison, unfractionated heparin administered to a subject at a fully anticoagulant dose causes time to clot to range from about 60 to about 85 seconds in an aPTT assay. Another measure of ODSH's anticoagulant activity is its anti-$X_a$ activity which can be determined in an assay carried out using plasma treated with Russell viper venom. In specific examples, ODSH exhibited less than 9 U of anticoagulant activity/mg in the USP anticoagulant assay (e.g., 7±0.3 U), less than 5 U of anti-$X_a$ activity/mg (e.g., 1.9±0.1 U/mg) and less than 2 U of anti-$II_a$ activity/mg (e.g., 1.2±0.1

U/mg) (compare to unfractionated heparin which has an activity of 165-190 U/mg in all three assays). See Rao et al., 2010, *Am. J. Physiol.* 299:C97-C110, page C101. Whether or not a heparinoid is substantially non-anticoagulating can be determined using any of the above assays. Furthermore, ODSH has a low affinity for anti-thrombin III (Kd~339 μM or 4 mg/ml vs. 1.56 μM or 22 μg/ml for unfractionated heparin), consistent with the observed low level of anticoagulant activity, measured as described in Rao et al., supra, at page C98.

Methods for the preparation of 2-O, 3-O desulfated heparin may also be found, for example, in U.S. Pat. Nos. 5,668,118, 5,912,237, and 6,489,311, and WO 2009/015183, the contents of which are incorporated herein in their entirety, and in U.S. Pat. Nos. 5,296,471, 5,969,100, and 5,808,021.

5.7. Pharmaceutical Compositions and Unit Dosage Forms

In typical embodiments, the PF4-interacting heparinoid will be administered in the form of a pharmaceutical formulation or composition. Pharmaceutical compositions, suitable for administration to subjects, may optionally include additional active and/or therapeutic agents, as is known in the art. See Remington: The Science and Practice of Pharmacy, $21^{st}$ Ed. (2005), Lippincott Williams & Wilkins, incorporated herein by reference. The formulations will typically include one or more pharmaceutically acceptable carriers, excipients, or diluents. The specific carriers, excipients, and/or diluents used will depend on the desired mode of administration.

In various embodiments, the pharmaceutical compositions is in the form of a sterile, non-pyrogenic, fluid composition.

The pharmaceutical compositions can be formulated for administration to subjects by a variety of routes, including intranasally, by inhalation, intramuscularly, intraperitoneally, and parenterally, including intravenously or subcutaneously. Pharmaceutical compositions can be formulated in volumes and concentrations suitable for bolus administration, for continuous infusion, or for subcutaneous administration.

Pharmaceutical compositions can be conveniently presented in unit dosage forms which contain a predetermined amount of PF4-interacting heparinoid. In various embodiments, unit dosage forms of PF4-interacting heparinoid contain 1 mg to 1 g, or 5 mg to 500 mg of PF4-interacting heparinoid.

5.8. Modes of Administration

PF4-interacting heparinoids can be administered in the methods described herein by a variety of routes, as noted above. In presently preferred embodiments, the PF4-interacting heparinoid is administered intravenously, either as one or more boluses, as a continuous infusion, or as one or more boluses followed by continuous infusion.

In a variety of embodiments, PF4-interacting heparinoid is administered for a period of 1 day to indefinitely, a period of 1 week to 6 months, a period of 3 months to 5 years, a period of 6 months to 1 or 2 years, or the like. Optionally, PF4-interacting heparinoid administration is repeated; for example, in certain embodiments, PF4-interacting heparinoid is administered once daily, twice daily, three times daily, four times daily, five times daily, every two days, every three days, every five days, once a week, once every two weeks, once a month, every other month, semi-annually, or annually. In certain embodiments, PF4-interacting heparinoid is administered at regular intervals over a period of several weeks, followed by a period of rest, during which no PF4-interacting heparinoid is administered. For example, in certain embodiments, PF4-interacting heparinoid is administered for one, two, three, or more weeks, followed by one, two, three, or more weeks without PF4-interacting heparinoid administration. The repeated administration can be at the same dose or at a different dose. PF4-interacting heparinoid can be administered in one or more bolus injections, one or more infusions, or one or more bolus injections followed or preceded by infusion.

In embodiments in which PF4-interacting heparinoid is administered adjunctively to a patient treatment regimen having a myelosuppressive regimen, and/or adjunctively to administration of one or more additional agent(s) or therap(ies) having anti-thrombocytopenic, pro-thrombopoietic, anti-neutropenic, and/or pro-granulopoietic activity, the PF4-interacting heparinoid is administered in therapeutically effective temporal proximity to the treatment regimen having a myelosuppressive side effect and/or additional agent or therapy. Administration of a PF4-interacting heparinoid can be concurrent with (at the same time), sequential to (at a different time but on the same day, e.g., during the same patient visit), or separate from (on a different day) administration of the patient treatment regimen having a myelosuppressive side effect or other agent or therapy. In various embodiments, the adjunctively administered PF4-interacting heparinoid is administered concurrently, sequentially, and/or separately from the patient treatment regimen having myelosuppressive side effect or other agent or therapy being administered. When administered sequentially or separately, PF4-interacting heparinoid can be administered before, after, or both before and after the other treatment.

In embodiments in which PF4-interacting heparinoid is administered adjunctively, the PF4-interacting heparinoid can be administrated via the same or different route as the other treatment administered in temporal proximity. In various embodiments, PF4-interacting heparinoid is administered concurrently or sequentially by the same route. For example, in certain embodiments, PF4-interacting heparinoid and other treatment are administered intravenously, either concurrently or sequentially. Optionally, as part of a treatment regimen, the PF4-interacting heparinoid can further be administered separately (on a different day) from the other treatment by a different route, e.g., subcutaneously. In specific embodiments, PF4-interacting heparinoid is administered intravenously on the same day, either at the same time (concurrently), a different time (sequentially), or both concurrently and sequentially with other treatment, and is also administered subcutaneously on one or more days when the patient is not receiving other treatment. In various embodiments, PF4-interacting heparinoid is administered concurrently or sequentially by a different route. Optionally, as part of a treatment regimen, the PF4-interacting heparinoid can further be administered separately (on a different day) from the other treatment by the same or different route as that by which the other treatment is administered.

In one embodiment, PF4-interacting heparinoid is administered on days 1, 8, and 15 of a 28-day chemotherapy cycle as an initial bolus followed by a 48-hour continuous infusion. The course of treatment can further include administration of one or more chemotherapeutic agents sequentially before or after PF4-interacting heparinoid. Optionally, PF4-interacting heparinoid is administered subcutaneously on day 21 and/or one, several, or all of days 2, 3, 4, 5, 6, 7, 9, 10, 11, 12, 13, 14, 16, 17, 18, 19, 20, 21, 22, 23, 24, 25, 26, and 27.

5.9. Effective Dosages

PF4-interacting heparinoid is administered to the subject in an amount sufficient or effective to provide a therapeutic benefit, i.e., a therapeutically effective amount. The therapeutically effective amount depends on the therapeutic benefit that is sought—e.g., attenuation of myelosuppressive side effects such as thrombocytopenia and neutropenia, and/or promotion of thrombopoiesis, and/or promotion of granulopoiesis, and/or enhancement of antineoplastic effect.

In methods in which PF4-interacting heparinoid is administered to attenuate a myelosuppressive side effect of a patient treatment regimen, a myeloprotective amount of PF4-interacting heparinoid is administered, that is, an amount sufficient, in typical embodiments, to achieve one or more of the following, as compared to historical data on the identical patient treatment regimen without adjunctive administration of PF4-interacting heparinoid:

(a) thrombocytopenia is improved by at least one grade (e.g., from grade 4 to grade 3, 2, 1, or 0; from grade 3 to grade 2, 1, or 0; from grade 2 to grade 1 or 0; or from grade 1 to grade 0);

(b) platelet count is increased by at least 10%, at least 20%, at least 30%, at least 40%, at least 50%, at least 100%, at least 200%;

(c) platelet count is increased by at least 5,000, at least 10,000, at least 15,000, at least 20,000, at least 25,000, at least 30,000 platelets per µl of blood;

(d) neutropenia is improved by at least one grade (e.g., from grade 4 to grade 3, 2, 1, or 0; from grade 3 to grade 2, 1, or 0; from grade 2 to grade 1 or 0; or from grade 1 to grade 0);

(f) absolute neutrophil count is increased by at least 10%, at least 20%, at least 30%, at least 40%, at least 50%, at least 100%, at least 200%;

(d) absolute neutrophil count has increased by at least 500, at least 1000, at least 1500, at least 2000, at least 2500, at least 3000 neutrophils per µl of blood.

In particular embodiments, an amount of PF4-interacting heparinoid is administered sufficient to achieve one or more of the above-described effects as compared to pre-treatment levels.

In methods in which PF4-interacting heparinoid is administered to promote thrombopoiesis, a thrombopoietically-effective amount of a PF4-interacting heparinoid is, in typical embodiments, an amount effective to cause a measureable rise a subject's platelet count as compared to pre-treatment levels.

In methods in which PF4-interacting heparinoid is administered to promote neutrophil production, a granulopoietically-effective amount of a PF4-interacting heparinoid is, in typical embodiments, an amount effective to cause a measureable rise a subject's absolute neutrophil count as compared to pre-treatment levels.

In methods in which PF4-interacting heparinoid is administered to enhance efficacy of an antineoplastic treatment regimen, a therapeutically effective amount of a PF4-interacting heparinoid is an amount effective or sufficient to provide a therapeutic benefit. In the context of enhancing the efficacy of an antineoplastic treatment regimen, in various embodiments, a therapeutic benefit is achievement of one or more of the following: halting or slowing the growth of tumors, reducing the size and/or number of tumors within a patient, increasing life expectancy, reduction in constitutional side effects of the antineoplastic treatment (e.g., weight loss, loss of appetite, nausea, vomiting, fatigue), permitting reduction in dosage or frequency of dosage of the antineoplastic treatment regimen without reduced efficacy, and/or improving patient quality of life. A complete cure, while desirable, is not required for therapeutic benefit to exist. In some contexts, a therapeutic benefit can be correlated with one or more surrogate end points, in accordance with the knowledge of one of ordinary skill in the art. By way of example and not limitation, enhancing the efficacy of an antineoplastic treatment regimen can be measured in vivo. Exemplary in vivo assays for measuring tumor growth inhibition are described below for two different cancers and two different antineoplastic treatment regimens in Examples 1 and 2 below.

The amount of PF4-interacting heparinoid administered will depend on various factors, including whether the subject is thrombocytopenic and/or neutropenic, the severity of any such thrombocytopenia and/or neutropenia, whether PF4-interacting heparinoid is being administered adjunctively to a patient treatment regimen, and the age and condition of the subject being treated, among others. The appropriate dosage can be readily determined by a person of skill in the art. In practice, a physician will determine appropriate dosages to be used. This dosage can be repeated as often as appropriate. The amount and/or frequency of the dosage can be altered, increased, or reduced, depending on the subject's response and in accordance with standard clinical practice. The proper dosage and treatment regimen can be established by monitoring the progress of therapy using conventional techniques known to skilled artisans.

In some embodiments, PF4-interacting heparinoid is administered at a dose or amount per kilogram of patient body weight ranging from about 1 mg/kg to about 25 mg/kg for intravenous bolus doses, and from about 0.1 mg/kg/hr to about 2.5 mg/kg/hr for intravenous infusions. In a specific embodiment, PF4-interacting heparinoid is administered as an intravenous bolus at a dose of about 4 mg/kg, optionally followed by an intravenous infusion of PF4-interacting heparinoid at a dose of about 0.375 mg/kg/hr for 48 hours. In typical embodiments, a bolus dose is administered over less than a minute, about a minute, about 2 minutes, about 3 minutes, about 4 minutes, or about 5 minutes. For subcutaneous administration, PF4-interacting heparinoid can be administered at doses ranging from about 25 mg to about 400 mg, in volumes of 2.0 mL or less per injection site.

Pharmaceutical compositions of PF4-interacting heparinoid can be formulated in an amount that permits bolus intravenous administration and/or continuous intravenous infusion at such doses. In one embodiment, the pharmaceutical composition comprises PF4-interacting heparinoid in a sterile vial at a concentration of 50 mg/mL. When formulated for subcutaneous administration, pharmaceutical compositions can contain PF4-interacting heparinoid at a concentration ranging from 50 mg/ml to 350 mg/ml suitable for administration at doses ranging from about 25 to about 400 mg, in volumes of 2.0 mL or less per injection site.

6. EXAMPLES

6.1. Example 1: ODSH, a PF4-Interacting Heparinoid, Enhances the Efficacy of Gemcitabine in an In Vivo Murine Xenograft Model of Human Pancreatic Cancer and Demonstrates Antineoplastic Effect when Administered Alone This experiment demonstrates that adjunctive administration of ODSH enhances the efficacy of gemcitabine against human pancreatic tumors growing as xenografts in athymic nude mice, and demonstrates that ODSH inhibits tumor growth when administered alone.

Materials & Methods.

Compounds tested in the experiment were as follows. ODSH was made by Pyramid Laboratories, Inc. (Costa Mesa, Calif.). ODSH was provided at a stock concentration of 50 mg/ml and stored at room temperature until use. ODSH was diluted in a 0.9% NaCl solution (B. Braun Medical Inc., Irvine, Calif.) to a concentration of 2.4 mg/ml to deliver 24 mg/kg, in a 10 ml/kg dose volume when administered intravenously. A concentration of 4.8 mg/ml was formulated to deliver a 24 mg/kg dose at a 5 ml/kg dose volume when administered subcutaneously. ODSH was formulated fresh prior to each dose.

The chemotherapeutic agents oxaliplatin, gemcitabine, and nab-paclitaxel were also tested. Oxaliplatin was manufactured by Sanofi-Aventis (Bridgewater, N.J.) and diluted in a 0.9% NaCl solution to a concentration of 1 mg/ml to deliver 10 mg/kg, in a 10 ml/kg dose volume. Gemcitabine was manufactured by Eli Lilly and Co. (Indianapolis, Ind.) and diluted in a 0.9% NaCl solution to a concentration of 8 mg/ml to deliver 80 mg/kg, in a 10 ml/kg dose volume. Nab-paclitaxel was manufactured by Abraxis BioScience LLC (Bridgewater, N.J.) and diluted in a 0.9% NaCl solution to a concentration of 1.5 mg/ml to deliver 15 mg/kg, in a 10 ml/kg dose volume. All standard agent preparations were made fresh prior to their administration.

BxPC-3 cells were obtained and prepared as follows. The BxPC-3 pancreas tumor cell line was received from American Type Culture Collection (ATCC, Manassas, Va.). Cultures were maintained in RPMI 1640 medium (Hyclone, Logan, Utah) supplemented with 5% fetal bovine serum. The cells were housed in a 5% $CO_2$ atmosphere. The cultures were expanded in tissue culture flasks at a 1:3 split ratio until a sufficient amount of cells were harvested.

All experiments were conducted on female athymic nude mice (Hsd:Athymic Nude-Foxn1nu) supplied by Harlan (Indianapolis, Ind.). Mice were received at four weeks of age, 12-15 grams in weight, and were acclimated for seven days prior to handling. The mice were housed in microisolator cages (Lab Products, Seaford, Del.) and maintained under specific pathogen-free conditions. All procedures were carried out under appropriate institutional guidelines for animal care.

BxPC-3 Human Pancreas Tumor Xenograft Model: Female athymic nude mice per treatment condition were inoculated subcutaneously in the right flank with 0.1 ml of a 50% RPMI 1640/50% Matrigel™ (BD Biosciences, Bedford, Mass.) mixture containing a suspension of BxPC-3 tumor cells (approximately $5 \times 10^6$ cells/mouse).

Seven days following inoculation, tumors were measured using calipers and tumor weight was calculated using the animal study management software, Study Director V.1.7.54k (Study Log). See Britten C D, et al., "Enhanced antitumor activity of 6-hydroxymethylacylfulvene in combination with irinotecan and 5-fluorouracil in the HT29 human colon tumor xenograft model", Cancer Res 59:1049-1053, 1999. Eighty mice with tumor sizes of 93-172 mg were placed into eight groups of ten mice by random equilibration (Day 1). Body weights were recorded when the mice were randomized and were taken twice weekly thereafter in conjunction with tumor measurements, on each of Days 1, 4, 8, 11, 15, 18, 22, 26, 30, 33, and 36.

ODSH, vehicle control (0.9% NaCl solution, referred to as saline), oxaliplatin, gemcitabine, and nab-paclitaxel were administered according to the dosing regimen described in Table 1. The study was terminated when the vehicle control reached an endpoint of 1500 mg, on Day 36. Table 1, below, provides further details on the eight treatment groups.

TABLE 1

| Treatment group | Treatment | Agent administered | Dosing schedule and amount | Route* |
|---|---|---|---|---|
| 1 | Vehicle control | 0.9% saline | Twice a day, Day 1 to Day 11 | IV |
|  |  |  | Twice a day, Day 12 to Day 35 | SC |
| 2 | ODSH | 24 mg/kg | Twice a day, Day 1 to Day 11 | IV |
|  |  |  | Twice a day, Day 12 to Day 35 | SC |
| 3 | Oxaliplatin | 10 mg/kg | Once a week for 4 weeks (Days 1, 8, 15, 22) | IV |
|  | Gemcitabine | 80 mg/kg | Every three days for 3 administrations (Days 26, 29, 32) | IP |
|  | Nab-paclitaxel | 15 mg/kg | Every three days for 3 administrations (Days 26, 29, 32) | IV |
| 4 | Gemcitabine | 80 mg/kg | Every three days for 4 administrations (Days 1, 4, 7, 10) | IP |
| 5 | ODSH/ | 24 mg/kg | Twice a day, Day 1 to Day 11 | IV |
|  |  |  | Twice a day, Day 12 to Day 35 | SC |
|  | Oxaliplatin | 10 mg/kg | Once a week for 4 weeks (Days 1, 8, 15, 22) | IV |
|  | Gemcitabine | 80 mg/kg | Every three days for 4 administrations (Days 26, 29, 32, 35) | IP |
|  | Nab-paclitaxel | 15 mg/kg | Every three days for 3 administrations (Days 26, 29, 32) | IV |
| 6 | ODSH | 24 mg/kg | Twice a day, Day 1 to Day 11 | IV |
|  |  |  | Twice a day, Day 12 to Day 35 | SC |
|  | Gemcitabine | 80 mg/kg | Every three days for 4 administrations (Days 1, 4, 7, 10) | IP |
| 7 | Oxaliplatin | 10 mg/kg | Single administration (Day 1) | IV |
|  | Gemcitabine | 80 mg/kg | Every three days for 3 administrations (Days 1, 4, 7) | IP |
| 8 | ODSH | 24 mg/kg | Twice a day, Day 1 to Day 8 | IV |
|  | Oxaliplatin | 10 mg/kg | Single administration (Day 1) | IV |
|  | Gemcitabine | 80 mg/kg | Every three days for 3 administrations (Days 1, 4, 7) | IP |

*Agents were administered by one of three routes: intravenous (IV), subcutaneous (SC), or intraperitoneal (IP).

Treatment for Groups 7 and 8 was ceased on Day 8 due to adverse effects resulting from the treatment. The ODSH dosing route was modified from intravenous to subcutaneous on Day 12, as a result of tail swelling and bruising. Gemcitabine and nab-paclitaxel were introduced into the dosing regimen of Groups 3 and 5 on Day 26.

Data and statistical analyses were performed as follows. Mean tumor growth inhibition (TGI) was calculated utilizing Formula A below (deaths were not included in the TGI calculations). TGI calculations were performed comparing tumor weights of Day 26 to Day 1, which captures data prior to the addition of gemcitabine and nab-paclitaxel to several groups, and Day 36 (final day of study) to Day 1.

$$TGI = \left[1 - \frac{\left(\bar{X}_{Treated(Final)} - \bar{X}_{Treated(Day\,1)}\right)}{\left(\bar{X}_{Control(Final)} - \bar{X}_{Control(Day\,1)}\right)}\right] \times 100\% \quad \text{Formula A}$$

All statistical analyses in the xenograft study were performed with GraphPad Prism® v4 software. Differences in Day 26 and 36 tumor weights were confirmed using the Analysis of Variance (ANOVA) with the Tukey's Multiple Comparison Test.

Results.

The antitumor effects of ODSH administered as a single agent or in various combinations with one or more of oxaliplatin, gemcitabine, and nab-paclitaxel were evaluated.

The recorded tumor weights for experimental treatment groups 1 through 8 are provided below in Tables 2 through 9. See also FIG. 1.

TABLE 2

| Group 1 | | | | | | | | | | | |
|---|---|---|---|---|---|---|---|---|---|---|---|
| PBS Control (0 mg/kg) | | | | | Dose Route*: Intravenous/Subcutaneous Frequency: BID to end | | | | | | |
| Day: | 1 | 4 | 8 | 11 | 15 | 18 | 22 | 26 | 30 | 33 | 36 |
| Mouse 1 | 106 | 127 | 155 | 182 | 293 | 365 | 484 | 766 | 4161 | 4627 | 1,707 |
| Mouse 2 | 114 | 140 | 195 | 190 | 267 | 321 | 426 | 609 | 836 | 1,060 | 1379.03 |
| Mouse 3 | 106 | 119 | 166 | 194 | 223 | 300 | 420 | 635 | 1,067 | 1,306 | 1689.98 |
| Mouse 4 | 93 | 103 | 120 | 160 | 237 | 338 | 449 | 681 | 1,132 | 1,311 | 1565.56 |
| Mouse 5 | 140 | 145 | 207 | 249 | 306 | 346 | 546 | 780 | 1,020 | 1,230 | 1381.46 |
| Mouse 6 | 114 | 118 | 138 | 154 | 218 | 273 | 344 | 557 | 722 | 986 | 1295.65 |
| Mouse 7 | 129 | 159 | 200 | 194 | 282 | 321 | 461 | 681 | 1,054 | 1,286 | 1,352 |
| Mouse 8 | 130 | 122 | 134 | 176 | 272 | 320 | 415 | 583 | 999 | 1,165 | 1,329 |
| Mouse 9 | 142 | 153 | 164 | 184 | 318 | 333 | 465 | 590 | 1,080 | 1,341 | 1,522 |
| Mouse 10 | 172 | 194 | 259 | 285 | 377 | 505 | 665 | 915 | 1,362 | 1,620 | 2,020 |
| Mean | 124.6 | 138.1 | 173.7 | 196.9 | 279.2 | 342.2 | 467.6 | 679.8 | 1,043.2 | 1,293.3 | 1,524.2 |
| Median | 121.6 | 133.7 | 164.8 | 186.9 | 276.8 | 327.3 | 454.9 | 657.9 | 1,060.4 | 1,296.2 | 1,451.9 |
| Std Dev | 22.78 | 26.24 | 41.72 | 40.36 | 48.10 | 62.40 | 86.85 | 111.90 | 174.53 | 208.14 | 228.53 |
| Std Err | 7.20 | 8.30 | 13.19 | 12.76 | 15.21 | 19.73 | 27.46 | 35.39 | 55.19 | 65.82 | 72.27 |

*ODSH dosed intravenously Days 1-11; dosed subcutaneously Days 12-end

TABLE 3

| Group 2 | | | | | | | | | | | |
|---|---|---|---|---|---|---|---|---|---|---|---|
| ODSH (24 mg/kg) | | | | Dose Route*: Frequency: | | | Intravenous/Subcutaneous BID to end | | | | |
| Day: | 1 | 4 | 8 | 11 | 15 | 18 | 22 | 26 | 30 | 33 | 36 |
| Mouse 1 | 143 | 144 | 157 | 140 | 218 | 278 | 326 | 394 | 555 | 733 | 836 |
| Mouse 2 | 129 | 133 | 148 | 203 | 264 | 352 | 515 | 766 | 1,109 | 1,340 | 1,823 |
| Mouse 3 | 140 | 162 | 218 | 149 | 206 | 278 | 358 | 509 | 697 | 908 | 1,072 |
| Mouse 4 | 114 | 98 | 118 | 288 | 340 | 489 | 622 | 894 | 1,083 | 1,218 | 1,450 |
| Mouse 5 | 116 | 110 | 144 | 142 | 224 | 291 | 360 | 478 | 756 | 999 | 1,153 |
| Mouse 6 | 172 | 141 | 183 | 175 | 263 | 288 | 400 | 529 | 893 | 961 | 1,150 |
| Mouse 7 | 94 | 97 | 125 | 243 | 348 | 419 | 556 | 770 | 1,201 | 1,309 | 1,654 |
| Mouse 8 | 131 | 181 | 222 | 146 | 237 | 256 | 402 | 573 | 820 | 961 | 1,150 |
| Mouse 9 | 106 | 135 | 126 | 252 | 321 | 415 | 551 | 724 | 945 | 1,087 | 1,376 |
| Mouse 10 | 125 | 130 | 155 | 137 | 208 | 318 | 449 | 524 | 764 | 871 | 1,037 |
| Mean | 122.4 | 134.0 | 146.0 | 187.6 | 263.0 | 338.5 | 453.8 | 616.2 | 882.3 | 1,038.6 | 1,270.1 |
| Median | 22.9 | 28.6 | 40.4 | 162.1 | 250.0 | 304.7 | 425.4 | 551.3 | 856.4 | 979.8 | 1,151.5 |
| Std Dev | 7.24 | 9.03 | 12.76 | 55.55 | 54.66 | 77.75 | 101.08 | 160.86 | 203.52 | 197.30 | 302.01 |
| Std Err | | | | 17.57 | 17.29 | 24.59 | 31.96 | 50.87 | 64.36 | 62.39 | 95.50 |

*ODSH dosed intravenously Days 1-11; dosed subcutaneously Days 12-end

TABLE 4

| Group 3^ | | | | | | | | | | | |
|---|---|---|---|---|---|---|---|---|---|---|---|
| Oxaliplatin 10 mg/kg | | | Dose Route: Frequency: | | Intravenous Wkly x 4 (Day 1, 8, 15, 22) | | | | | | |
| Gemcitabine 80 mg/kg | | | Dose Route: Frequency: | | Intraperitoneal Day 26, 39, 32 (Q3dx3 starting Day 26) | | | | | | |
| Nab/paclitaxel 15 mg/kg | | | Dose Route: Frequency: | | Intravenous Day 26, 29, 32 (2x weekly starting Day 26) | | | | | | |
| Day: | 1 | 4 | 8 | 11 | 15 | 18 | 22 | 26 | 30 | 33 | 36 |
| Mouse 1 | 113 | 144 | 154 | 202 | 271 | 300 | 392 | 570 | 725 | FD | FD |
| Mouse 2 | 131 | 135 | 219 | 184 | 250 | 269 | 322 | 397 | 393 | MS | MS |
| Mouse 3 | 104 | 113 | 142 | 164 | 219 | 289 | 379 | 487 | 595 | FD | FD |
| Mouse 4 | 143 | 148 | 205 | 265 | 368 | 485 | 611 | 812 | FD | FD | FD |
| Mouse 5 | 168 | 169 | 245 | 299 | 394 | 533 | 673 | 918 | FD | FD | FD |
| Mouse 6 | 128 | 114 | 167 | 201 | 282 | 314 | 451 | 522 | 658 | FD | FD |
| Mouse 7 | 96 | 126 | 161 | 211 | 263 | 362 | 432 | 629 | 687 | FD | FD |
| Mouse 8 | 116 | 136 | 205 | 243 | 308 | 461 | 666 | 824 | 926 | FD | FD |
| Mouse 9 | 106 | 139 | 165 | 222 | 301 | 371 | 522 | 600 | 706 | MS | MS |

TABLE 4-continued

| | | | | | Group 3^ | | | | | | |
|---|---|---|---|---|---|---|---|---|---|---|---|
| Mouse 10 | 139 | 133 | 157 | 217 | 282 | 394 | 495 | 589 | 689 | MS | MS |
| Mean | 124.5 | 135.7 | 182.0 | 220.6 | 293.7 | 377.6 | 494.4 | 635.0 | 672.2 | | |
| Median | 121.9 | 135.7 | 165.8 | 213.6 | 282.0 | 366.4 | 473.1 | 594.5 | 688.0 | | |
| Std Dev | 21.78 | 16.25 | 33.99 | 39.41 | 52.76 | 90.07 | 122.52 | 165.28 | 147.79 | | |
| Std Err | 6.89 | 5.14 | 10.75 | 12.46 | 16.68 | 28.48 | 38.74 | 52.26 | 52.25 | | |

^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)

TABLE 5

| | | | | | Group 4 | | | | | | |
|---|---|---|---|---|---|---|---|---|---|---|---|
| Gemcitabine 80 mg/kg | | | | Dose Route:<br>Frequency: | | | Intraperitoneal<br>Q3d x 4 (Day 1, 4, 7, 10) | | | | |
| Day: | 1 | 4 | 8 | 11 | 15 | 18 | 22 | 26 | 30 | 33 | 36 |
| Mouse 1 | 146 | 155 | 180 | 234 | 300 | 389 | 500 | 647 | 992 | 1,158 | 1,267 |
| Mouse 2 | 96 | 135 | 134 | 180 | 274 | 304 | 404 | 583 | 826 | 1,008 | 1,265 |
| Mouse 3 | 132 | 189 | 193 | 235 | 319 | 413 | 621 | 797 | 1,121 | 1,367 | 1,573 |
| Mouse 4 | 139 | 214 | 282 | 328 | 375 | 379 | 514 | 739 | 1,008 | 1,132 | 1,368 |
| Mouse 5 | 126 | 126 | 129 | 146 | 211 | 258 | 372 | 468 | 674 | 878 | 963 |
| Mouse 6 | 104 | 122 | 114 | 145 | 218 | 267 | 400 | 534 | 860 | 1,036 | 1,347 |
| Mouse 7 | 107 | 131 | 130 | 119 | 181 | 224 | 350 | 431 | 667 | 936 | 1,106 |
| Mouse 8 | 111 | 133 | 125 | 150 | 228 | 269 | 332 | 389 | 589 | 624 | 923 |
| Mouse 9 | 116 | 146 | 161 | 202 | 245 | 441 | 592 | 730 | 1,150 | 1,275 | 1,596 |
| Mouse 10 | 166 | 176 | 175 | 242 | 288 | 376 | 509 | 628 | 856 | 1,030 | 1,482 |
| Mean | 124.3 | 152.5 | 162.2 | 198.2 | 263.8 | 332.1 | 459.4 | 594.7 | 874.3 | 1,044.2 | 1,288.8 |
| Median | 121.1 | 140.2 | 147.4 | 191.0 | 259.2 | 340.1 | 451.9 | 605.8 | 858.0 | 1,033.3 | 1,306.7 |
| Std Dev | 21.73 | 30.57 | 50.04 | 63.22 | 58.46 | 76.00 | 101.69 | 138.55 | 193.10 | 209.66 | 234.90 |
| Std Err | 6.87 | 9.67 | 15.83 | 19.99 | 18.49 | 24.03 | 32.16 | 43.81 | 61.06 | 66.30 | 74.28 |

TABLE 6

| | | | | | Group 5^ | | | | | | |
|---|---|---|---|---|---|---|---|---|---|---|---|
| ODSH 24 mg/kg | | | Dose Route*:<br>Frequency: | | Intravenous/Subcutaneous<br>BID to end | | | | | | |
| Oxaliplatin 10 mg/kg | | | Dose Route:<br>Frequency: | | Intravenous<br>Wkly x 4 (Day 1, 8, 15, 22) | | | | | | |
| Gemcitabine 80 mg/kg | | | Dose Route:<br>Frequency: | | Intraperitoneal<br>Day 26, 29, 32, 35 (Q3dx4 starting Day 26) | | | | | | |
| Nab/paclitaxel 15 mg/kg | | | Dose Route:<br>Frequency: | | Intravenous<br>Day 26, 29, 32 (2x weekly starting Day 26) | | | | | | |
| Day: | 1 | 4 | 8 | 11 | 15 | 18 | 22 | 26 | 30 | 33 | 36 |
| Mouse 1 | 139 | 144 | 207 | 237 | 395 | 448 | 571 | 819 | 908 | FD | FD |
| Mouse 2 | 103 | 106 | 172 | 230 | 298 | 372 | 403 | 609 | 735 | FD | FD |
| Mouse 3 | 160 | 162 | 166 | 205 | 279 | 337 | 484 | 635 | 758 | FD | FD |
| Mouse 4 | 97 | 113 | 108 | 113 | 160 | 173 | 225 | 313 | 359 | FD | FD |
| Mouse 5 | 125 | 134 | 174 | 163 | 245 | 299 | 421 | 576 | 772 | FD | FD |
| Mouse 6 | 117 | 137 | 124 | 165 | 229 | 259 | 334 | 416 | 552 | MS | MS |
| Mouse 7 | 148 | 191 | 186 | 184 | 286 | 337 | 470 | 642 | 745 | 891 | 828 |
| Mouse 8 | 108 | 136 | 141 | 198 | 280 | 386 | 539 | 766 | MS | MS | MS |
| Mouse 9 | 133 | 177 | 214 | 226 | 313 | 400 | 578 | 631 | 834 | FD | FD |
| Mouse 10 | 111 | 119 | 156 | 173 | 219 | 229 | 333 | 457 | FD | FD | 827.5 |
| Mean | 124.1 | 142.0 | 164.9 | 189.5 | 270.4 | 324.0 | 436.0 | 586.6 | 708.0 | 891.1 | 827.5 |
| Median | 121.2 | 136.4 | 169.2 | 191.2 | 279.4 | 336.7 | 445.8 | 620.2 | 751.6 | 891.1 | 877.5 |
| Std Dev | 20.52 | 27.53 | 34.05 | 37.97 | 62.97 | 84.34 | 115.23 | 154.52 | 173.64 | | |
| Std Err | 6.49 | 8.71 | 10.77 | 12.01 | 19.91 | 26.67 | 36.44 | 48.86 | 61.39 | | |

^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)
*ODSH dosed intravenously Days 1-11; dosed subcutaneously Days 12-end
MS = Moribund Sacrifice
FD = Found Dead

TABLE 7

Group 6

| ODSH 24 mg/kg | | | | Dose Route*: | | | Intravenous/Subcutaneous | | | |
|---|---|---|---|---|---|---|---|---|---|---|
| | | | | Frequency: | | | BID to end | | | |
| Gemcitabine 80 mg/kg | | | | Dose Route: | | | Intraperitoneal | | | |
| | | | | Frequency: | | | Q3d x 4 (Day 1, 4, 7, 10) | | | |

| Day: | 1 | 4 | 8 | 11 | 15 | 18 | 22 | 26 | 30 | 33 | 36 |
|---|---|---|---|---|---|---|---|---|---|---|---|
| Mouse 1 | 160 | 169 | 194 | 135 | 203 | 279 | 407 | 562 | 780 | 893 | 1,115 |
| Mouse 2 | 101 | 92 | 113 | 151 | 188 | 194 | 309 | 374 | 497 | 578 | 862 |
| Mouse 3 | 119 | 160 | 170 | 209 | 278 | 257 | 326 | 452 | 571 | 822 | 997 |
| Mouse 4 | 134 | 122 | 128 | 154 | 188 | 231 | 409 | 330 | 595 | 773 | 834 |
| Mouse 5 | 125 | 134 | 141 | 152 | 197 | 265 | 332 | 520 | 622 | 856 | 965 |
| Mouse 6 | 97 | 102 | 117 | 156 | 203 | 229 | 336 | 491 | 746 | 820 | 1,048 |
| Mouse 7 | 137 | 121 | 166 | 171 | 205 | 256 | 389 | 510 | 704 | 789 | 868 |
| Mouse 8 | 151 | 174 | 203 | 255 | 331 | 484 | 635 | 886 | 1,069 | 1,289 | 1,365 |
| Mouse 9 | 111 | 120 | 123 | 130 | 149 | 199 | 273 | 342 | 490 | 631 | 833 |
| Mouse 10 | 108 | 134 | 131 | 118 | 239 | 191 | 323 | 543 | 757 | 843 | 1,051 |
| Mean | 124.2 | 132.7 | 148.7 | 163.0 | 218.1 | 258.5 | 336.0 | 508.9 | 683.3 | 829.3 | 993.9 |
| Median | 121.7 | 128.1 | 136.1 | 153.3 | 203.0 | 243.2 | 331.0 | 500.3 | 663.0 | 820.9 | 981.0 |
| Std Dev | 20.92 | 27.40 | 32.50 | 40.78 | 52.12 | 85.24 | 101.65 | 151.31 | 171.22 | 189.79 | 164.57 |
| Std Err | 6.61 | 8.67 | 10.28 | 12.90 | 16.48 | 26.96 | 32.15 | 47.85 | 54.15 | 60.02 | 52.04 |

*ODSH dosed intravenously Days 1-11; dosed subcutaneously Days 12-end

TABLE 8

Group 7

| Oxaliplatin 10 mg/kg | | | | Dose Route: | | | Intravenous | | | |
|---|---|---|---|---|---|---|---|---|---|---|
| | | | | Frequency: | | | Day 1 | | | |
| Gemcitabine 80 mg/kg | | | | Dose Route: | | | Intraperitoneal | | | |
| | | | | Frequency: | | | Q3d x 3 (Day 1, 4, 7) | | | |

| Day: | 1 | 4 | 8 | 11 | 15 | 18 | 22 | 26 | 30 | 33 | 36 |
|---|---|---|---|---|---|---|---|---|---|---|---|
| Mouse 1 | 137 | 119 | 132 | 110 | MS | MS | MS | MS | MS | MS | MS |
| Mouse 2 | 159 | 175 | 165 | 197 | 259 | 368 | 453 | 527 | 735 | 787 | 877 |
| Mouse 3 | 110 | 104 | 107 | 137 | MS | MS | MS | MS | MS | MS | MS |
| Mouse 4 | 110 | 114 | 110 | 117 | MS | MS | MS | MS | MS | MS | MS |
| Mouse 5 | 135 | 117 | 81 | FD | FD | FD | FD | FD | FD | FD | FD |
| Mouse 6 | 97 | 98 | 103 | 106 | FD | FD | FD | FD | FD | FD | FD |
| Mouse 7 | 152 | 173 | 222 | 217 | 314 | 389 | 541 | 801 | 1,221 | 1,599 | 1,699 |
| Mouse 8 | 121 | 117 | 113 | FD | FD | FD | FD | FD | FD | FD | FD |
| Mouse 9 | 119 | 146 | 150 | 173 | 272 | 299 | 424 | 510 | 715 | 871 | 1,107 |
| Mouse 10 | 100 | 111 | 103 | FD | FD | FD | FD | FD | FD | FD | FD |
| Mean | 124.1 | 127.2 | 128.7 | 150.9 | 281.7 | 352.1 | 472.7 | 612.4 | 890.1 | 1,085.5 | 1,227.7 |
| Median | 120.1 | 116.6 | 111.8 | 136.8 | 272.0 | 368.5 | 452.8 | 526.9 | 734.8 | 870.9 | 1,107.0 |
| Std Dev | 21.16 | 27.63 | 41.13 | 44.59 | 29.01 | 47.57 | 60.91 | 163.25 | 286.32 | 446.77 | 423.84 |
| Std Err | 6.69 | 8.74 | 13.01 | 16.85 | 16.75 | 27.46 | 36.17 | 94.25 | 165.31 | 257.94 | 244.71 |

MS = Moribund Sacrifice
FD = Found Dead

TABLE 9

Group 8

| ODSH 24 mg/kg | | | | Dose Route*: | | | Intravenous/Subcutaneous | | | |
|---|---|---|---|---|---|---|---|---|---|---|
| | | | | Frequency: | | | BID X 8 days | | | |
| Oxaliplatin 10 mg/kg | | | | Dose Route: | | | Intravenous | | | |
| | | | | Frequency: | | | Day 1 | | | |
| Gemcitabine 80 mg/kg | | | | Dose Route: | | | Intraperitoneal | | | |
| | | | | Frequency: | | | Q3d x 3 (Day 1, 4, 7) | | | |

| Day: | 1 | 4 | 8 | 11 | 15 | 18 | 22 | 26 | 30 | 33 | 36 |
|---|---|---|---|---|---|---|---|---|---|---|---|
| Mouse 1 | 121 | 129 | 127 | FD | FD | FD | FD | FD | FD | FD | FD |
| Mouse 2 | 153 | 147 | 94 | FD | FD | FD | FD | FD | FD | FD | FD |
| Mouse 3 | 157 | 174 | 183 | FD | FD | FD | FD | FD | FD | FD | FD |
| Mouse 4 | 110 | 102 | 81 | FD | FD | FD | FD | FD | FD | FD | FD |
| Mouse 5 | 121 | 123 | FD | FD | FD | FD | FD | FD | FD | FD | FD |
| Mouse 6 | 110 | 124 | 127 | FD | FD | FD | FD | FD | FD | FD | FD |
| Mouse 7 | 99 | 82 | 121 | FD | FD | FD | FD | FD | FD | FD | FD |
| Mouse 8 | 135 | 152 | 148 | FD | FD | FD | FD | FD | FD | FD | FD |
| Mouse 9 | 136 | 159 | 215 | 196 | MS | MS | MS | MS | MS | MS | MS |

TABLE 9-continued

| | | | Group 8 | | | | | | | | |
|---|---|---|---|---|---|---|---|---|---|---|---|
| Mouse 10 | 99 | 118 | 122 | FD | FD | FD | FD | FD | FD | FD | FD |
| Mean | 124.1 | 131.0 | 135.4 | 196.0 | | | | | | | |
| Median | 121.0 | 126.3 | 127.0 | 196.0 | | | | | | | |
| Std Dev | 20.79 | 27.70 | 4.84 | | | | | | | | |
| Std Err | 6.57 | 8.76 | 13.95 | | | | | | | | |

FD = Found Dead
MS = Moribund Sacrifice
*ODSH dosed intravenously Days 1-11; dosed subcutaneously Days 12-end ^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)

Tables 10 to 13 below show the body weights recorded for treatment groups 1 to 8 over the course of the experiment. See also FIG. 3.

TABLE 10

| | | | | | Day 1 | | Day 4 | | | Day 8 | | |
|---|---|---|---|---|---|---|---|---|---|---|---|---|
| Group | Compound | Dosage | Frequency | Dose Route*: | Starting Weight (g) | # Mice | Average Weight (g) | # Mice | Average Weight (g) | % Weight Loss or Gain | # Mice | Average Weight (g) | % Weight Loss or Gain |
| 1 | Vehicle Control | 0 mg/kg | BID to end | Intravenous/Subcutaneous | 20.86 | 10 | 20.86 | 10 | 20.48 | −1.82 | 10 | 20.67 | −0.91 |
| 2 | ODSH | 24 mg/kg | BID to end | Intravenous/Subcutaneous | 21.54 | 10 | 21.54 | 10 | 21.18 | −1.67 | 10 | 21.18 | −1.67 |
| 3^ | Oxaliplatin | 10 mg/kg | Wkly x4 (Day 1, 8, 15, 22) | Intravenous | 20.82 | 10 | 20.82 | 10 | 20.40 | −2.02 | 10 | 20.65 | −0.82 |
| 4 | Gemcitabine | 80 mg/kg | Q3dx4 (Day 1, 4, 7, 10) | Intraperitoneal | 22.48 | 10 | 22.48 | 10 | 21.76 | −3.20 | 10 | 20.91 | −6.98 |
| 5^ | ODSH + Oxaliplatin | 24 mg/kg + 10 mg/kg | BID to end + Wkly x4 (Day 1, 8, 15, 22) | Intravenous/Subcutaneous | 21.11 | 10 | 21.11 | 10 | 20.40 | −3.36 | 10 | 21.08 | −0.14 |
| 6 | ODSH + Gemcitabine | 24 mg/kg + 80 mg/kg | BID to end + Q3d x 4 (Day 1, 4, 7, 10) | Intravenous/Subcutaneous + Intravenous | 20.95 | 10 | 20.95 | 10 | 20.31 | −3.05 | 10 | 18.92 | −9.69 |
| 7 | Oxaliplatin + Gemcitabine | 10 mg/kg + 80 mg/kg | Day 1 + Q3d x 3 (Day 1, 4, 7) | Intravenous + Intravenous | 20.58 | 10 | 20.58 | 10 | 19.32 | −6.12 | 10 | 17.17 | −16.57 |
| 8 | ODSH + Oxaliplatin + Gemcitabine | 24 mg/kg + 10 mg/kg + 80 mg/kg | BID x 8 days + Day 1 + Q3d x 3 (Day 1, 4, 7) | Intravenous + Intravenous + Intraperitoneal | 20.96 | 10 | 20.96 | 10 | 18.88 | −9.92 | 9 | 15.50 | −26.05 |

^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)
*ODSH dosed intravenously Days 1-11; dosed subcutaneously Days 12-end

TABLE 11

| | | | | | Day 11 | | | Day 15 | | | Day 18 | | |
|---|---|---|---|---|---|---|---|---|---|---|---|---|---|
| Group | Compound | Dosage | Frequency* | Dose Route | # Mice | Average Weight (g) | % Weight Loss or Gain | # Mice | Average Weight (g) | % Weight Loss or Gain | # Mice | Average Weight (g) | % Weight Loss or Gain |
| 1 | Vehicle Control | 0 mg/kg | BID to end | Intravenous/Subcutaneous | 10 | 20.45 | −1.97 | 10 | 20.10 | −3.64 | 10 | 20.36 | −2.40 |
| 2 | ODSH | 24 mg/kg | BID to end | Intravenous/Subcutaneous | 10 | 20.95 | −2.74 | 10 | 21.08 | −2.14 | 10 | 21.04 | −2.32 |
| 3^ | Oxaliplatin | 10 mg/kg | Wkly x4 (Day 1, 8, 15, 22) | Intravenous | 10 | 20.12 | −3.36 | 10 | 20.81 | −0.05 | 10 | 20.45 | −1.78 |
| 4 | Gemcitabine | 80 mg/kg | Q3dx4 (Day 1, 4, 7, 10) | Intraperitoneal | 10 | 20.52 | −8.72 | 10 | 21.70 | −3.47 | 10 | 23.15 | 2.98 |

TABLE 11-continued

| Group | Compound | Dosage | Frequency* | Dose Route | Day 11 # Mice | Day 11 Average Weight (g) | Day 11 % Weight Loss or Gain | Day 15 # Mice | Day 15 Average Weight (g) | Day 15 % Weight Loss or Gain | Day 18 # Mice | Day 18 Average Weight (g) | Day 18 % Weight Loss or Gain |
|---|---|---|---|---|---|---|---|---|---|---|---|---|---|
| 5^ | ODSH + Oxaliplatin | 24 mg/kg + 10 mg/kg | BID to end + Wkly x4 (Day 1, 8, 15, 22) | Intravenous/ Subcutaneous + Intravenous | 10 | 19.79 | −6.25 | 10 | 19.87 | −5.87 | 10 | 19.49 | −7.67 |
| 6 | ODSH + Gemcitabine | 24 mg/kg + 80 mg/kg | BID to end + Q3d x 4 (Day 1, 4, 7, 10) | Intravenous/ Subcutaneous + Intravenous | 10 | 18.14 | −13.41 | 10 | 18.84 | −10.07 | 10 | 20.68 | −1.29 |
| 7 | Oxaliplatin + Gemcitabine | 10 mg/kg + 80 mg/kg | Day 1 + Q3d x 3 (Day 1, 4, 7) | Intravenous + Intravenous | 7 | 17.17 | −16.56 | 3 | 22.03 | 7.06 | 3 | 23.37 | 13.54 |
| 8 | ODSH + Oxaliplatin + Gemcitabine | 24 mg/kg + 10 mg/kg + 80 mg/kg | BID x 8 days + Day 1 + Q3d x 3 (Day 1, 4, 7) | Intravenous + Intravenous + Intraperitoneal | 1 | 14.80 | −29.39 | 0 | | | 0 | | |

^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)
*ODSH dosed intravenously Days 1-11; dosed subcutaneously Days 12-end

TABLE 12

| Group | Compound | Dosage | Frequency* | Dose Route | Day 22 # Mice | Day 22 Average Weight (g) | Day 22 % Weight Loss or Gain | Day 26 # Mice | Day 26 Average Weight (g) | Day 26 % Weight Loss or Gain | Day 30 # Mice | Day 30 Average Weight (g) | Day 30 % Weight Loss or Gain |
|---|---|---|---|---|---|---|---|---|---|---|---|---|---|
| 1 | Vehicle Control | 0 mg/kg | BID to end | Intravenous/ Subcutaneous | 10 | 20.81 | −0.24 | 10 | 20.93 | 0.34 | 10 | 21.28 | 2.01 |
| 2 | ODSH | 24 mg/kg | BID to end | Intravenous/ Subcutaneous | 10 | 21.56 | 0.09 | 10 | 22.14 | 2.79 | 10 | 22.60 | 4.92 |
| 3^ | Oxaliplatin Gemcitabine Nab-paclitaxel | 10 mg/kg 80 mg/kg 15 mg/kg | Wkly x4 (Day 1, 8, 15, 22) Day 26, 29, 32 Day 26, 29, 32 | Intravenous Intraperitoneal Intravenous | 10 | 21.27 | 2.16 | 10 | 20.96 | 0.67 | 8 | 18.08 | −13.18 |
| 4 | Gemcitabine | 80 mg/kg | Q3dx4 (Day 1, 4, 7, 10) | Intraperitoneal | 10 | 24.22 | 7.74 | 10 | 24.27 | 7.96 | 10 | 24.19 | 7.61 |
| 5^ | ODSH + Oxaliplatin Gemcitabine Nab-paclitaxel | 24 mg/kg + 10 mg/kg 80 mg/kg 15 mg/kg | BID to end + Wkly x4 (Day 1, 8, 15, 22) Day 26, 29, 32, 35 Day 26, 29, 32 | Intravenous/ Subcutaneous + Intravenous Intraperitoneal Intravenous | 10 | 20.47 | −3.03 | 10 | 20.51 | −2.84 | 8 | 18.16 | −13.96 |
| 6 | ODSH + Gemcitabine | 24 mg/kg + 80 mg/kg | BID to end + Q3d x 4 (Day 1, 4, 7, 10) | Intravenous/ Subcutaneous + Intravenous | 10 | 21.64 | 3.29 | 10 | 22.79 | 8.78 | 10 | 22.36 | 6.73 |
| 7 | Oxaliplatin + Gemcitabine | 10 mg/kg + 80 mg/kg | Day 1 + Q3d x 3 (Day 1, 4, 7) | Intravenous + Intravenous | 3 | 23.67 | 15.00 | 3 | 23.73 | 15.32 | 3 | 23.90 | 16.13 |
| 8 | ODSH + Oxaliplatin + Gemcitabine | 24 mg/kg + 10 mg/kg + 80 mg/kg | BID x 8 days + Day 1 + Q3d x 3 (Day 1, 4, 7) | Intravenous + Intravenous + Intraperitoneal | 0 | 0 | 0 | 0 | | | 0 | | |

^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)
*ODSH dosed intravenously Days 1-11; dosed subcutaneously Days 12-end

TABLE 13

| Group | Compound | Dosage | Frequency | Dose Route*: | # Mice | Day 22 Average Weight (g) | Day 22 % Weight Loss or Gain | # Mice | Day 26 Average Weight (g) | Day 26 % Weight Loss or Gain |
|---|---|---|---|---|---|---|---|---|---|---|
| 1 | Vehicle Control | 0 mg/kg | BID to end | Intravenous/Subcutaneous | 10 | 21.49 | 3.02 | 10 | 21.46 | 2.88 |
| 2 | ODSH | 24 mg/kg | BID to end | Intravenous/Subcutaneous | 10 | 22.53 | 4.60 | 10 | 22.46 | 4.27 |
| 3^ | Oxaliplatin Gemcitabine Nab-paclitaxel | 10 mg/kg 80 mg/kg 15 mg/kg | Wkly x4 (Day 1, 8, 15, 22) Day 26, 29, 32 Day 26, 29, 32 | Intravenous Intraperitoneal Intravenous | 0 | 0 | 0 | 0 | | |
| 4 | Gemcitabine | 80 mg/kg | Q3dx4 (Day 1, 4, 7, 10) | Intraperitoneal | 10 | 24.41 | 8.59 | 10 | 24.21 | 7.70 |
| 5^ | ODSH + Oxaliplatin Gemcitabine Nab-paclitaxel | 24 mg/kg + 10 mg/kg 80 mg/kg 15 mg/kg | BID to end + Wkly x4 (Day 1, 8, 15, 22) Day 26, 29, 32, 35 Day 26, 29, 32 | Intravenous/Subcutaneous + Intravenous Intraperitoneal Intravenous | 1 | 19.10 | −9.52 | 1 | 17.20 | −18.52 |
| 6 | ODSH + Gemcitabine | 24 mg/kg + 80 mg/kg | BID to end + Q3d x 4 (Day 1, 4, 7, 10) | Intravenous/Subcutaneous + Intravenous | 10 | 22.29 | 6.40 | 10 | 22.03 | 5.16 |
| 7 | Oxaliplatin + Gemcitabine | 10 mg/kg + 80 mg/kg | Day 1 + Q3d x 3 (Day 1, 4, 7) | Intravenous + Intravenous | 3 | 23.87 | 15.97 | 3 | 24.37 | 18.40 |
| 8 | ODSH + Oxaliplatin + Gemcitabine | 24 mg/kg + 10 mg/kg + 80 mg/kg | BID x 8 days + Day 1 + Q3d x 3 (Day 1, 4, 7) | Intravenous + Intravenous + Intraperitoneal | 0 | | | 0 | | |

^Beginning Day 26, groups 3 and 5 were taken off initial dosing regimen and the following dosing regimen was initiated:
Gr 3: Gemcitabine (80 mg/kg IP, Q3dx4 starting Day 26) + Nab-paclitaxel (15 mg/kg IV, 2xweekly starting Day 26)
Gr 5: ODSH (24 mg/kg, IV BID) + Gemcitabine (80 mg/kg IP, Q3dx4 starting Day 26) + Nab-paclitaxel (15 mg/kg IV, 2xweekly starting day 26)
*ODSH dosed intravenously Days 1-11; dosed subcutaneously Days 12-end Efficacy was assessed by comparison of tumor weights at Day 26 and 36 against Day 1. Day 26 was chosen to assess data prior to the addition of gemcitabine and nab-paclitaxel to groups 3 and 5. Day 36 was assessed as the last day of the study.

Tables 14 and 15, below, show the tumor weight and percent tumor growth inhibition (% TGI) for all treatment groups relative to Group 1 (the vehicle control group) at Day 26 and Day 36. See also FIG. 1 and FIG. 2.

TABLE 14

| Group | Treatment[1] | N | Dose | Schedule | Day 26 Tumor Weight (mg) | Day 26 % TGI (n) | Deaths[2] |
|---|---|---|---|---|---|---|---|
| 1 | Vehicle | 10 | — | BID to end | 679.8 ± 35.4 | — | 0 |
| 2 | ODSH | 10 | 24 mg/kg | BID to end | 616.2 ± 50.9 | 11.5 (10/10) | 0 |
| 3 | Oxaliplatin | 10 | 10 mg/kg | Wklyx4 | 635.0 ± 52.3 | 8.0 (10/10) | 0 |
| 4 | Gemcitabine | 10 | 80 mg/kg | Q3Dx4 | 594.7 ± 43.8 | 15.3 (10/10) | 0 |
| 5 | ODSH Oxaliplatin | 10 | 24 mg/kg 10 mg/kg | BID to end Wklyx4 | 586.6 ± 48.9 | 16.7 (10/10) | 0 |
| 6 | ODSH Gemcitabine | 10 | 24 mg/kg 80 mg/kg | BID to end Q3Dx4 | 508.9 ± 47.9 | 30.7 (10/10) | 0 |
| 7 | Oxaliplatin Gemcitabine | 10 | 10 mg/kg 80 mg/kg | Day 1 Q3Dx3 | 612.4 ± 94.3 | 15.5 (3/10) | 7 |
| 8 | ODSH Oxaliplatin Gemcitabine | 10 | 24 mg/kg 10 mg/kg 80 mg/kg | BID to end Day 1 Q3Dx3 | — | — | 10 |

[1]Treatment administered until Day 26
[2]Total deaths on or before Day 26

TABLE 15

| Group | Treatment[1] | n | Dose | Schedule | Day 36 Tumor Weight (mg) | Day 36 % TGI (n) | Deaths[2] |
|---|---|---|---|---|---|---|---|
| 1 | Vehicle | 10 | — | BID to end | 1524.2 ± 72.3 | — | 0 |
| 2 | ODSH | 10 | 24 mg/kg | BID to end | 1270.1 ± 95.5 | 18.2 (10/10) | 0 |

TABLE 15-continued

| Group | Treatment[1] | n | Dose | Schedule | Day 36 Tumor Weight (mg) | Day 36 % TGI (n) | Deaths[2] |
|---|---|---|---|---|---|---|---|
| 3 | Oxaliplatin | 10 | 10 mg/kg | 2xwklyx4 | — | — | 10 |
|   | Gemcitabine |   | 80 mg/kg | Day 26, 29, 32 |   |   |   |
|   | nab-paclitaxel |   | 15 mg/kg | Day 26, 29, 32 |   |   |   |
| 4 | Gemcitabine | 10 | 80 mg/kg | Q3Dx4 | 1288.8 ± 74.3 | 16.8 (10/10) | 0 |
| 5 | ODSH | 10 | 24 mg/kg | BID to end | 827.5 | 51.4 | 9 |
|   | Oxaliplatin |   | 10 mg/kg | 1xWklyx4 | (n = 1) | (1/10) |   |
|   | Gemcitabine |   | 80 mg/kg | Day 26, 29, 32, 35 |   |   |   |
|   | nab-paclitaxel |   | 15 mg/kg | Day 26, 29, 32 |   |   |   |
| 6 | ODSH | 10 | 24 mg/kg | BID to end | 993.9 ± 52.0 | 37.9 (10/10) | 0 |
|   | Gemcitabine |   | 80 mg/kg | Q3Dx4 |   |   |   |
| 7 | Oxaliplatin | 10 | 10 mg/kg | Day 1 | 1227.7 ± 244.7 | 22.5 (3/10) | 7 |
|   | Gemcitabine |   | 80 mg/kg | Day 1, 4, 7 |   |   |   |
| 8 | ODSH | 10 | 24 mg/kg | BID to end | — | — | 10 |
|   | Oxaliplatin |   | 10 mg/kg | Day 1 |   |   |   |
|   | Gemcitabine |   | 80 mg/kg | Day 1, 4, 7 |   |   |   |

[1]Treatment administered until Day 35
[2]Total deaths on or before Day 36

Mean tumor weight in the vehicle control group (Group 1) reached 679.8 mg by Day 26 and 1524.2 mg by Day 36. Six of ten tumors demonstrated some level of necrosis; however, this is attributed to the normal progression of this tumor xenograft model. Tumor necrosis was first observed on Day 30. A maximum weight loss of 3.6% was observed at Day 15. The mice recovered their weight by Day 26. Two of ten mice demonstrated slightly bruised tails, first observed on Day 11.

Mean tumor weight in the group receiving ODSH at 24 mg/kg (Group 2) reached 616.2 mg by Day 26 and 1270.1 mg by Day 36. This treatment resulted in a TGI of 11.5% on Day 26 and 18.2% on Day 36, relative to Day 1. No significant difference in tumor weight was observed on Day 26 when compared to vehicle control, however by Day 36 a significant difference in tumor weight was seen, in Group 2 relative to the vehicle control group. Three of ten tumors demonstrated some level of necrosis; however, this is attributed to the normal progression of this tumor xenograft model. Tumor necrosis was first observed on Day 30. A maximum weight loss of 2.7% was reached on Day 11. The mice recovered their weight by Day 22. All ten mice in this group demonstrated bruising on the tails or abdomen, at the site of injection. This was first observed on Day 8 for the tails and Day 15 for the abdomens. One of the ten mice also demonstrated swelling of the tail, first observed on Day 11.

Oxaliplatin 10 mg/kg or gemcitabine 80 mg/kg, and nab-paclitaxel 15 mg/kg (Group 3): The initial regimen of oxaliplatin alone reached a mean tumor weight of 635.0 mg by Day 26, prior to the addition of gemcitabine and nab-paclitaxel to the dosing regimen. This group produced a TGI of 8.0% on Day 26, when compared to vehicle control. No significant difference in tumor weight on Day 26 was observed when compared to vehicle control. One mouse exhibited a bruised tail, first observed on Day 11. Three of ten tumors demonstrated some level of necrosis; however, this is attributed to the normal progression of this tumor xenograft model. Tumor necrosis was first observed on Day 26.

Following data collection on Day 26, the combination treatment regimen of gemcitabine and nab-paclitaxel was initiated. This regimen proved to be toxic following the initial oxaliplatin alone treatment. No efficacy data could be reported for the triple combination.

Gemcitabine 80 mg/kg (Group 4) reached a mean tumor weight of 594.7 mg by Day 26 and 1288.8 mg by Day 36. This treatment resulted in a TGI of 15.3% on Day 26 and 16.8% on Day 36, when compared to vehicle control. No significant difference in tumor weight was observed on Day 26 or Day 36 when compared to vehicle control. Four of the ten tumors demonstrated some level of necrosis; however, this is attributed to the normal progression of this tumor xenograft model. Tumor necrosis was first observed on Day 26. A maximum weight loss of 8.7% was reached on Day 11. The mice recovered their weight by Day 18.

ODSH 24 mg/kg and oxaliplatin 10 mg/kg or ODSH 24 mg/kg, gemcitabine 80 mg/kg, and nab-paclitaxel 15 mg/kg (Group 5): The initial treatment combination of ODSH and oxaliplatin reached a mean tumor weight of 586.6 mg by Day 26. This treatment resulted in a TGI of 16.7% on Day 26 when compared to vehicle control. No significant difference in tumor weight was observed on Day 26 when compared to vehicle control, ODSH (Group 2), or oxaliplatin (Group 3). All ten mice in this group demonstrated increased bruising on the tails or abdomen, at the site of injection. This was first observed on Day 4 for the tails and Day 15 for the abdomens. Two of the ten mice also demonstrated swelling of the tail, first observed on Day 4. Three of the ten mice demonstrated some discoloration of the skin, first observed on Day 11.

The triple combination of ODSH, gemcitabine, and nab-paclitaxel, initiated on Day 26, resulted in increased toxicity following the initial treatment regimen of ODSH and oxaliplatin. No statistical analysis could be performed on Day 36 because only one mouse remained in this group to Day 36 with a tumor size of 827.5 mg (TGI=51.4%).

ODSH 24 mg/kg and gemcitabine 80 mg/kg (Group 6) reached a mean tumor weight of 508.9 mg by Day 26 and 993.9 mg by Day 36. This treatment resulted in a TGI of 30.7% on Day 26 and 37.9% on Day 36 when compared to vehicle control. No significant difference in tumor weight was observed on Day 26 when compared to vehicle control, ODSH (Group 2), or gemcitabine (Group 4). A significant decrease in tumor weight was seen on Day 36 (P<0.05) when compared to vehicle control; however, no significant difference in tumor weights resulted when compared to ODSH (Group 2) or gemcitabine (Group 4). One of ten tumors demonstrated some level of necrosis; however, this is attributed to the normal progression of this tumor xenograft model. Tumor necrosis was first observed on Day 30. A maximum weight loss of 13.4% was reached on Day 11. The mice recovered their weight by Day 22. All ten mice in this group demonstrated bruising on the tails or abdomen, at the site of injection. This was first observed on Day 4 for the tails and Day 15 for the abdomens. Two of the ten mice also demonstrated swelling of the tail, first observed on Day 4. One of ten mice demonstrated discoloration of the skin, first observed on Day 9. Two of ten mice demonstrated dry skin, first observed on Day 9.

Oxaliplatin 10 mg/kg and gemcitabine 80 mg/kg (Group 7) reached a mean tumor weight of 612.4 mg by Day 26 and 1227.7 mg by Day 36. This group produced a TGI of 15.5% on Day 26 (n=3) and 22.5% on Day 36 (n=3), when compared to the vehicle control. No significant difference in tumor weight was observed on Day 26, when compared to vehicle control, oxaliplatin (Group 3), or gemcitabine (Group 4). No significant difference in tumor weight was observed on Day 36 when compared to vehicle control or gemcitabine (Group 4). One of ten tumors demonstrated some level of necrosis; this is attributed to the natural progression of the xenograft model. Tumor necrosis was first observed on Day 30. A maximum weight loss of 16.6% was reached on Day 8. The mice recovered their weight by Day 15 following cessation of gemcitabine treatment. This treatment regimen proved to be toxic. Mice were found dead on Days 10, 11, and 14, and moribund sacrificed on Days 11 and 12. Two of ten mice in this group demonstrated bruising on the tails. This was first observed on Day 4.

ODSH 24 mg/kg, oxaliplatin 10 mg/kg, and gemcitabine 80 mg/kg (Group 8) could not be assessed for efficacy due to the toxicity of the regimen driven by the oxaliplatin and gemcitabine doses.

Treatment with ODSH alone was well-tolerated although some bruising and swelling at the site of injections occurred. Therefore, the dosing route was changed to subcutaneous injection at Day 12. The combination treatments of ODSH and gemcitabine and ODSH and oxaliplatin were tolerated. Conversely, treatment combination regimens that included gemcitabine with oxaliplatin or gemcitabine and nab-paclitaxel resulted in toxicity.

The combination of ODSH and gemcitabine resulted in the best efficacy at Day 26 and Day 36. On both comparison days, the combination of ODSH and gemcitabine resulted in notably lower tumor weights than gemcitabine alone. The tumor weights of mice treated with ODSH and gemcitabine were statistically significantly lower than tumor weights in the control (saline alone) group on Day 36. See FIG. 2.

The addition, on Day 26 of the study, of gemcitabine and nab-paclitaxel to the oxaliplatin regimen in Groups 3 and 5 demonstrated severe toxicity that led to the death of many animals. It is unclear whether these toxicities were due to the combined treatment with oxaliplatin, gemcitabine and nab-paclitaxel, or residual toxicity related to the administration of oxaliplatin.

6.2. Example 2: ODSH, a PF4-Interacting Heparinoid, Enhances the Efficacy of Carboplatin in an In Vivo Murine Xenograft Model of Human Ovarian Cancer This example demonstrates that adjunctive administration of ODSH enhances the efficacy of carboplatin against human ovarian tumors growing as xenografts in athymic nude mice.

Materials & Methods.

ODSH (50 mg/mL stock concentration) was made by Pyramid Laboratories, Inc. and stored at room temperature until use. As described further below, ODSH was administered either intravenously (IV), at a dose of 48 mg/kg and volume of 10 mL/kg, or subcutaneously (SC) at a dose of 24 mg/kg and volume of 5 mL/kg. Carboplatin obtained from a clinical supplier was stored at 4° C. until use. Carboplatin was administered by intraperitoneal injection (IP) at a dose of 80 mg/kg and volume of 10 mL/kg. Saline solution (0.9% NaCl) was used as a vehicle control for ODSH and administered by the same routes and in the same volumes as ODSH.

Human ovarian cancer cell line A2780 was used in the murine xenograft experiments as follows. Approximately $5 \times 10^6$ A2780 cells were used per mouse, injected subcutaneously into the right flank in 0.1 mL of 50% Matrigel/50% media. The study was initiated when tumors reached a size of 90-130 mg. 40 mice were used, 10 per treatment regimen. The mice were normal athymic female mice, aged 6-7 weeks, housed in microisolator cages and maintained under pathogen-free conditions. Tumor and body weights were measured three times per week.

ODSH, oxaliplatin, and the vehicle control (0.9% NaCl) were administered according to the dosing schedule described in the table below. Four treatment groups were studied.

TABLE A

Treatment regimens

| Treatment group | Treatment | Agent administered, and amount | Dosing schedule | Route* |
|---|---|---|---|---|
| 1 | Vehicle control | 0.9% saline | Days 1, 8, 15 | IV |
|  |  |  | Twice a day, until end of study on days without IV dosing | SC |
| 2 | ODSH | 48 mg/kg | Days 1, 8, 15 | IV |
|  |  | 24 mg/kg | Twice a day until end of study on days without IV dosing | SC |
| 3 | Carboplatin | 80 mg/kg | Days 1, 8, 15 | IP |
| 4 | ODSH | 48 mg/kg | Days 1, 8, 15 administered immediately after carboplatin | IV |
|  |  | 24 mg/kg | Twice a day until end of study on days without IV dosing | SC |
|  | Carboplatin | 80 mg/kg | Days 1, 8, 15 | IP |

*IV = intravenous, SC = subcutaneous, IP = intraperitoneal.

Results.

As shown in FIG. 4, ODSH does not reduce or counteract the anti-neoplastic effect of carboplatin. On the contrary, adjunctive administration of ODSH with carboplatin (FIG. 4, triangles) caused a significant reduction in the weights of tumors of human ovarian cancer cells, as compared to the reduction in tumor weights seen in mice receiving only carboplatin (FIG. 4, squares). Furthermore, mice treated with ODSH adjunctive to carboplatin had an increase in body weight as compared to mice receiving only carboplatin. See FIG. 6, triangles versus squares. Thus, ODSH not only increased the efficacy of carboplatin, it also contributed to improved body weights, indicative of a positive effect on constitutional side effects (e.g., loss of appetite, weight loss) often seen with chemotherapeutic treatment regimens.

Recorded tumor weights (in mg) for mice in experimental treatment groups 1 through 4 are provided in the tables below. Tumor weights were measured on days 1, 4, 6, 8, 11, 14, 18, 21, 25 and 28 as indicated.

| Group 1 | | | | | | | | | | |
|---|---|---|---|---|---|---|---|---|---|---|
| Vehicle Control 0 mg/kg | Dose Route: | Intravenous + Subcutaneous | | | | | | | | |
| | Frequency: | QD Day 1, 8, 15, 22 (IV) + BID Days 2-7, 9-14, 16-20, 23-27 (SC) | | | | | | | | |
| Day: | 1 | 4 | 6 | 8 | 11 | 14 | 18 | 21 | 25 | 28 |
| Mouse 1 | 90 | 157 | 270 | 438 | 637 | 816 | 1,166 | 1,513 | 2,045 | 2,566 |
| Mouse 2 | 97 | 161 | 250 | 368 | 627 | 1,103 | 1,728 | 2,722 | TS | TS |
| Mouse 3 | 101 | 131 | 164 | 340 | 435 | 790 | 1,199 | 1,437 | 2,251 | 3,542 |
| Mouse 4 | 104 | 184 | 295 | 435 | 591 | 975 | 1,486 | 2,231 | TS | TS |
| Mouse 5 | 104 | 148 | 285 | 403 | 710 | 1,053 | 1,797 | 2,313 | TS | TS |
| Mouse 6 | 108 | 145 | 259 | 465 | 764 | 1,157 | 1,487 | 2,053 | 2,547 | 3,425 |
| Mouse 7 | 108 | 202 | 397 | 629 | 1,047 | 1,330 | 2,138 | 3,480 | TS | TS |
| Mouse 8 | 112 | 167 | 303 | 391 | 725 | 1,080 | 1,563 | 2,051 | 2,940 | 4,020 |
| Mouse 9 | 122 | 181 | 350 | 508 | 741 | 1,171 | 1,825 | 2,600 | TS | TS |
| Mouse 10 | 126 | 171 | 277 | 396 | 663 | 1,009 | 1,595 | 1,991 | 2,388 | 3,246 |
| Mean | 107.3 | 164.6 | 285.0 | 437.3 | 694.0 | 1,048.5 | 1,598.3 | 2,239.1 | 2,434.1 | 3,359.7 |
| Median | 106.0 | 164.0 | 281.0 | 419.1 | 686.7 | 1,066.3 | 1,579.1 | 2,142.0 | 2,387.7 | 3,424.7 |
| Std Dev | 10.67 | 21.07 | 61.44 | 82.88 | 156.26 | 162.46 | 292.64 | 597.23 | 337.54 | 528.10 |
| Std Err | 3.37 | 6.66 | 19.43 | 26.21 | 49.41 | 51.37 | 92.54 | 188.86 | 150.95 | 236.17 |

| Group 2 | | | | | | | | | | |
|---|---|---|---|---|---|---|---|---|---|---|
| PGX ODSH 48 mg/kg | Dose Route: | Intravenous | | | | | | | | |
| | Frequency: | QD Day 1, 8, 15, 22 | | | | | | | | |
| PGX ODSH 24 mg/kg | Dose Route: | Subcutaneous | | | | | | | | |
| | Frequency: | BID Days 2-7, 9-14, 16-20, 23-27 | | | | | | | | |
| Day: | 1 | 4 | 6 | 8 | 11 | 14 | 18 | 21 | 25 | 28 |
| Mouse 1 | 90 | 121 | 241 | 373 | 635 | 1,084 | 1,615 | 2,642 | TS | TS |
| Mouse 2 | 96 | 117 | 171 | 315 | 491 | 815 | 1,157 | 1,681 | 2,423 | 3,129 |
| Mouse 3 | 101 | 138 | 201 | 296 | 529 | 762 | 1,422 | 2,025 | TS | TS |
| Mouse 4 | 104 | 159 | 309 | 449 | 816 | 1,303 | 1,796 | 2,692 | TS | TS |
| Mouse 5 | 104 | 111 | 215 | 321 | 366 | 670 | 1,150 | 1,467 | 2,414 | 3,909 |
| Mouse 6 | 107 | 195 | 347 | 639 | 910 | 1,499 | 1,836 | 2,639 | TS | TS |
| Mouse 7 | 109 | 131 | 264 | 413 | 653 | 1,032 | 1,568 | 1,852 | 2,464 | 3,784 |
| Mouse 8 | 112 | 173 | 235 | 411 | 536 | 868 | 1,714 | 1,880 | 2,599 | 3,252 |
| Mouse 9 | 120 | 124 | 139 | 183 | 349 | 559 | 891 | 1,289 | 1,817 | 2,671 |
| Mouse 10 | 126 | 200 | 282 | 422 | 811 | 1,253 | 1,869 | 2,560 | TS | TS |
| Mean | 107.0 | 146.8 | 240.3 | 382.2 | 609.6 | 984.4 | 1,501.7 | 2,072.6 | 2,343.5 | 3,349.0 |
| Median | 105.5 | 134.2 | 238.2 | 392.0 | 585.4 | 949.7 | 1,591.5 | 1,952.5 | 2,422.8 | 3,251.6 |
| Std Dev | 10.61 | 32.80 | 62.97 | 119.75 | 191.32 | 302.40 | 336.20 | 525.76 | 303.65 | 505.10 |
| Std Err | 3.36 | 10.37 | 19.91 | 37.87 | 60.50 | 95.63 | 106.32 | 166.26 | 135.80 | 225.89 |

| Group 3 | | | | | | | | | | |
|---|---|---|---|---|---|---|---|---|---|---|
| Carboplatin 80 mg/kg | Dose Route: | Intraperitoneal | | | | | | | | |
| | Frequency: | QD Day 1, 8, 15 | | | | | | | | |
| Day: | 1 | 4 | 6 | 8 | 11 | 14 | 18 | 21 | 25 | 28 |
| Mouse 1 | 94 | 137 | 200 | 419 | 517 | 587 | 942 | 1,218 | 1,921 | 2,461 |
| Mouse 2 | 96 | 108 | 157 | 245 | 442 | 706 | 730 | 941 | TS | TS |
| Mouse 3 | 102 | 109 | 169 | 262 | 402 | 640 | 671 | 1,040 | 1,246 | 1,739 |
| Mouse 4 | 104 | 108 | 114 | 148 | 103 | 96 | 84 | 112 | TS | TS |
| Mouse 5 | 105 | 175 | 264 | 466 | 539 | 875 | 1,349 | 1,790 | 2,403 | 2,877 |
| Mouse 6 | 106 | 199 | 239 | 358 | 499 | 799 | 1,218 | 1,596 | 2,127 | 2,599 |
| Mouse 7 | 110 | 142 | 223 | 371 | 419 | 628 | 713 | 834 | 1,109 | 1,539 |
| Mouse 8 | 113 | 163 | 300 | 605 | 813 | 1,093 | 1,806 | 2,675 | TS | TS |
| Mouse 9 | 116 | 147 | 208 | 306 | 555 | 795 | 1,160 | 1,626 | TS | TS |
| Mouse 10 | 127 | 194 | 256 | 386 | 542 | 975 | 1,168 | 1,439 | TS | TS |
| Mean | 107.3 | 148.2 | 213.0 | 356.5 | 483.1 | 719.3 | 984.1 | 1,327.3 | 1,761.3 | 2,243.0 |
| Median | 105.6 | 144.5 | 215.6 | 364.2 | 508.5 | 750.3 | 1,051.0 | 1,328.6 | 1,921.0 | 2,461.0 |
| Std Dev | 9.84 | 34.21 | 55.78 | 127.36 | 176.21 | 271.33 | 468.66 | 680.53 | 561.55 | 575.98 |
| Std Err | 3.11 | 10.82 | 17.64 | 40.27 | 55.72 | 85.80 | 148.20 | 215.20 | 251.13 | 257.59 |

| Group 4 | | | | | | | | | | |
|---|---|---|---|---|---|---|---|---|---|---|
| PGX ODSH 48 mg/kg | | | Dose Route: | | | Intravenous | | | | |
| | | | Frequency: | | | QD Day 1, 8, 15, 22 | | | | |
| PGX ODSH 24 mg/kg | | | Dose Route: | | | Subcutaneous | | | | |
| | | | Frequency: | | | BID Days 2-7, 9-14, 16-20, 23-27 | | | | |
| Carboplatin 80 mg/kg | | | Dose Route: | | | Intraperitoneal | | | | |
| | | | Frequency: | | | QD Day 1, 8, 15 | | | | |
| Day: | 1 | 4 | 6 | 8 | 11 | 14 | 18 | 21 | 25 | 28 |
| Mouse 1 | 94 | 108 | 155 | 210 | 240 | 319 | 444 | 555 | 740 | 1,053 |
| Mouse 2 | 95 | 140 | 173 | 231 | 342 | 414 | 614 | 724 | 1,307 | 1,795 |
| Mouse 3 | 103 | 107 | 132 | 141 | 146 | 153 | 246 | 406 | TS | TS |
| Mouse 4 | 103 | 153 | 179 | FD | FD | FD | FD | FD | FD | FD |
| Mouse 5 | 105 | 114 | 130 | 129 | 110 | 86 | 90 | 88 | TS | TS |
| Mouse 6 | 105 | 149 | 180 | 233 | 413 | 528 | 1,036 | 1,222 | TS | TS |
| Mouse 7 | 110 | 130 | 140 | 170 | 192 | 213 | 264 | 463 | TS | TS |
| Mouse 8 | 113 | 168 | 238 | 394 | 612 | 1,027 | 1,732 | 2,033 | TS | TS |
| Mouse 9 | 114 | 134 | 149 | 186 | 229 | 458 | 725 | 887 | 1,198 | 1,501 |
| Mouse 10 | 127 | 139 | 147 | 166 | 271 | 388 | 429 | 471 | 629 | 910 |
| Mean | 107.2 | 134.2 | 162.3 | 206.7 | 284.0 | 398.3 | 619.9 | 761.1 | 968.6 | 1,314.9 |
| Median | 105.2 | 136.4 | 151.9 | 185.7 | 240.4 | 388.3 | 444.3 | 554.7 | 968.8 | 1,277.2 |
| Std Dev | 9.73 | 19.97 | 32.39 | 79.09 | 154.07 | 276.98 | 504.37 | 574.83 | 334.13 | 407.49 |
| Std Err | 3.08 | 6.32 | 10.24 | 26.36 | 51.36 | 92.33 | 168.12 | 191.61 | 167.06 | 203.75 |

FD = Found Dead
TS = Terminal Sacrifice

Recorded individual body weights (in grams) for mice in experimental treatment groups 1 through 4 are provided in the tables below. Body weights were measured on days 1, 4, 6, 8, 11, 14, 18, 21, 25 and 28 as indicated.

| | | | | | | | 1st Weight | 2nd Weight Day 4 | | 3rd Weight Day 6 | | 4th Weight Day 8 | |
|---|---|---|---|---|---|---|---|---|---|---|---|---|---|
| Groups | Compound | Dosage | Route | Schedule | | Mouse | Day 1 Weight (g) | Weight (g) | Weight Change [%] | Weight (g) | Weight Change [%] | Weight | Weight Change [%] |
| Group 1 | Vehicle Control | 0 mg/kg | Intravenous | QD Days 1, 8, 15, 22 | | 1 | 20.5 | 21.3 | 3.9 | 20.9 | 2.0 | 21.5 | 4.9 |
| | | | Subcutaneous | BID Days 2-7, 9-14, 16-20, 23-27 | | 2 | 19.8 | 20.7 | 4.3 | 20.0 | 1.0 | 20.4 | 3.0 |
| | | | | | | 3 | 23.1 | 24.5 | 6.1 | 24.3 | 3.2 | 23.8 | 3.0 |
| | | | | | | 4 | 21.3 | 21.3 | 0.9 | 21.2 | −0.5 | 22.2 | 4.2 |
| | | | | | | 5 | 19.0 | 19.1 | 0.9 | 19.1 | 0.5 | 19.3 | 1.6 |
| | | | | | | 6 | 22.1 | 22.7 | 2.7 | 23.1 | 4.5 | 23.6 | 6.8 |
| | | | | | | 7 | 22.1 | 25.5 | 15.4 | 25.0 | 13.1 | 24.3 | 10.0 |
| | | | | | | 8 | 21.6 | 21.7 | 0.3 | 21.1 | −2.3 | 21.4 | −0.9 |
| | | | | | | 9 | 22.1 | 22.2 | 0.3 | 21.6 | −2.3 | 21.7 | −3.8 |
| | | | | | | 10 | 22.7 | 22.9 | 0.9 | 23.2 | 2.2 | 23.4 | 3.2 |
| Group 2 | PGX ODSH | 45 mg/kg | Intravenous | QD Days 1, 8, 15, 22 | | 1 | 22.1 | 22.9 | 3.6 | 23.2 | 5.0 | 23.2 | 5.0 |
| | PGX ODSH | 24 mg/kg | Subcutaneous | BID Days 2-7, 9-14, 16-20, 23-27 | | 2 | 20.3 | 20.6 | 1.5 | 20.6 | 1.5 | 21.4 | 3.4 |
| | | | | | | 3 | 21.0 | 20.9 | −0.5 | 21.2 | 1.0 | 21.6 | 2.8 |
| | | | | | | 4 | 21.8 | 21.4 | −1.5 | 21.5 | −1.4 | 22.3 | 2.3 |
| | | | | | | 5 | 21.6 | 23.0 | 6.5 | 24.5 | 13.4 | 25.1 | 16.2 |
| | | | | | | 6 | 21.4 | 21.8 | 1.9 | 22.0 | 2.8 | 22.6 | 5.6 |
| | | | | | | 7 | 19.8 | 19.6 | −1.0 | 20.1 | 2.0 | 20.9 | 5.6 |
| | | | | | | 8 | 19.9 | 20.9 | 5.6 | 21.3 | 7.6 | 22.2 | 12.1 |
| | | | | | | 9 | 20.9 | 23.0 | 10.0 | 22.6 | 8.1 | 22.3 | 6.7 |
| | | | | | | 10 | 19.7 | 19.2 | −2.5 | 19.2 | −2.5 | 20.1 | 2.0 |
| Group 3 | Carboplatin | 80 mg/kg | Intraperitoneal | QD Days 1, 8, 15 | | 1 | 20.3 | 19.1 | −3.9 | 19.4 | −4.4 | 20.1 | −1.0 |
| | | | | | | 2 | 21.6 | 21.1 | −2.3 | 20.5 | −3.7 | 21.3 | −1.4 |
| | | | | | | 3 | 22.2 | 21.8 | −1.5 | 21.5 | −3.2 | 22.3 | 0.5 |
| | | | | | | 4 | 23.2 | 22.6 | −2.6 | 22.5 | −3.0 | 23.7 | 2.2 |
| | | | | | | 5 | 20.6 | 19.5 | −3.3 | 19.6 | −4.9 | 20.7 | 0.5 |
| | | | | | | 6 | 22.6 | 21.6 | −4.4 | 22.9 | 1.3 | 24.0 | 6.2 |
| | | | | | | 7 | 21.7 | 21.0 | −3.1 | 21.4 | −1.4 | 22.0 | 1.4 |
| | | | | | | 8 | 20.7 | 21.1 | 1.9 | 21.5 | 3.9 | 21.8 | 5.3 |
| | | | | | | 9 | 22.4 | 22.3 | −0.4 | 22.3 | −0.4 | 22.9 | 2.2 |
| | | | | | | 10 | 19.7 | 18.6 | −5.6 | 19.1 | −3.0 | 20.0 | 1.9 |
| Group 4 | PGX ODSH | 45 mg/kg | Intravenous | QD Days 1, 8, 15, 22 | | 1 | 21.0 | 21.4 | 1.9 | 22.0 | 4.8 | 22.6 | 8.6 |
| | PGX ODSH | 24 mg/kg | Subcutaneous | BID Days 2-7, 9-14, 16-20, 23-27 | | 2 | 22.4 | 22.1 | −1.3 | 22.5 | 1.8 | 23.5 | 4.9 |

-continued

|  |  |  |  |  |  | 1st Weight | 2nd Weight Day 4 | | 3rd Weight Day 6 | | 4th Weight Day 8 | |
|---|---|---|---|---|---|---|---|---|---|---|---|---|
| Groups | Compound | Dosage | Route | Schedule | Mouse | Day 1 Weight (g) | Weight (g) | Weight Change [%] | Weight (g) | Weight Change [%] | Weight | Weight Change [%] |
|  | Carboplatin | 80 mg/kg | Intraperitoneal | QD Days 1, 8, 15 | 3 | 21.6 | 21.3 | −1.4 | 20.8 | −3.7 | 22.0 | 1.9 |
|  |  |  |  |  | 4 | 21.2 | 18.0 | −15.1 | 15.2 | −28.3 | FD | FD |
|  |  |  |  |  | 5 | 21.9 | 21.5 | −1.5 | 22.4 | 2.3 | 23.2 | 5.9 |
|  |  |  |  |  | 6 | 20.5 | 20.0 | −2.4 | 21.1 | 2.9 | 22.0 | 7.3 |
|  |  |  |  |  | 7 | 20.3 | 19.7 | −3.0 | 20.1 | −1.0 | 20.5 | 3.0 |
|  |  |  |  |  | 8 | 24.0 | 24.3 | 1.3 | 24.1 | 0.4 | 24.9 | 3.7 |
|  |  |  |  |  | 9 | 21.1 | 20.6 | −2.4 | 21.0 | −0.5 | 22.2 | 5.2 |
|  |  |  |  |  | 10 | 29.0 | 24.5 | −0.5 | 25.7 | 2.8 | 23.6 | 2.4 |

FD = Found Dead
TS = Terminal Sacrifice

|  |  |  |  |  |  | 5th Weight Day 11 | | 6th Weight Day 18 | | 7th Weight Day 18 | | 8th Weight Day 21 | |
|---|---|---|---|---|---|---|---|---|---|---|---|---|---|
| Groups | Compound | Dosage | Route | Schedule | Mouse | Weight | Weight Change [%] | Weight | Weight Change [%] | Weight | Weight Change [%] | Weight | Weight Change [%] |
| Group 1 | Vehicle Control | 0 mg/kg | Intra-venous Sub-cutaneous | QD Days 1, 8, 15, 22 BID Days 2-7, 9-14, 16-20, 23-27 | 1 | 21.4 | 4.4 | 22.4 | 9.3 | 22.6 | 10.2 | 21.0 | 12.2 |
|  |  |  |  |  | 2 | 21.3 | 7.5 | 21.9 | 10.6 | 22.6 | 14.1 | 23.3 | 17.7 |
|  |  |  |  |  | 3 | 24.4 | 5.6 | 24.4 | 5.6 | 24.3 | 7.8 | 24.9 | 7.8 |
|  |  |  |  |  | 4 | 22.3 | 4.7 | 22.5 | 7.0 | 23.0 | 8.0 | 22.9 | 7.9 |
|  |  |  |  |  | 5 | 19.7 | 3.7 | 20.9 | 10.0 | 21.6 | 13.7 | 21.6 | 14.7 |
|  |  |  |  |  | 6 | 23.6 | 6.5 | 23.9 | 6.1 | 21.3 | −3.6 | 23.1 | 4.5 |
|  |  |  |  |  | 7 | 23.8 | 7.7 | 25.1 | 23.6 | 24.7 | 11.8 | 24.2 | 9.5 |
|  |  |  |  |  | 8 | 21.3 | −1.4 | 22.1 | 2.3 | 22.2 | 2.5 | 22.6 | 4.5 |
|  |  |  |  |  | 9 | 21.5 | −1.4 | 22.7 | 2.7 | 22.3 | 0.9 | 23.1 | 4.5 |
|  |  |  |  |  | 10 | 23.4 | 3.1 | 23.5 | 4.8 | 24.3 | 7.0 | 23.8 | 4.8 |
| Group 2 | PGX ODSH PGX ODSH | 48 mg/kg 24 mg/kg | Intra-venous Sub-cutaneous | QD Days 1, 8, 15, 22 BID Days 2-7, 9-14, 16-20, 23-27 | 1 | 23.1 | 4.5 | 24.3 | 10.0 | 23.4 | 5.9 | 23.7 | 7.2 |
|  |  |  |  |  | 2 | 22.4 | 10.3 | 23.2 | 14.3 | 23.2 | 14.3 | 24.0 | 15.2 |
|  |  |  |  |  | 3 | 22.0 | 4.8 | 22.5 | 5.6 | 23.3 | 11.0 | 23.1 | 10.5 |
|  |  |  |  |  | 4 | 22.7 | 4.1 | 23.7 | 8.7 | 23.2 | 6.4 | 24.0 | 10.1 |
|  |  |  |  |  | 5 | 25.4 | 17.6 | 26.7 | 23.6 | 26.4 | 22.1 | 16.4 | 22.2 |
|  |  |  |  |  | 6 | 23.2 | 8.4 | 23.5 | 11.2 | 23.8 | 11.2 | 24.1 | 12.6 |
|  |  |  |  |  | 7 | 20.9 | 5.6 | 22.0 | 11.1 | 20.0 | 1.0 | 20.4 | 3.0 |
|  |  |  |  |  | 8 | 22.7 | 14.6 | 23.2 | 17.2 | 21.8 | 10.1 | 21.9 | 10.6 |
|  |  |  |  |  | 9 | 21.9 | 4.8 | 22.9 | 9.6 | 23.0 | 10.0 | 22.9 | 9.6 |
|  |  |  |  |  | 10 | 20.9 | 6.1 | 21.9 | 11.2 | 21.1 | 7.6 | 21.9 | 11.2 |
| Group 3 | Carboplatin | 80 mg/kg | Intra-peritoneal | QD Days 1, 8, 15, | 1 | 19.0 | −6.4 | 19.7 | −3.0 | 18.7 | −7.9 | 19.2 | −5.4 |
|  |  |  |  |  | 2 | 19.2 | −11.1 | 19.3 | −10.6 | 17.9 | −17.1 | 15.1 | −15.7 |
|  |  |  |  |  | 3 | 20.5 | −7.7 | 20.1 | −9.5 | 20.2 | −9.0 | 20.3 | −8.6 |
|  |  |  |  |  | 4 | 21.5 | −7.3 | 22.7 | −2.2 | 22.2 | −4.3 | 23.1 | −0.4 |
|  |  |  |  |  | 5 | 19.6 | −4.9 | 20.5 | 1.0 | 20.2 | −1.9 | 21.4 | 3.5 |
|  |  |  |  |  | 6 | 22.8 | 0.9 | 23.2 | 2.7 | 21.3 | −5.5 | 21.5 | −4.9 |
|  |  |  |  |  | 7 | 20.9 | −5.5 | 21.6 | −0.5 | 19.4 | −10.6 | 19.9 | −8.3 |
|  |  |  |  |  | 8 | 21.2 | 2.4 | 22.7 | 9.7 | 22.0 | 6.3 | 23.5 | 13.5 |
|  |  |  |  |  | 9 | 21.6 | −3.6 | 23.1 | 3.1 | 23.3 | 4.0 | 24.0 | 7.1 |
|  |  |  |  |  | 10 | 15.7 | −5.1 | 19.4 | −1.5 | 18.0 | −5.6 | 15.0 | −8.6 |
| Group 4 | PGX ODSH PGX ODSH | 48 mg/kg 24 mg/kg | Intra-venous Sub-cutaneous | QD Days 1, 8, 15, 22 BID Days 2-7, 9-14, 16-20, 23-27 | 1 | 21.7 | 3.3 | 22.1 | 3.2 | 21.2 | 1.0 | 20.7 | −1.4 |
|  |  |  |  |  | 2 | 21.9 | −2.2 | 23.2 | 3.6 | 22.5 | 0.4 | 22.5 | 0.4 |
|  | Carboplatin | 80 mg/kg | Intra-peritoneal | QD Days 1, 8, 15, | 3 | 20.0 | −7.4 | 20.9 | −5.1 | 19.4 | −10.2 | 19.8 | −8.3 |
|  |  |  |  |  | 4 | FD | FD | FD | FD | FD | FD | FD | FD |
|  |  |  |  |  | 5 | 22.9 | 4.6 | 23.9 | 9.1 | 22.1 | 0.9 | 23.1 | 5.5 |
|  |  |  |  |  | 6 | 20.7 | 1.0 | 21.4 | 4.4 | 19.3 | −5.9 | 19.1 | −6.8 |
|  |  |  |  |  | 7 | 18.3 | −9.9 | 16.5 | −17.2 | 17.7 | −12.5 | 18.1 | −10.2 |
|  |  |  |  |  | 8 | 22.1 | −7.9 | 21.0 | −12.5 | 19.5 | −173 | 20.7 | −13.8 |
|  |  |  |  |  | 9 | 21.7 | 2.8 | 23.3 | 10.4 | 21.9 | 3.5 | 22.6 | 7.1 |
|  |  |  |  |  | 10 | 24.2 | −3.2 | 25.5 | 2.0 | 23.3 | −6.8 | 23.8 | −4.8 |

FD = Found Dead
TS = Terminal Sacrifice

| Groups | Compound | Dosage | teiite | Schedule | Mouse | 9th Weight Day 25 Weight | 9th Weight Day 25 Weight change (%) | 10th Weight Day 28 Weight | 10th Weight Day 28 Weight change (%) |
|---|---|---|---|---|---|---|---|---|---|
| Group 1 | Vehicle Control | 0 mg/kg | Intravenous Subcutaneous | QD Days 1, 8, 15, 22 BID Days 2-7, 9-14, 16-20, 23-27 | 1 | 22.9 | 9.8 | 24.0 | 17.1 |
| | | | | | 2 | TS | TS | TS | TS |
| | | | | | 3 | 25.9 | 12.1 | 26.2 | 13.4 |
| | | | | | 4 | TS | TS | TS | TS |
| | | | | | 5 | TS | TS | TS | TS |
| | | | | | 6 | 24.1 | 9.0 | 24.0 | 8.6 |
| | | | | | 7 | TS | TS | TS | TS |
| | | | | | 8 | 23.9 | 10.6 | 20.7 | -4.2 |
| | | | | | 9 | TS | TS | TS | TS |
| | | | | | 10 | 23.3 | 2.6 | 24.2 | 6.6 |
| Group 2 | PGX ODSH PGX ODSH | 48 mg/kg 24 mg/kg | Intravenous Subcutaneous | QD Days 1, 8, 15, 22 BID Days 2-7, 9-14, 16-20, 23-27 | 1 | TS | TS | TS | TS |
| | | | | | 2 | 24.3 | 19.7 | 25.0 | 23.2 |
| | | | | | 3 | TS | TS | TS | TS |
| | | | | | 4 | TS | TS | TS | TS |
| | | | | | 5 | 28.3 | 31.0 | 28.7 | 32.9 |
| | | | | | 6 | TS | TS | TS | TS |
| | | | | | 7 | 23.7 | 9.6 | 22.5 | 15.7 |
| | | | | | 8 | 23.4 | 18.2 | 23.8 | 20.2 |
| | | | | | 9 | 24.0 | 14.5 | 24.2 | 15.8 |
| | | | | | 10 | TS | TS | TS | TS |
| Group 3 | Carboplatin | 80 mg/kg | Intraperitoneal | QD Days 1, 8, 15 | 1 | 19.9 | -2.0 | 20.9 | 3.0 |
| | | | | | 2 | TS | TS | TS | TS |
| | | | | | 3 | 20.4 | -8.1 | 20.3 | -8.6 |
| | | | | | 4 | TS | TS | TS | TS |
| | | | | | 5 | 22.3 | 8.3 | 23.0 | 11.7 |
| | | | | | 6 | 21.8 | -3.5 | 22.2 | -1.8 |
| | | | | | 7 | 20.2 | -6.9 | 21.1 | -2.8 |
| | | | | | 8 | TS | TS | TS | TS |
| | | | | | 9 | TS | TS | TS | TS |
| | | | | | 10 | TS | TS | TS | TS |
| Group 4 | PGX ODSH PGX ODSH Carboplatin | 48 mg/kg 24 mg/kg 80 mg/kg | Intravenous Subcutaneous Intraperitoneal | QD Days 1, 8, 15, 22 BID Days 2-7, 9-14, 16-20, 23-27 QD Days 1, 8, 15, | 1 | 22.5 | 9.0 | 22.9 | 9.0 |
| | | | | | 2 | 23.6 | 5.4 | 23.5 | 6.3 |
| | | | | | 3 | TS | TS | TS | TS |
| | | | | | 4 | FD | FD | FD | FD |
| | | | | | 5 | TS | TS | TS | TS |
| | | | | | 6 | TS | TS | TS | TS |
| | | | | | 7 | TS | TS | TS | TS |
| | | | | | 8 | TS | TS | TS | TS |
| | | | | | 9 | 23.3 | 10.4 | 23.9 | 13.3 |
| | | | | | 10 | 25.3 | 2.0 | 26.3 | 5.2 |

FD = Found Dead
TS = Terminal Sacrifice

6.3. Example 3: ODSH, a PF4-Interacting Heparinoid, Attenuates Thrombocytopenia and Neutropenia, Induces Thrombopoiesis and Neutrophil Production, and Reduces Constitutional Symptoms in Patients Receiving a Chemotherapy Treatment Regimen Having Myelosuppressive Side Effects Patients diagnosed with metastatic pancreatic cancer were treated with ODSH as an adjunct to treatment with gemcitabine and nab-paclitaxel (Abraxane®, albumin-bound paclitaxel) in an unblinded clinical trial.

Inclusion Criteria.

Male and non-pregnant, non-lactating, female patients, aged 18 to 75, with histologically confirmed metastatic adenocarcinoma of the pancreas were enrolled in the trial. Further inclusion criteria were: presence of at least one metastatic tumors (measurable by conventional techniques or CT scan), serum CA 19-9 measurement of greater than 2 times the upper limit of normal, no radiation therapy or chemotherapy for locally advanced disease within six months of enrollment into the trial, absolute neutrophil count of at least $1.5 \times 10^9$/L, platelet count of at least 100,000/mm$^3$ (or 100× 10$^9$/L), hemoglobin level of at least 9 g/dL, prothrombin and partial thromboplastin times within normal limits (+/−15%) at time of screening, Eastern Cooperative Oncology Group performance status of 1 or more. In addition, patients were screened for blood chemistry levels, including serum creatinine levels within normal limits, serum transaminase levels of 2.5 or greater than the upper limit of normal, and bilirubin levels of 1.5 times the upper limit of normal or more.

Dosing Regimen.

Treatment consisted of a series of 28-day cycles, wherein the last day of one cycle (e.g., day 28, cycle 1) was immediately followed by the first day of the next cycle (e.g., day 1, cycle 2). In each 28-day treatment cycle, patients were dosed at days 1, 8, and 15 (three weeks of medication followed by one week of rest) as follows. First, nab-paclitaxel at 125 mg/m$^2$ was administered as an intravenous infusion over 30 minutes. Next, gemcitabine was administered at 1000 mg/m$^2$ as an intravenous infusion over 30 minutes. Nab-paclitaxel and gemcitabine therapy was given as described in the prescribing information for Abraxane® and Gemzar®. See also, Von Hoff et al., 2011, J. Clinical Oncology 29:1-7).

ODSH was administered immediately after gemcitabine administration, as follows: an initial loading dose was administered as a bolus of 4 mg/kg over 5 minutes followed by a continuous intravenous infusion over 48 hours, at a dose of 0.375 mg/kg/hr. These doses are, respectively, 9-fold higher and 3.75-fold higher than the bolus and maintenance doses of unfractionated heparin routinely used to confer full anticoagulation in a clinical setting (0.44 mg/kg for bolus injection, and 0.1 mg/kg/hr for maintenance). As a substantially non-anticoagulant heparinoid, ODSH can be administered at a dose that is greater than the fully anticoagulant dose of unfractionated heparin, without concern for anticoagulant effect, as shown in the Results below.

An initial run-in period was conducted in which ten patients were treated with the gemcitabine, nab-paclitaxel, and ODSH regimen described above. After all ten patients had completed at least one 28-day cycle, the data were reviewed and an open-label randomized study initiated, with two arms (ODSH arm and Control arm). In the ODSH arm, the dosing regimen was the same as in the run-in period (gemcitabine, nab-paclitaxel, and ODSH). In the Control arm, patients were given the same gemcitabine and nab-paclitaxel regimen as in the run-in period, but without ODSH.

Testing.

Blood was drawn before treatment administration on days 1, 8, and 15 of each 28 day cycle. Platelet counts, total white blood cell counts, and absolute neutrophil counts were performed. Grading of thrombocytopenia and/or neutropenia was performed according to the following standards:

|  | Grade | Platelet count ($\times 10^3$/µl blood) |
|---|---|---|
| Thrombocytopenia | 0* | >150 |
|  | 1 | <150-75 |
|  | 2 | <75-50 |
|  | 3 | <50-25 |
|  | 4 | <25 |
| *(non-thrombocytopenic) | | |
| Neutropenia | 0* | ≥2 |
|  | 1 | <2-1.5 |
|  | 2 | <1.5-1 |
|  | 3 | <1.0-0.5 |
|  | 4 | <0.5 |

*(non-neutropenic)

Blood samples were also tested on day 1 of each treatment cycle for the serum level of CA19-9 (carbohydrate antigen 19-9) a marker used to assess the efficacy of the chemotherapy agents in treating pancreatic cancer. See, e.g., Maeda, 2011, *Int. J. Clin. Oncol.* 16(5):539-45. Reduction in the serum level of CA19-9 is indicative of chemotherapeutic efficacy against the pancreatic cancer. Tumor response and disease status was measured according to Response Evaluation Criteria in Solid Tumors (RECIST) Guidelines Version 1.1. *Eur. J. Cancer,* 2009, 45:228-247. A reduction of at least 30% in the sum of the diameters of target lesions (measurable lesions present at screening, up to 2 lesions per involved organ) was scored as a partial response. Patients were scored as having stable disease where the smallest sum of target lesion diameters neither decreased nor increased sufficiently to qualify as a partial response or progressive disease.

Lack of anticoagulation by ODSH was confirmed by monitoring partial thromboplastin time (aPTT) during ODSH infusion, at days 1, 3, 10, and 17 of treatment cycle 1. Normal range of aPTT is about 27 to 35 seconds+/−15%.

Patients were also assessed for other side effects of chemotherapy, including fatigue, sensory neuropathy, nausea, and vomiting, each of which was graded according to severity. Grades were: 0 (normal), 1 (mild), 2 (moderate), 3 (severe) and 4 (life-threatening).

Results.

Platelet counts are shown in Table 16 below. Counts shown in the "Screen" column are counts prior to entry into the clinical trial protocol.

Ten out of 10 patients who completed the first cycle of chemotherapy and who also had blood drawn at the beginning of the second cycle had platelet counts at the beginning of the second cycle that were greater than their platelet counts at the beginning of the first cycle, before any chemotherapy had been administered. Eight out of 9 patients who completed the second cycle of chemotherapy and who also had blood drawn at the beginning of the third cycle had platelet counts at the beginning of the third cycle that were greater than their platelet counts at the beginning of the first cycle, before any chemotherapy had been administered. This trend was robust, continuing into subsequent cycles of chemotherapy. For example, 9 out of 10 patients who completed the third cycle of chemotherapy and who also had blood drawn at the beginning of the fourth cycle had platelet counts at the beginning of the fourth cycle that were greater than their platelet counts at the beginning of the first cycle, before any chemotherapy had been administered.

TABLE 16

Platelet Count ($\times 10^3$/µl blood)

| Patient ID | Screen | Cycle 1 | | | Cycle 2 | | | Cycle 3 | | | Cycle 4 | | | Cycle 5 | | | Cycle 6 | | |
|---|---|---|---|---|---|---|---|---|---|---|---|---|---|---|---|---|---|---|---|
|  |  | Day 1 | Day 8 | Day 15 | Day 1 | Day 8 | Day 15 | Day 1 | Day 8 | Day 15 | Day 1 | Day 8 | Day 15 | Day 1 | Day 8 | Day 15 | Day 1 | Day 8 | Day 15 |
| 2001 | 204 | 342 | 206 | 134 | 614 | 375 | 186 | 628 | 371 | 171 | 626 | 507 | 169 | 607 | 377 |  |  |  |  |
| 6002 | 505 | 429 | 214 | 260 | 532 | 257 | 170 | 387 | 362 | 189 | 382 | 448 | 202 | 427 | 403 | 194 | 503 | 493 | 164 |
| 6003 | No data | 180 | 86 | 63 | 274 | 95 | 54 | 361 | 179 | 71 | 387 | 185 | 78 | 288 | 188 | 72 | 275 | 148 | 72 |
| 6004 | 321 | 313 | 205 | 135 | 419 | 434 | 209 | 510 | 435 | 207 | 586 | 464 | 203 | 499 | 231 | 132 | 288 | 384 | 169 |
| 6006 | No data | 264 | 167 | 178 | 322 | 336 | 207 | 327 | 325 | 170 | 402 | 339 | 170 | 351 | 288 | 169 | 370 | 321 | 162 |
| 6007 | 187 | 191 | 108 | 108 | 312 | 241 | 132 | 362 | 362 | 163 | 292 | 355 | 140 | 266 | 241 | 153 | 294 | 207 | 128 |
| 7001 | 269 | 274 | 150 | 75 | 574 | 424 | 167 | 655 | 388 | 188 | 478 | 468 | 163 | 389 | 325 | 109 | 489 | 336 | 102 |
| 7002 | 267 | 276 | 239 | 220 | 445 | 357 | 186 | 418 | 223 | 171 | 667 | 193 | 149 | 275 | 192 |  |  |  |  |
| 8001 | 166 | 120 | 86 | 76 | 175 | 83 | 70 | 123 | 119 | 63 | 184 |  | 129 | 106 | 94 | 58 | 114 | 85 | 54 |
| 9001 | 271 | 271 | 230 | 181 | 417 | 402 | 178 | 487 | 355 | 172 | 406 | 188 | 339 | 512 | 378 | 193 | 371 | 313 | 338 |

FIG. 8 shows a plot of the platelet counts for individual patients as measured in samples taken before treatment on indicated days (D1=day 1, D8=day 8, and D15=day 15) of the indicated cycles (C1=cycle 1; C2=cycle 2, etc.). There is a clear trend of increasing platelet count at the start of each successive cycle of treatment, relative not only to the platelet count after two weeks of treatment in a previous cycle, but also relative to the platelet count at the start of the initial cycle of treatment, i.e. before any treatment was administered. None of the patients exhibited thrombocytopenia at the start of the second cycle and only one of 8 patients exhibited thrombocytopenia at the start of the third cycle.

Table 17 shows the percentage of patients with thrombocytopenia after two doses (day 15, first cycle) or after five or more doses (day 15, second cycle or day 1, third cycle) of treatment with ODSH adjunctive to gemcitabine and nab-paclitaxel. Also shown in Table 17, at row 3, are historical data, showing the percentages of patients with varying grades of thrombocytopenia who had been treated with gemcitabine and nab-paclitaxel in the same amounts and on the same dosing schedule as described herein, but without adjunctive administration of ODSH. The data presented in row 3 are reproduced from Table 3 of Von Hoff et al., 2011, *J Clinical Oncology* 29:1-7, which provides the overall number and percent of patients exhibiting selected adverse events throughout the trial. Total number of patients in each category is shown in parentheses.

TABLE 17

| | Toxicity (% patients with thrombocytopenia of indicated grade) | | | | |
|---|---|---|---|---|---|
| Row | Treatment (no. of patients) | Grade 0 | Grade 1 | Grade 2 | Grade 3 | Grade 4 |
| 1 | Gemcitabine + nab-paclitaxel + ODSH, first cycle, day 15 (10) | 40 | 50 | 10 | 0 | 0 |
| 2 | Gemcitabine + nab-paclitaxel + ODSH, second cycle day 15 (10) | 70 | 10 | 20 | 0 | 0 |
| 3 | Von Hoff et al. Gemcitabine + nab-paclitaxel (44) (historical) | 9 | 42 | 21 | 19 | 9 |

As shown above, after two doses of treatment, 40% of the patients treated adjunctively with ODSH showed no thrombocytopenia, and 90% of the patients had no more than mild thrombocytopenia. After five doses of treatment (day 15 of cycle 2), 7 out of 10 patients had no thrombocytopenia.

Table 18 shows the platelet counts for each patient at day 1 of successive treatment cycles (e.g., treatment cycle 1, 2, 3, etc.). As can be seen from the platelet counts at the beginning of cycles 2 and 3, even after receiving one or two full cycles (equal to three or six doses) of gemcitabine and nab-paclitaxel, only one of the patients was thrombocytopenic, exhibiting mild (Grade 1) thrombocytopenia. All other patients showed platelet counts well above the lower limit of normal. This trend continued into Cycle 4 for patients 2001, 6002, 6003, 6004, 6006, 6007, 7001, 8001, and 9001. Overall, platelets counts in 10/10 patients were higher at the beginning of cycle 2 than at the beginning of cycle 1, and platelets counts in 6/9 patients were higher at the beginning of cycle 3 than at the beginning of cycle 2.

TABLE 18

| | Platelet count at start of cycle | | | | | | |
|---|---|---|---|---|---|---|---|
| Patient number | Cycle 1 | Cycle 2 | Cycle 3 | Cycle 4 | Cycle 5 | Cycle 6 | Cycle 7 |
| 2001 | 342 | 614 | 628 | 626 | | | |
| 6002 | 429 | 532 | 387 | 382 | 427 | 503 | |
| 6003 | 180 | 274 | 361 | 387 | 288 | 275 | |
| 6004 | 313 | 419 | 510 | 586 | 499 | 288 | |
| 6006 | 264 | 322 | 327 | 402 | 351 | | |
| 6007 | 191 | 312 | 362 | 292 | | | |
| 7001 | 274 | 574 | 655 | 478 | 389 | 489 | 454 |
| 7002 | 276 | 445 | 418 | 667 | 275 | | |
| 8001 | 120 | 175 | 123 | 184 | | | |
| 9001 | 271 | 417 | | 406 | 512 | 371 | |

As shown further in FIG. 10A, mean and median platelet counts across all samples were consistently above 150,000 on the first day of treatment cycles 2 and 3, even when numbers were below 150,000 on day 15 of the first treatment cycle. In fact, in treatment cycles 2 and 3, mean and median platelet counts at day 15—when platelet counts are expected to be at their lowest—remained in the normal range. Furthermore, mean and median platelet counts at the start of the third cycle were greater than at the start of the second cycle and were greater at the start of the second cycle than at the screening measurement and the start of the first cycle (before any chemotherapy was administered).

In the randomized stage of the trial, a statistically significant difference in platelet counts was detected between the ODSH arm and the Control arm of the study, as shown in Table 19 below, demonstrating that ODSH attenuates thrombocytopenia associated with myelosuppressive treatment regimens.

TABLE 19

| Patient number | Cycle 1 Day 15 | Cycle 2 Day 15 | Cycle 3 Day 15 | Cycle 4 Day 15 |
|---|---|---|---|---|
| | ODSH ARM | | | |
| 6009 | 199 | 92 | 96 | 138 |
| 8002 | 172 | 165 | | |
| 8005 | 162 | | | |
| 9002 | 232 | | | |
| 9004 | 231 | 110 | 124 | |
| 11001 | 216 | 156 | | |
| 14001 | 121 | 95 | 74 | 31 |
| 14002 | 103 | 74 | 76 | |
| | CONTROL ARM | | | |
| 4002 | 64 | | | |
| 6008 | 92 | 81 | 38 | |
| 8003 | 186 | 200 | | |
| 9003 | 71 | 119 | 53 | 78 |
| 11002 | 77 | | | |
| 14003 | 95 | 80 | 94 | |
| 14005 | 104 | 118 | 117 | |
| | One tail t-test | | Two tail t-test | |
| Effect on platelets | .021 | | .042 | |

Table 20 below provides absolute neutrophil counts for the patients treated adjunctively with ODSH. Eight out of 10 patients who completed the first cycle of treatment showed normal neutrophil counts on the first day of the second treatment cycle. Five out of 10 patients who completed the first cycle also had increased or unchanged neutrophil counts on the first day of the second treatment cycle as compared to the first day of the first cycle (prior to chemotherapy). Furthermore, 8 out of 9 patients showed normal neutrophil counts at the start of the third cycle of treatment and 10 out of 10 patients showed normal neutrophil counts at the start of the fourth cycle of treatment.

than mild neutropenia. After five doses of treatment (day 15 of cycle 2) or eight doses of treatment (day 15 of cycle 3) 7 out of 10 patients had no more than mild neutropenia. As shown further in FIG. 10B, mean and median absolute neutrophil

TABLE 20

Neutrophil Values (×10³/μl blood)

| Patient ID | Screen | Cycle 1 | | | Cycle 2 | | | Cycle 3 | | | Cycle 4 | | | Cycle 5 | | | Cycle 6 | | |
|---|---|---|---|---|---|---|---|---|---|---|---|---|---|---|---|---|---|---|---|
| | | Day 1 | Day 8 | Day 15 | Day 1 | Day 8 | Day 15 | Day 1 | Day 8 | Day 15 | Day 1 | Day 8 | Day 15 | Day 1 | Day 8 | Day 15 | Day 1 | Day 8 | Day 15 |
| 2001 | 9.3 | 4.0 | 1.0 | 1.3 | 3.4 | 2.3 | 2.7 | 3.1 | 1.8 | 2.6 | 3.8 | | | | | | | | |
| 6002 | 7.6 | 6.2 | 4.0 | 3.9 | 8.3 | 1.7 | 2.4 | 3.4 | 1.5 | 1.5 | 4.4 | 2.6 | 2.9 | 5.0 | 2.1 | 2.3 | 5.2 | 3.7 | 1.2 |
| 6003 | No data | 4.5 | 2.2 | 0.9 | 1.9 | 1.8 | 1.5 | 3.2 | 1.5 | | 2.7 | 1.5 | 1.1 | 2.0 | 0.9 | 1.0 | 2.2 | 0.9 | 1.1 |
| 6004 | 5.6 | 4.3 | 1.3 | 0.7 | 7.3 | 3.8 | 1.8 | 2.7 | 1.6 | 1.5 | 2.2 | 2.5 | 4.6 | 1.6 | 2.1 | 0.8 | 13.5 | 1.3 | 1.7 |
| 6006 | No data | 3.6 | 2.1 | 1.6 | 1.6 | 2.6 | 1.7 | 2.8 | 4.2 | 1.8 | 5.2 | 2.7 | 2.4 | 3.2 | 3.4 | 3.9 | | | |
| 6007 | 5.9 | 5.5 | 4.3 | 3.6 | 4.6 | 3.7 | 3.8 | 2.2 | 6.8 | 4.5 | 5.7 | | | | | | | | |
| 7001 | 4.0 | 3.6 | 0.5 | 0.7 | 13.0 | 6.3 | 0.7 | 3.9 | 3.9 | 1.4 | 5.9 | 2.2 | 3.4 | 3.3 | 1.6 | 1.1 | 2.3 | 1.2 | 10.7 |
| 7002 | 4.0 | 2.1 | 3.0 | 3.5 | 2.1 | 3.7 | 1.5 | 1.8 | 1.4 | 1.5 | 3.5 | 2.0 | 0.7 | 23.2 | 4.1 | | | | |
| 8001 | 5.3 | 3.3 | 1.5 | 1.0 | 6.0 | 1.3 | 1.1 | 3.2 | 1.4 | 0.8 | 3.2 | | | | | | | | |
| 9001 | 4.3 | 4.3 | | | 3.6 | 1.9 | 1.0 | | | | 2.7 | 1.4 | 1.7 | | | | | | |

FIG. 9 shows a plot of the neutrophil count for individual patients as measured in samples taken before treatment on indicated days (D1=day 1, D8=day 8, and D15=day 15) of the indicated cycles (C1=cycle 1; C2=cycle 2, etc.). There is a clear trend of increasing neutrophil count at the start of the second cycle of treatment, relative to the neutrophil count at the start of the initial cycle of treatment, i.e. before any treatment was administered.

Table 21 shows the percentage of patients with neutropenia after two doses (day 15, first cycle) or after five or more doses (day 15, second cycle or day 15, third cycle) of treatment with ODSH adjunctive to gemcitabine and nab-paclitaxel. Also shown in Table 21, at row 3, are historical data showing the percentages of patients with varying grades of neutropenia who had been treated with gemcitabine and nab-paclitaxel in the same amounts and on the same dosing schedule as described herein, without ODSH. The data presented in row 3 are reproduced from Table 3 of Von Hoff et al., 2011, *J. Clinical Oncology* 29:1-7, which provides the overall number and percent of patients exhibiting selected adverse events throughout the trial. The total number of patients in each category is shown in parentheses.

TABLE 21

Toxicity (% patients with neutropenia of indicated grade)

| Row | Treatment (no. of patients) | Grade 0 | Grade 1 | Grade 2 | Grade 3 | Grade 4 |
|---|---|---|---|---|---|---|
| 1 | Gemcitabine + nab-paclitaxel + ODSH, first cycle day 15 (9) | 33 | 11 | 22 | 33 | 0 |
| 2 | Gemcitabine + nab-paclitaxel + ODSH, second cycle day 15 or third cycle day 15 (10) | 20 | 50 | 20 | 10 | 0 |
| 3 | Von Hoff et al. Gemcitabine + nab-paclitaxel (44) | 9 | 14 | 2 | 26 | 49 |

As shown above, after two doses of treatment, 44% of the patients treated adjunctively with ODSH showed no more counts across all samples, were consistently above 2,000 on the first day of treatment cycles 2 and 3, even when numbers were below 2,000 on day 15 of the previous cycle. With successive cycles and without dose reduction, patients with grade 3 neutropenia at the nadir of the first cycle, had no more than grade 1 or 2 neutropenia in cycles 2 or 3 (see patients 6004, 6004, and 7001). Only one patient (7001) out of 10 was treated with G-CSF, receiving a single dose in cycle 1.

In the randomized stage of the trial, a statistically significant difference in neutrophil counts was detected between the ODSH arm and the Control arm of the study, as shown in Table 22 below, demonstrating that ODSH attenuates neutropenia associated with myelosuppressive treatment regimens.

TABLE 22

| Patient number | Cycle 1 Day 15 | Cycle 2 Day 15 | Cycle 3 Day 15 | Cycle 4 Day 15 |
|---|---|---|---|---|
| ODSH Arm | | | | |
| 6009 | 4.7 | 3.7 | 5.4 | 4.1 |
| 8002 | 3.0 | 3.7 | | |
| 8005 | 0.3 | | | |
| 9002 | 4.0 | | | |
| 9004 | 2.4 | 1.8 | 1.0 | |
| 11001 | 1.4 | 1.8 | | |
| 14001 | 4.0 | 1.6 | 1.6 | 4.8 |
| 14002 | 0.8 | 0.8 | 0.8 | |
| Control Arm | | | | |
| 4002 | 0.6 | | | |
| 6008 | 1.1 | 1.1 | 0.3 | |
| 8003 | 1.7 | 1.7 | | |
| 9003 | 0.8 | 0.8 | 1.0 | 0.9 |
| 11002 | 1.4 | | | |
| 14003 | 3.3 | 2.2 | 3.1 | |
| 14005 | 2.3 | 1.8 | 1.3 | |
| | One tail t-test | | Two tail t-test | |
| Effect on neutrophils | .009 | | .017 | |

Total white blood cell counts were consistent with neutrophil counts, as shown below in Table 23.

TABLE 23

White Blood Cell Counts (×10³/μl blood)

| Patient ID | Screen | Cycle 1 Day 1 | Cycle 1 Day 8 | Cycle 1 Day 15 | Cycle 2 Day 1 | Cycle 2 Day 8 | Cycle 2 Day 15 | Cycle 3 Day 1 | Cycle 3 Day 8 | Cycle 3 Day 15 | Cycle 4 Day 1 | Cycle 4 Day 8 | Cycle 4 Day 15 |
|---|---|---|---|---|---|---|---|---|---|---|---|---|---|
| 2001 | 10.8 | 5.7 | 2.3 | 2.7 | 5.7 | 4.5 | 4.3 | 6.0 | | | | | |
| 6002 | 10.6 | 8.7 | 5.7 | 5.4 | 11.0 | 4.6 | 5.4 | 7.6 | 4.8 | 4.3 | 8.5 | 6.0 | |
| 6003 | 6.0 | 6.0 | 3.4 | 1.5 | 3.4 | 2.9 | 2.4 | 4.8 | 2.7 | | | | |
| 6004 | 7.3 | 7.2 | 4.1 | 2.7 | 10.8 | 6.4 | 4.4 | 5.8 | | | | | |
| 6006 | No data | 6.8 | 4.4 | 4.2 | 4.9 | | | | | | | | |
| 6007 | 8.5 | 7.7 | 6.2 | 5.1 | 7.8 | | | | | | | | |
| 7001 | 6.7 | 7.3 | 2.7 | 2.1 | 17.8 | 10.2 | 3.4 | | | | | | |
| 7002 | 6.3 | 5.0 | 5.3 | 6.0 | 5.9 | | | | | | | | |
| 8001 | 6.7 | 4.6 | 2.8 | 2.0 | | | | | | | | | |
| 9001 | 6.5 | 6.5 | 5.1 | 3.2 | 6.5 | | | | | | | | |

Assessment of fatigue, sensory neuropathy, nausea, and vomiting, all of which are common side effects of chemotherapy, and notably in the gemcitabine-abraxane regimen described in Von Hoff et al., revealed that patients treated adjunctively with ODSH experienced mild to moderate symptoms, with more than 50% of the patients experiencing no more than Grade 1 side effects. Table 24 below provides the percentage of patients experiencing different grades of each side effect, as compared to the percentages reported in Von Hoff et al., 2011, *J. Clinical Oncology* 29:1-7.

TABLE 24

| Side Effect | Treatment (no. of patients) | Toxicity (% patients per indicated grade) | | | |
|---|---|---|---|---|---|
| | | Grade 0 | Grade 1 | Grade 2 | Grade 3 |
| Fatigue | Von Hoff et al. (44) | 20 | 23 | 30 | 27 |
| | Gemcitabine + nab-paclitaxel + ODSH (9) | 45 | 55 | 0 | 0 |
| Nausea | Von Hoff et al. (44) | 53 | 25 | 20 | 2 |
| | Gemcitabine + nab-paclitaxel + ODSH (9) | 45 | 55 | 0 | 0 |
| Vomiting | Von Hoff et al. (44) | 63 | 23 | 7 | 7 |
| | Gemcitabine + nab-paclitaxel + ODSH (9) | 91 | 9 | 0 | 0 |
| Sensory Neuropathy | Von Hoff et al. (44) | 26 | 34 | 20 | 20 |
| | Gemcitabine + nab-paclitaxel + ODSH (9) | 90 | 0 | 0 | 10 |

Serum CA19-9 level, a marker correlated with extent of tumor, and therefore correlated with efficacy of the chemotherapeutic treatment, decreased in 8 of 10 patients, showing that the ability of ODSH to attenuate thrombocytopenia and neutropenia and induce thrombopoiesis and neutrophil production did not interfere with the efficacy of the chemotherapy (indicated by the decrease in CA19-9 serum levels), consistent with the results obtained in the pancreatic xenograft animal model described in Example 1. See Table 25 below.

TABLE 25

CA19-9 Serum levels (U/mL)

| Patient ID | Cycle 1 Day 1 | Cycle 2 Day 1 | Cycle 3 Day 1 | Cycle 4 Day 1 |
|---|---|---|---|---|
| 2001 | 4,775 | 5,934 | 8,529 | 9,926 |
| 6002 | 125 | 71 | 27 | 15 |
| 6003 | 6,186 | 4,392 | 2,669 | 2405 |
| 6004 | 6,275 | 4,018 | 1,433 | 348 |
| 6006 | 395 | 490 | 251 | 108 |
| 6007 | 70,086 | 22,958 | 10,286 | |
| 7001 | 2,138 | 502 | 328 | 288 |
| 7002 | 483 | 453 | 205 | 110 |
| 8001 | 11 | 17 | 15 | 20 |
| 9001 | 326 | 710 | 164 | 69 |

All ten patients showed a response to treatment despite extensive metastatic disease at the start of the clinical trial: 5 patients showed a partial response and 5 patients showed stable disease, as measured using RECIST Criteria. See FIG. 12A. After three or four full cycles of treatment, no patient showed any clinical or radiographic evidence of progressive disease. Patients 2001 and 6002 also exhibited reduction in the size of liver and lung or nodal metastases by the fourth cycle of treatment. As shown in FIG. 11A, Liver metastases in patient 2001 have disappeared and pulmonary lesions have decreased in size, with minimal clinical symptoms of metastatic disease, despite rising CA19-9 levels. Patient 6002 showed stable disease and a reduction in the size of metastatic lesions in the liver and lymph nodes. See FIGS. 11B-C. Patient 6003, who presented with lung metastases, also showed stable disease, as shown in FIG. 11D. Patient 6006 showed stable disease and some reduction in the size pancreatic and metastatic lesions in the liver. See FIG. 11E. Patient 8001 showed stable disease with a reduction in the size of pancreatic tumor at the end of cycle 2. See FIG. 11F. FIGS. 12B-F show that patients 6004, 6007, 7001, 7002, and 9001 had a partial response. Eastern Cooperative Oncology Group (ECOG) Performance status in 7 evaluable patients was stable or improved after 8 weeks in the trial (at day 1 of treatment cycle 3).

The treatment regimen also appears to have minimal adverse effects on weight, as most patients have experienced minimum weight loss or even some weight gain. See Table 26 below.

TABLE 26

| | Weight (in pounds) | | | | | |
|---|---|---|---|---|---|---|
| Patient ID | Cycle 1 Day 1 | Cycle 2 Day 1 | Cycle 3 Day 1 | Cycle 4 Day 1 | Cycle 5 Day 1 | Cycle 6 Day 1 |
| 2001 | 125 | 124 | 119 | 120 | | |
| 6002 | 163 | 164 | 169 | 173 | 177 | 176 |
| 6003 | 147 | 140 | 144 | 139 | 137 | 133 |
| 6004 | 158 | 155 | 157 | 153 | 156 | 157 |
| 6006 | 189 | 187 | 188 | 185 | 188 | |
| 6007 | 110 | 115 | 112 | 115 | | |
| 7001 | 163 | 164 | 162 | 164 | 163 | |
| 7002 | 197 | 191 | 186 | 170 | 167 | |
| 8001 | 160 | 164 | 166 | 166 | | |
| 9001 | 137 | 135 | 134 | 129 | 127 | |

As shown in Table 27 below, ODSH infusion did not result in anticoagulation, as determined by partial thromboplastin time (aPTT) in the patients.

TABLE 27

| | aPTT (in seconds) | | | |
|---|---|---|---|---|
| Patient ID | Cycle 1 Day 1 | Cycle 1 Day 3 | Cycle 1 Day 10 | Cycle 1 Day 17 |
| 2001 | 26 | 34 | 33 | 33 |
| 6002 | 25 | 31 | 36 | |
| 6003 | 29 | 33 | 34 | |
| 6004 | 27 | 31 | 31 | 29 |
| 6006 | 29 | | 34 | 34 |
| 6007 | 24 | 28 | | 28 |
| 7001 | | 33 | 32 | 30 |
| 7002 | 36 | 43 | 38 | 42 |
| 8001 | 33 | 38 | 35 | 36 |
| 9001 | 28 | 31 | 31 | 30 |

In the open-label randomized trial initiated after the run-in period, a significant difference in platelet count was observed between the ODSH arm and the Control arm (no ODSH), as shown in FIGS. 13A and 13B. The median and mean platelet counts at day 15 of the first cycle of chemotherapy (after three doses of chemotherapy) were significantly higher in the patients receiving ODSH in addition to gemcitabine and nab-paclitaxel than in the patients not receiving ODSH (p=0.013 using unpaired t-test, 5 patients in each treatment arm). See FIG. 13A. This effect held true in subsequent cycles 2 through 6 (p=0.0003 after 6 cycles in unpaired t-test). See FIG. 13B and Table 28 below. Furthermore, adjunctive administration of ODSH enhanced platelet recovery by day 1 of a subsequent cycle. FIG. 13B and Table 28 below (compare day 1 of cycles in control arm patients versus ODSH arm patients, p=0.0004 after 6 cycles, unpaired t-test).

TABLE 28

| | | Day 1 | Day 15 | Day 1 (n) | Day 15 (n) |
|---|---|---|---|---|---|
| CONTROL ARM | Cycle 1 | 223 | 95 | 16 | 13 |
| | Cycle 2 | 331 | 107 | 11 | 9 |
| | Cycle 3 | 286 | 95 | 9 | 8 |
| | Cycle 4 | 242 | 101 | 7 | 7 |
| | Cycle 5 | 255 | 85 | 6 | 6 |
| | Cycle 6 | 257 | 50 | 6 | 5 |
| ODSH ARM | Cycle 1 | 248 | 143 | 26 | 26 |
| | Cycle 2 | 336 | 135 | 24 | 21 |
| | Cycle 3 | 393 | 171 | 14 | 13 |
| | Cycle 4 | 404 | 156 | 12 | 12 |
| | Cycle 5 | 389 | 121 | 11 | 8 |
| | Cycle 6 | 371 | 132 | 8 | 8 |

In conclusion, ODSH attenuated the myelosuppressive side effects of the gemcitabine/Abraxane regimen (as compared to patients reported in Von Hoff et al., 2011, *J. Clinical Oncology* 29:1-7 and as compared to patients randomized to receive gemcitabine/Abraxane alone, in the randomized portion of this trial), and increased platelet and neutrophil counts in the patients above levels seen prior to treatment, while preserving the efficacy of the chemotherapy regimen. Furthermore, a reduction in side effects which manifest as constitutional symptoms, such as fatigue, nausea, and vomiting, was also observed. ODSH and other PF4-interacting heparinoids attenuate constitutional symptoms associated with chemotherapy.

Overall, the observed effects may permit intensification of the chemotherapeutic regimen with improved antineoplastic efficacy.

6.4. Example 4: ODSH Attenuates Thrombocytopenia Associated with the Treatment of Acute Myelogenous Leukemia (AML)

A clinical trial is conducted to confirm the therapeutic advantage of ODSH administered adjunctively to induction and consolidation therapy and subsequent allogeneic or autologous bone marrow transplantation in the treatment of acute myelogenous leukemia (AML). Subjects included in the trial are subjects diagnosed with AML who are undergoing induction and consolidation therapy. Subjects are randomly assigned to either a control group (receiving only induction and consolidation therapy) or a treatment group (receiving adjunctive administration of ODSH). ODSH is administered as a continuous infusion (0.375 mg/kg/hr). Subjects in each arm of the trial are evaluated for platelet counts and the need for platelet transfusion. Further metrics evaluated include measurement of circulating levels of PF4 and rate of granulocyte recovery.

Results are obtained which demonstrate that addition of ODSH to standard induction and consolidation therapy attenuates thrombocytopenia.

A second clinical trial is conducted to confirm the advantage of ODSH administered adjunctively to induction and consolidation chemotherapy in the treatment of AML. The trial is an open-label pilot study of ten patients newly diagnosed with AML and not previously treated for AML. Patient treatment regimens are as follows. During an induction phase, 100 mg/m$^2$/day of cytarabine is administered continuously by intravenous infusion for 7 days (Day 1-Day 7) and 12 mg/m$^2$/day of idarubicin is administered by intravenous injection on each of Day 1, Day 2, and Day 3. Four mg/kg ODSH is administered intravenously as a bolus on Day 1 immediately after idarubicin, and is then administered at a dose of 0.25 mg/kg/hr continuously by intravenous infusion on Day 1 to Day 7. For patients under 60 years of age, the induction phase is followed by up to four cycles of consolidation chemotherapy, each cycle consisting of 3 g/m$^2$ cytarabine administered over a period of 3 hours, every 12 hours on Days 1, 3, and 5 or a 5-day cycle. During the consolidation phase, 4 mg/kg ODSH is administered intravenously as a bolus on Day 1 immediately after cytarabine, and is then administered at a dose of 0.25 mg/kg/hr continuously by intravenous infusion on Day 1 to Day 5. Consolidation chemotherapy is initiated no sooner than 28 days from the start of induction chemotherapy. Subjects are evaluated for the degree and duration of thrombocytopenia, based on platelet counts and need for transfusion.

Results are obtained which demonstrate that addition of ODSH to standard induction and consolidation therapy attenuates thrombocytopenia.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating thrombocytopenia other than heparin-induced thrombocytopenia, comprising:
   administering a substantially non-anticoagulating PF4-interacting heparinoid to a subject with thrombocytopenia other than heparin-induced thrombocytopenia in an amount effective to promote thrombopoiesis.

2. The method of claim 1, wherein the amount of PF4-interacting heparinoid is sufficient to maintain platelet levels above levels that indicate grade 3 thrombocytopenia.

3. The method of claim 2, further comprising:
   determining an initial platelet count in a blood sample from the patient.

4. A method of treating neutropenia, comprising:
   administering a substantially non-anticoagulating PF4-interacting heparinoid to the subject with neutropenia in an amount effective to promote neutrophil production.

5. The method of claim 4, wherein the amount of PF4-interacting heparinoid is sufficient to maintain neutrophil levels above levels that indicate grade 3 neutropenia.

6. The method of claim 5, further comprising:
   determining an initial neutrophil count in a blood sample from the patient.

7. The method of claim 1 or 4, wherein the PF4-interacting heparinoid is capable of binding to PF-4.

8. The method of claim 1 or 4, wherein the heparinoid is at least 90% desulfated at each of the 2-O and 3-O positions.

9. The method of claim 8, wherein the heparinoid is at least 95% desulfated at each of the 2-O and 3-O positions.

10. The method of claim 8, wherein the heparinoid is produced by cold alkaline hydrolysis of unfractionated heparin.

11. The method of claim 8, wherein the heparinoid has an average molecular weight of about 8 kDa to about 15 kDa.

12. The method according to claim 11, wherein the PF4-interacting heparinoid has an average molecular weight of about 11 kDa to about 13 kDa.

13. The method of claim 1 or 4, wherein the heparinoid has less anticoagulant activity than unfractionated heparin.

14. The method of claim 1 or 4, wherein the heparinoid has reduced affinity for anti-thrombin III as compared to unfractionated heparin.

15. The method of claim 1 or 4, wherein the heparinoid has reduced anti-Xa activity as compared to unfractionated heparin.

16. The method of claim 1 or 4, wherein the PF4-interacting heparinoid is administered parenterally.

17. The method of claim 16, wherein the PF4-interacting heparinoid is administered intravenously.

18. The method of claim 17, wherein the PF4-interacting heparinoid is administered as one or more bolus injections.

19. The method according to claim 18, wherein the one or more bolus injections are administered at a dose of about 1 mg/kg to about 10 mg/kg.

20. The method of claim 17, wherein the PF4-interacting heparinoid is administered as a continuous infusion.

21. The method of claim 20, wherein the continuous infusion is administered at a dose of about 0.2 mg/kg/hr to about 2 mg/kg/hr.

22. The method of claim 17, wherein the PF4-interacting heparinoid is administered as a bolus followed or preceded by a continuous infusion.

* * * * *